(12) United States Patent
Kalchman et al.

(10) Patent No.: US 6,235,879 B1
(45) Date of Patent: May 22, 2001

(54) APOPTOSIS MODULATORS THAT INTERACT WITH THE HUNTINGTON'S DISEASE GENE

(75) Inventors: Michael Kalchman, Toronto; Michael R. Hayden, Vancouver; Abigail Hackam, Vancouver; Vikramjit S. Chopra, Vancouver; Paul Goldberg, Vancouver, all of (CA)

(73) Assignee: University of British Columbia, Vancouver (CA)

( * ) Notice: Subject to any disclaimer, the term of this patent is extended or adjusted under 35 U.S.C. 154(b) by 0 days.

(21) Appl. No.: 09/085,199

(22) Filed: May 27, 1998

Related U.S. Application Data

(63) Continuation-in-part of application No. 09/142,246, filed as application No. PCT/US96/18370 on Nov. 15, 1996
(60) Provisional application No. 60/006,882, filed on Nov. 17, 1995.

(51) Int. Cl.$^7$ .................................................. C07K 1/00
(52) U.S. Cl. ..................................... 530/350; 530/387.9
(58) Field of Search ................................. 530/350, 387.9

(56) References Cited

PUBLICATIONS

Wanker et al., HIP–I: A Huntingtin Interacting Protein Isolated by the Yeast Two–hybrid System. Human Molecular Genetics, Mar. 1997, vol. 6, No. 3, pp. 487–495, see entire document.

Primary Examiner—Scott W. Houtteman
(74) Attorney, Agent, or Firm—Oppedahl & Larson LLP

(57) ABSTRACT

A family of proteins, including a specific human protein designated as HIP1, has been identified that interact differently with the gene product of a normal (16 CAG repeat) and an expanded (>44 CAG repeat) HD gene. Expression of the HIP1 protein was found to be enriched in the brain. Analysis of the sequence of the HIP1 protein indicated that it includes a death effector domain (DED), suggesting an apoptotic function. Thus, it appears that a normal function of Huntingtin may be to bind HIP1 and related apoptosis modulators, reducing its effectiveness in stimulating cell death. Since expanded huntingtin performs this function less well, there is an increase in HIP1-modulated cell death in individuals with an expanded repeat in the HD gene. This understanding of the likely role of huntingtin and HIP1 or related proteins (collectively "HIP-apoptosis modulating proteins") in the pathology of Huntington's Disease offers several possibilities for therapy. First, because the function of huntingtin apparently depends at least in part on the ability to interact with HIP-apoptosis modulating proteins, added expression (e.g., via gene therapy) of normal (non-expanded) huntingtin or of the HIP-binding region of huntingtin should provide a therapeutic benefit. Other DED-interacting peptides could also be used to mask and reduce the interaction of HIP-apoptosis modulating proteins with the death signaling complex. Alternatively, a mutant form of HIP-protein from which the DED has been deleted might be introduced, for example using gene therapy techniques. Because HIP-apoptosis modulating proteins have been shown to self-associate, a protein with a deleted DED may compete with endogenous HIP-protein in the formation of these associations, thereby reducing the amount of apoptotically-active HIP-protein.

6 Claims, 12 Drawing Sheets

FIG. 4

>Usurpin A
SAEVIHQVEEALDTDEKKMLLFLCRDVAIDVVPPNVRDLLDILRERGKLSVCDLAELLYR
VHRFDLLKRILK >Usurpin B
YRVLMAHIGEDLDKSDVSSLIFLMKDYMGRGKISKHKSFLDLVVELHKLNLVAPDQLDLL
EKCLKNIHRIDLKTKIQK >Casp-8 A
FSRNLYDIGELQDSEDLASLKELSLDYIPQRKOEPIKDALMIFQRLOEKRMLEESNLSFL
KELLFRINRLDLLITYLN >Casp-8 B
YRVMLYQISEEVSREELRSFKFLLQHEISKCKLDDDMNLLDIFIEMEKRVILGEGKLDILK
RVCAQINKSLLKIND >Casp-10 A
FRHKLLTIDSNLGVQDVENLKFLCIGLVPNKKLEKSSSASDVFEHLLAHDLLSEEDPFFL
AELLYIIRQKKLLQHLNC >Casp-10 B
FRNLLYELSEGIDSENLKDMIFLLKDSLPKTEMTSLSFLAFLEKQGKIDEDNLTCLEDLCK
TVVPKLLRNIEK >FADD
FLVLLHSVSSSLSSSELTELKFLCLGRVGKRKLERVQSGLDLFSMLLEQNDLEPGHTEL
LRELLASLRRHDLLRRVDD

>MC159 A
SLPFLRHLLEELDSHEDSLLLFLGHDAAPGCTTVTQALCSLSQQRKLTLAALVEMLYVL
QRMDLLKSRFG

>MC159 B
YHKLMVCVGEELDSSELRALRLFACNLNPSLSTALSESSRPVELVLALENVGLVSPSSV
SVLADMLRTLRRLDLCQQLVE

>E8
FRCLMALVNDFLSDKEVEEHYFLCAPRLESHLEPGSKKSFLRLASLLEDLELLGGDKLT
FLRHLLTTIGRADLVKNLQV

>KS orfk13A
TYEVLCEVARKLGTDDREVVLFLLNVFLPQPTLAQLIGALRALKEEGRLTFPLLAECLPR
AGRRDLLRDLLH >KS orfk13B
YQLTVLHVDGELCARDIRSLIFLSKDTIGSRSTPQTFLHNVYCMENLDLLGPTDVDALMS
MLRSLSRVDLQRQVQT

FIG. 4 (cont.)

>HIP1
SELEADLAEQQHLRQQAADDCEFLRAELDELRRQREDTEKAQRSLSEIERKAQANEQR
YSKLKEKYSELVQNHADLLRKNAE

>HIP1a
GELEEQRKQKQKALVDNEQLRHELAQLRAAQLERERSQGLREEAERKASATEARYNK
LKEKHSELVHVHAELLRKNAD

>mHIP1a
NGLEAELEEQRKQKQKALVDNEQLRHELAQLKALQLEGARNQGLREEAERKASATEA
RYSKLKEKHSELINTHAELLRKNAD

>mHIP1
SELEAELAEQQHLGRQAMDDCEFLRTELDELKRQREDTEKAQRSLTEIERKAQANEQR
YSKLKEKYSELVQNHADLLRKNAE

FIG. 6

```
1 hip1      MLLCQGSEWRRDQQL GTANARQWCPLPQDA QPAGSWERCPPLPPA GRLQGTDHPWGWGRL AGGGERGGLWEGLSH SQRLIHLILLSLPLL  90
2 zk370.3   --------------- --------------- --------------- --------------- --------------- ---MDIHRAQAREVFV  12
                      KAI  E     .K KHART I.GT  H EK     FW V       L    VL WKFCH  . HKLLRDGHP V               RY N    S
1 hip1      VFQTVSINKAINTQE VAVKEKHARTCILGT HHEKGAQTFWSVVNR LPLSSNAVLCWKFCH VFHKLLRDGHPNVLK DSLRYRNELSDMSRM 180
2 zk370.3   RAQLEAVQKAITKNE VPLKPKHARTIIVGT HKEKSSGIFWHTVGR IQLEKHPVLTWKFCH LVHKLLRDGHRKVPE ETYRYVNRFTQLSQF 102
             W HL    GYG              Y KLL       .H K     P PG L   D QL     E D. N F     T           M     L         V.   R  S.
1 hip1      WGHLS-EGYGQLCSI YLKLLRTKMEYHTKN PRFPGNLQMSDRQLD EAGESDVNNFFQLTV EMPDYLECELNLFQT VFNSLDMSRSVSVTA 269
2 zk370.3   WKHLNTSGYPCIES  YCKLLHDRVTFHNKY PVVPGKLDNDSQLK  TL-EGDLDNMFEMTI DMLDQMDALLVLQDR VYEMMNSLRWNSLIP 191
             GQC    PLI .ILD   S  YDY VK .FKL       HS  .      D L G  HR RF     F K        . SSNLQYFK L.    IL LP    PNFL   S
1 hip1      AGQCRLAPLIQVILD CSHLYDYTVKLLFKL HSCLP----ADTLQG HRDRFMEQFTKLKDL FYRSSNLQYFKRLIQ IPQLPENPPNFLRAS 355
2 zk370.3   QGQCMLSPLIIAILD TSKFYDYLVKMIFKL HSQVP----PDALEG HRSRFRTIFERTKKF YEESSNLQYFKYLVS IPTLPSHAPNFLQQS 277
               L    P    E     S                                                           D     I        L    .     K     E
1 hip1      ALSEHISPVVVIPAE ASSPDSEPVLEKDDL MDMDASQQNLFDNKF DDIFGSSFSSDPFNF NSQNGVNKDEKDHLI ERLYREISGLKAQLE 445
2 zk370.3   DLESYRTPHAYLHSE GS------------- ---DGTSLNGHDGEL LNLAEAEPQQ--ASP SSQ----PDPREEQI VMLSRAVEDEKFAKE 346
             E         . Q                                           L              A    .  E ERKA  A       E    R  R K K Y
1 hip1      NMKTES---QRVVLQ LKGHVSELEADLAEQ QHLRQQAADDCEFLR AELDELRRQREDTEK AQRSLSELERKAQAN EQ-RYSKLKEKYSE- 530
2 zk370.3   RLIQEA---RSRIEQ YENRLLQMQGEFDHA KREADENREEAQRLK NELALRDASRTQTDD AR--VKEAELKATAA EE-RFNKMKGVYEK- 429
               H      L              KQ.                  D               L               QR                   E
1 hip1      ---LVQNHADLLRKN AEVTKQVSMARQAQV DLEREKKELEDSLER ISDQGQRKTQEQLEV LESLKQELATSQREL QVLQGSLETSAQSEA 617
2 zk370.3   ---FRSEHVLALTKL GDIQKQLEASEKSKF DKDEE----ITALNR KVEEAQR-------- ------EAGRALTKA EGDAGAVDEMRTQLV 498
             E  EL    D        H  E        Q                AK              .       E     Q A        P
1 hip1      NWAAEFAELEKERDS LVSGAAHREEELSAL RKELQDTQLKLASTE ESMCQLAKDQRKMLL VGSRKAAEQVIQDAL NQLEEPPLIS----- 702
2 zk370.3   KADIEVEELKRTID- -----HLRESHAN-- -QLVQSSAEETNKIR LAELEVAKES-GVGI TQMFDHCEDALQNAT SITYPP--------- 569
              HL            I     E       LA              HL S          A                     CK          A
1 hip1      CAGSADHLLSTVTSI SSCIEQLEKSWSQYL ACPEDISGLLHSITL LAHLTSDAIAHGATT CLRAPPEPADSLTEA CKQYGRETLAYLASL 792
2 zk370.3   ----HLAQSAMNN   LVNILSNER-LDEPL ATKDNV--------- F AGHLLSTTLSAAASA AYTASIESYEGVNDQ CKKV---LAAAKVAF 641
```

FIG. 6 (cont.)

```
                  L    D          LP        DI   .     EM      AI A       IE     RA   G    LEVNE IL
1 hip1    EEEGSLENADSTAMR NCLSKIKAIGEELLP RGLDIKQEELGDLVD KEMAATSAAIETATA RIEEMLSKSRAGDTG VKLEVNERILGCCTS  882
2 zk370.3 SDDSALSRADKMKLL RQDIQTLNSLMISLP LQTDIDKDVVGNELE QEMRRMDDAIRRAVQ EIEAIQRRARESSDG IRLEVNESILANCQA  731

LM .I L..AS   L  Q EIV        SP     EFY  N  WTEGLIS   A KAVG  A V V    AD VV GRGK    F  E L V     EIAASTA
1 hip1    LMQAIQVLIVASKDL QREIVESGRGTASPK EFYAKNSRWTEGLIS ASKAVGWGATVMVDA ADLVVQGRGK----F EELMVCSHELAASTA  968
2 zk370.3 LMSVIMQLIVIASREL QTEIVAAGKAGGSPA EFYKRNHQWTEGLLS AAKAVGVAARVLVES ADGVVTGKGK----F EHLIVAAQEIAASTA  817

QL . S VKADKDSS   L  L  A   VNQ   TA VVA    G  .     DFS   L    K  EM SQV  L  ELE  L  ER KL
1 hip1    QLVAASKVKADKDSP NLAQLQQASRGVNQA TAGVVASTISGKSQI EETDN--MDFSSMTL TQIKRQEMDSQVRVL ELENELQKERQKLGE 1056
2 zk370.3 QLFVSSRVKADKDSS KLDALSVAAKAVNQN TAQVVAAVKNGQTTL NDEGS--LDFSYLSL HAAKKEEMESQVKML ELEQSLNQERAKLAA  905

LRK HY  A  .
1 hip1    LRKKHYELAGVAEGW EEGTEASPPTLQEVV TEKE           1090
2 zk370.3 LRKQHYHMAQLIVANK VSF-----------  ----            923
```

APOPTOSIS MODULATORS THAT INTERACT WITH THE HUNTINGTON'S DISEASE GENE

This application is a continuation-in-part of U.S. patent application Ser. No. 09/142,246 filed Nov. 17, 1998 (national phase of PCT/US96/18370), filed Nov. 16, 1996, which claims priority from U.S. Provisional Application Serial No. 60/006,882, filed Nov. 17, 1995, both of which are incorporated herein by reference.

BACKGROUND OF THE INVENTION

This application relates to a family of apoptosis modulators that interact with the Huntington's Disease gene product, and to methods and compositions relating thereto.

"Interacting proteins" are proteins which associate in vivo to form specific complexes. Non-covalent bonds, including hydrogen bonds, hydrophobic interactions and other molecular associations form between the proteins when two protein surfaces are matched or have affinity for each other. This affinity or match is required for the recognition of the two proteins, and the formation of an interaction. Protein-protein interactions are involved in the assembly of enzyme subunits; in antigen-antibody reactions; in forming the supramolecular structures of ribosomes, filaments, and viruses; in transport; and in the interaction of receptors on a cell with growth factors and hormones.

Huntington's disease is an adult onset disorder characterized by selective neuronal loss in discrete regions of the brain and spinal chord that lead to progressive movement disorder, personality change and intellectual decline. From onset, which generally occurs around age 40, the disease progresses with worsening symptoms, ending in death approximately 18 years after onset.

The biochemical cause of Huntington's disease is unclear. While the biochemical cause of Huntington's disease has remained elusive, a mutation in a gene within chromosome 4p16.3 subband has been identified and linked to the disease. This gene, referred to as the Huntington's Disease or HD gene, contains two repeat regions, a CAG repeat region and a CCG repeat region. Testing of Huntington's disease patients has shown that the CAG region is highly polymorphic, and that the number of CAG repeat units in the CAG repeat region is a very reliable indicator of having inherited the gene for Huntington's disease. Thus, in control individuals and in most individuals suffering from neuropsychiatric disorders other than Huntington's disease, the number of CAG repeats is between 9 and 35, while in individuals suffering from Huntington's disease the number of CAG repeats is expanded and is 36 or greater.

To date, no differences have been observed at either the total RNA, mRNA or protein levels between normal and HD-affected individuals. Thus, the function of the HD protein and its role in the pathogenesis of Huntington's Disease remain to be elucidated.

SUMMARY OF THE INVENTION

We have now identified a protein designated as HIP1, that interact differently with the gene product of a normal (16 CAG repeat) and an expanded (>44 CAG repeat) HD gene. The HIP1 protein originally isolated from a yeast two-hybrid screen is encoded by a 1.2 kb cDNA (Seq. ID. No. 1), devoid of stop codons, that is expressed as a 400 amino acid polypeptide (Seq. ID. No. 2). Subsequent study has elucidated additional sequence for HIP1 such that a 1090 amino acid protein is now known. (Seq. ID No. 5). Expression of the HIP1 protein was found to be enriched in the brain.

Analysis of the sequence of the HIP1 protein indicated that it includes a death effector domain (DED), suggesting an apoptotic function. Thus, it appears that a normal function of huntingtin may be to bind HIP1 and related apoptosis modulators, reducing its effectiveness in stimulating cell death. Since expanded huntingtin performs this function less well, there is an increase in HIP1-modulated cell death in individuals with an expanded repeat in the HD gene. Furthermore, additional members of the same family of proteins have been identified which also contain a DED. Thus, the present invention provides a new class of apoptotic modulators which are referred to as HIP-apoptosis modulating proteins.

This understanding of the likely role of huntingtin and HIP1 or related proteins in the pathology of Huntington's Disease offers several possibilities for therapy. First, because the function of huntingtin apparently depends at least in part on the ability to interact with HIP-apoptosis modulating proteins, added expression (e.g., via gene therapy) of normal (non-expanded) huntingtin or of the HIP-binding region of huntingtin should provide a therapeutic benefit. Other DED-interacting peptides could also be used to mask and reduce the interaction of HIP-apoptosis modulating proteins with the death signaling complex. Alternatively, a mutant form of HIP-protein from which the DED has been deleted might be introduced, for example using gene therapy techniques. Because HIP-apoptosis modulating proteins have been shown to self-associate, a protein with a deleted DED may compete with endogenous HIP-protein in the formation of these associations, thereby reducing the amount of apoptotically-active HIP-protein.

BRIEF DESCRIPTION OF THE DRAWING

FIG. 2 compares the nucleic acid sequences of human and murine HIP1 and HIP1a;

FIG. 3 compares the amino acid sequences of human and murine HIP1 and HIP1a;

FIG. 4 shows the sequences of various death effector domains in comparison to the DED of human and murine HIP1 and HIP1a;

FIG. 6 compares the sequences of human HIP1 with ZK370.3 protein of *C. elegans*;

DETAILED DESCRIPTION OF THE INVENTION

Figure 1:
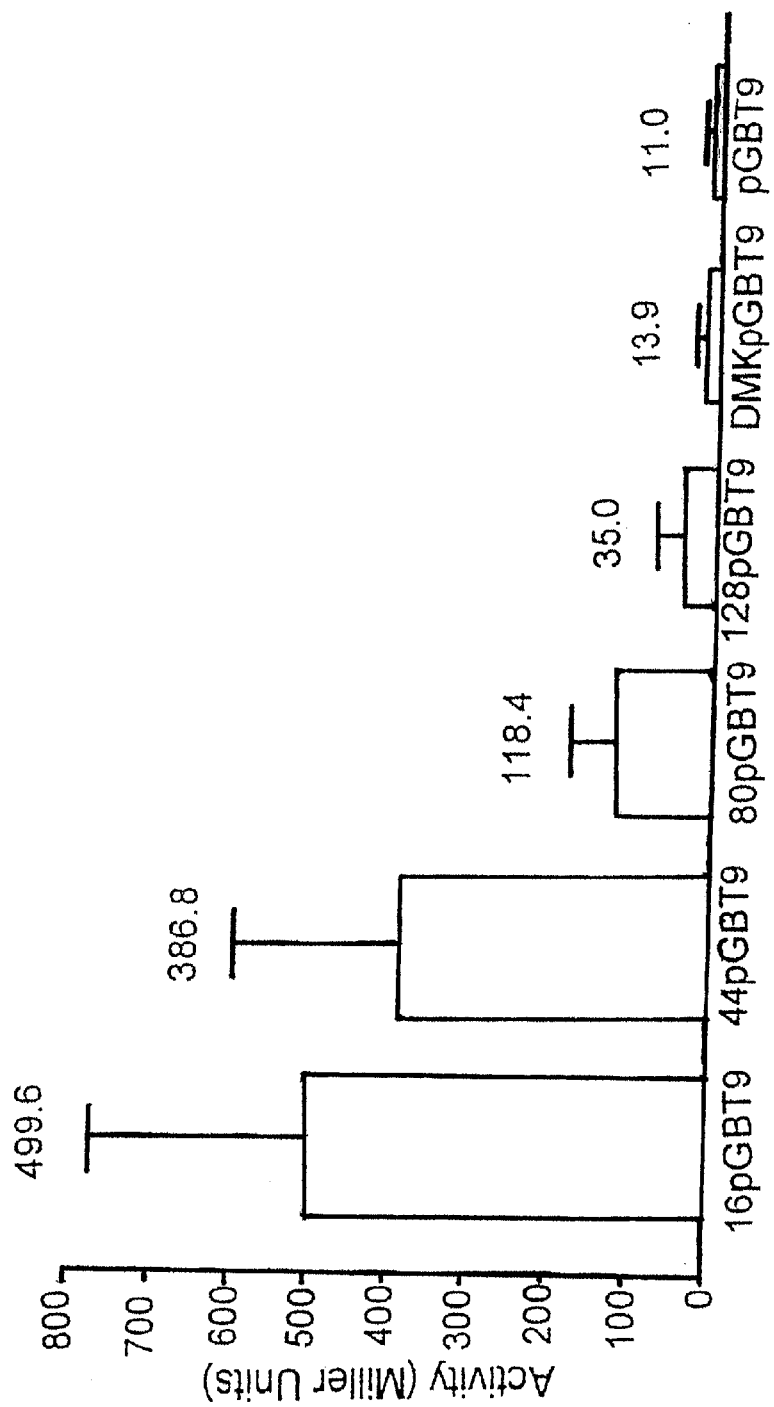
FIG. 1 graphically depicts the amount of interaction between HIP1 and Huntingtin proteins with varying lengths of polyglutamine repeat.

This application relates to a new family of proteins function as modulators of apoptosis. At least some of these proteins, notably the human protein designated HIP1, interact with the gene product of the Huntington's disease gene. Other proteins within the family possess at least 40% and preferably more than 50% nucleotide identity with HIP1 and include a death effector domain (DED). Such proteins are referred to in the specification and claims hereof as "HIP-apoptosis modulating proteins."

The first HIP-apoptosis modulating protein identified was designated as HIP1. HIP1 was identified using the yeast two-hybrid system described in U.S. Pat. No. 5,283,173 which is incorporated herein by reference. Briefly, this system utilizes two chimeric genes or plasmids expressible in a yeast host. The yeast host is selected to contain a detectable marker gene having a binding site for the DNA binding domain of a transcriptional activator. The first chimeric gene or plasmid encodes a DNA-binding domain which recognizes the binding site of the selectable marker gene and a test protein or protein fragment. The second chimeric gene or plasmid encodes for a second test protein and a transcriptional activation domain. The two chimeric genes or plasmids are introduced into the host cell and expressed, and the cells are cultivated. Expression of the detectable marker gene only occurs when the gene product of the first chimeric gene or plasmid binds to the DNA binding domain of the detectable marker gene, and a transcriptional activation domain is brought into sufficient proximity to the DNA-binding domain, an occurrence which is facilitated by protein-protein interactions between the first and second test proteins. By selecting for cells expressing the detectable marker gene, those cells which contain chimeric genes or plasmids for interacting proteins can be identified, and the gene can be recovered and identified.

In testing for Huntington Interacting Proteins, several different plasmids were prepared containing portions of the human HD gene. The first four, identified as 16pGBT9, 44pGBT9, 80pGBT9 and 128pGBT9, were GAL4 DNA binding domain-HD in-frame fusions containing nucleotides 314 to 1955 (amino acids 1–540) of the published HD cDNA sequences cloned into the vector pGBT9 (Clontech). These plasmids contain a CAG repeat region of 16, 44, 80 and 128 glutamine-encoding repeats, respectively. A clone (DMK BamHIpGBT9) was made by fusing a cDNA encoding the first 544 amino acids of the myotonic dystrophy gene (a gift from R. Korneluk) in-frame with the GAL4-DNA BD of pGBT9 and was used as a negative control.

These plasmids have been used to identify and characterize HIP1, as well as two additional HD-interacting proteins, HIP2 and HIP3, which have not yet been tested for function as apoptosis modulators. These plasmids can be further used for the identification of additional interacting proteins which do act as apoptosis modulators, and for tests to refine the region on the protein in which the interaction occurs. Thus, one aspect of the invention is these four plasmids, and the use of these plasmids in identifying HD-interacting proteins. Furthermore, it will be appreciated that the GAL4 DNA-binding and activating domains are not the only domains which can be used in the yeast two-hybrid assay. Thus, in a broader sense, the invention encompasses. any chimeric genes or plasmids containing nucleotides 314 to 1955 of the HD gene together with an activating or DNA-binding domain suitable for use in the yeast one, two- or three-hybrid assay for proteins critical in either binding to the HD protein or responsible for regulated expression of the HD gene.

After introducing the plasmids into Y190 yeast host cells, transforming the host cells with an adult human brain Matchmaker™ (Clontech) cDNA library coupled with a GAL4 activating domain, and selecting for the expression of two detectable marker genes to identify clones containing genes for interacting proteins, the activating domain plasmids were recovered and analyzed. As a result of this analysis, three different cDNA fragments were identified as encoding for HD-interacting proteins and designated as HIP1, HIP2 and HIP3. The nucleic acid sequence of HIP1, as originally recovered in the yeast two-hybrid assay, is given in Seq. ID. No 1. The polypeptide which it encodes is given by Seq. ID No. 2. Further investigation of the HIP1 cDNA resulted in the characterization of a longer region of cDNA totaling 4795 bases and a corresponding protein, the sequences of which are given by Seq ID Nos. 3 and 4, respectively. A further portion of the HIP1 protein was characterized, extending the length to the complete protein sequence of 1090 amino acids (Seq. ID No. 5)

The cDNA molecules encoding HIP-apoptosis modulating proteins, particularly those encoding portions of HIP1, can be explored using oligonucleotide probes for example for amplification and sequencing. In addition, oligonucleotide probes complementary to the cDNA can be used as diagnostic probes to localize and quantify the presence of HIP1 DNA. Probes of this type with a one or two base mismatch can also be used in site-directed mutagenesis to introduce variations into the HIP1 sequence which may increase or decrease the apoptotic activity. Preferred targets for such mutations would be the death effector domains. Thus, a further aspect of the present invention is an oligonucleotide probe, preferably having a length of from 15–40 bases which specifically and selectively hybridizes with the cDNA given by Seq. ID No. 1 or 3 or a sequence complementary thereto. As used herein, the phrase "specifically and selectively hybridizes with" the cDNA refers to primers which will hybridize with the cDNA under stringent hybridization conditions.

Probes of this type can also be used for diagnostic purposes to characterize risk of Huntington's Disease like symptoms arising in individuals where the symptoms are present in the family history but are not associated with an expansion of the CAG repeat. Such symptoms may arise from a mutation in HIP1 or other HIP-apoptosis modulating protein which alters the interaction of this protein with huntingtin, thereby increasing the apoptotic activity of the protein even in the presence of a normal (non-expanded) huntingtin molecule. An appropriate probe for this purpose would one which hybridizes with or adjacent to the huntingtin binding region of the HIP-apoptosis modulating protein. In HIP1, this lies within amino acids 129–514.

DNA sequencing of the HIP1 cDNA initially isolated from the yeast two-hybrid screen (Seq. ID No. 1) revealed a 1.2 kb cDNA that shows no significant degree of nucleic acid identity with any stretch of DNA using the blastn program at ncbi (blast@ncbi.nlm.nih.gov). When the larger HIP1 cDNA sequence (SEQ ID NO. 3) was translated into a polypeptide, the HIP1 cDNA coding (nucleotides 328–3069) is observed to be devoid of stop codons, and to produce a 914 amino acid polypeptide. A polypeptide identity search revealed an identity match over the entire length of the protein (46% conservation) with that of a hypothetical protein from *C. elegans* (ZK370.3 protein; *C. elegans* cosmid ZK370). This *C. elegans* protein shares identity with the mouse talin gene, which encodes a 217 kDa protein implicated with maintaining integrity of the cytoskeleton. It also shares identity with the SLA2/MOP2/END4 gene from *Saccharomyces cerevisiae*, which is known to code for an essential cytoskeletal associated gene required for the accumulation and or maintenance of plasma membrane $H^+$-ATPase on the cell surface. When pairwise comparisons are performed between HIP1 and the *C. elegans* ZK370.3 protein (Genpept accession number celzk370.3), it shows 26% complete identity and an overall 46% level of conservation. Comparative analysis between HIP1 and SLA2/MOP2/END4 (EMBL accession number Z22811) demonstrate similar conservation (20% identity, 40% conservation).

Further exploration revealed several important facts about HIP1 that implicate it in a significantly in the pathogenesis of Huntington's Disease. First, as shown in FIG. 1, it was found that the native interaction between HD protein and HIP1 is influenced by the number of CAG repeats. Second, it was found that expression of the HIP1 protein is enriched in the brain. The highest amounts of expression are in the cortex, with lower levels being seen in the cerebellum, caudate and putamen.

It has also been observed that huntingtin proteins with expanded polyglutamine tracts can aggregate into large, irregularly shaped deposits in HD brains, transgenic mice and in vitro cell culture. We have shown that in HEK (human embryonic kidney) 293T cells, the aggregation of full-length and smaller huntingtin fragments occurs after the cells have been exposed to a period of apoptotic stress. Martindale, et al., *Nature Genetics* 18: 150–154 (1998). In order to assess the consequence of HIP1 expression in cultured cells, we used huntingtin aggregation as one marker of viability. What we found was that cells cotransfected with huntingtin (128 CAG repeats) and HIP1 contained aggregates comparable to those observed following application of apoptotic stress with sub-lethal doses of tamoxifen in 14% of the cells, and that these cells were the ones in which both genes had been introduced as reflected by a double marker experiment. Transfection of a gene encoding a fusion protein of 128 repeat huntingtin and the DED domain from HIP1 ligated in the sense orientation resulted in aggregate formation in 30 to 50% of the cells.

The implications of the apoptotic activity of HIP1 are two-fold. First, the fact that this activity is apparently differentially modulated by interaction with huntingtin having normal and expanded repeats implicates HIP1 in the apoptotic neuronal death which is observed in Huntington's disease and makes HIP1 a logical target for therapy. A second implication of the apoptotic activity of HIP1 is the potential for use of HIP1 as a therapeutic agent to introduce apoptosis in cancer cells.

Therapeutic targeting of HIP1 or other HIP-apoptosis modulating proteins might take any of several forms, but will in general be a treatment involving administration of a composition that reduces the apoptotic activity of the HIP-apoptosis modulating protein. As used in the specification and claims hereof, the term "administration" includes direct administration of a composition active to reduce apoptotic activity as well as indirect administration which might include administration of pro-drugs or nucleic acids that encode the desired therapeutic composition.

One class of composition which can be used in the therapeutic methods of the invention are those compositions which interfere with the activity of HIP-apoptosis modulating proteins by binding to the proteins and mask and reduce the interaction of HIP-apoptosis modulating proteins with the death signaling complex. Within this class of compositions are normal (non-expanded) huntingtin, administered, for example, via increased expression of exogenous HD genes; the HIP-binding region of huntingtin, administered via gene therapy techniques; and other DED-interacting peptides. Other DED-interacting peptides which might be used in a therapeutic method of this type include FADD (Beldin et al., *Cell* 85: 803–815 (1996)) and caspase 8 (Muzio et al., *Cell* 85: 817–827 (1996).

An alternative form of therapy involves the use of a mutant form of HIP1 or other HIP-apoptosis modulating protein from which the DED has been deleted. DED-containing proteins, including HIP1 are self-associating, and this self-association has been shown to be important for activity. (Muzio et al., *Cell* 85: 817–827 (1996). Thus, a protein with a deleted DED may compete with endogenous HIP-protein in the formation of these associations, thereby reducing the amount of apoptotically-active HIP-protein.

Figure 2:
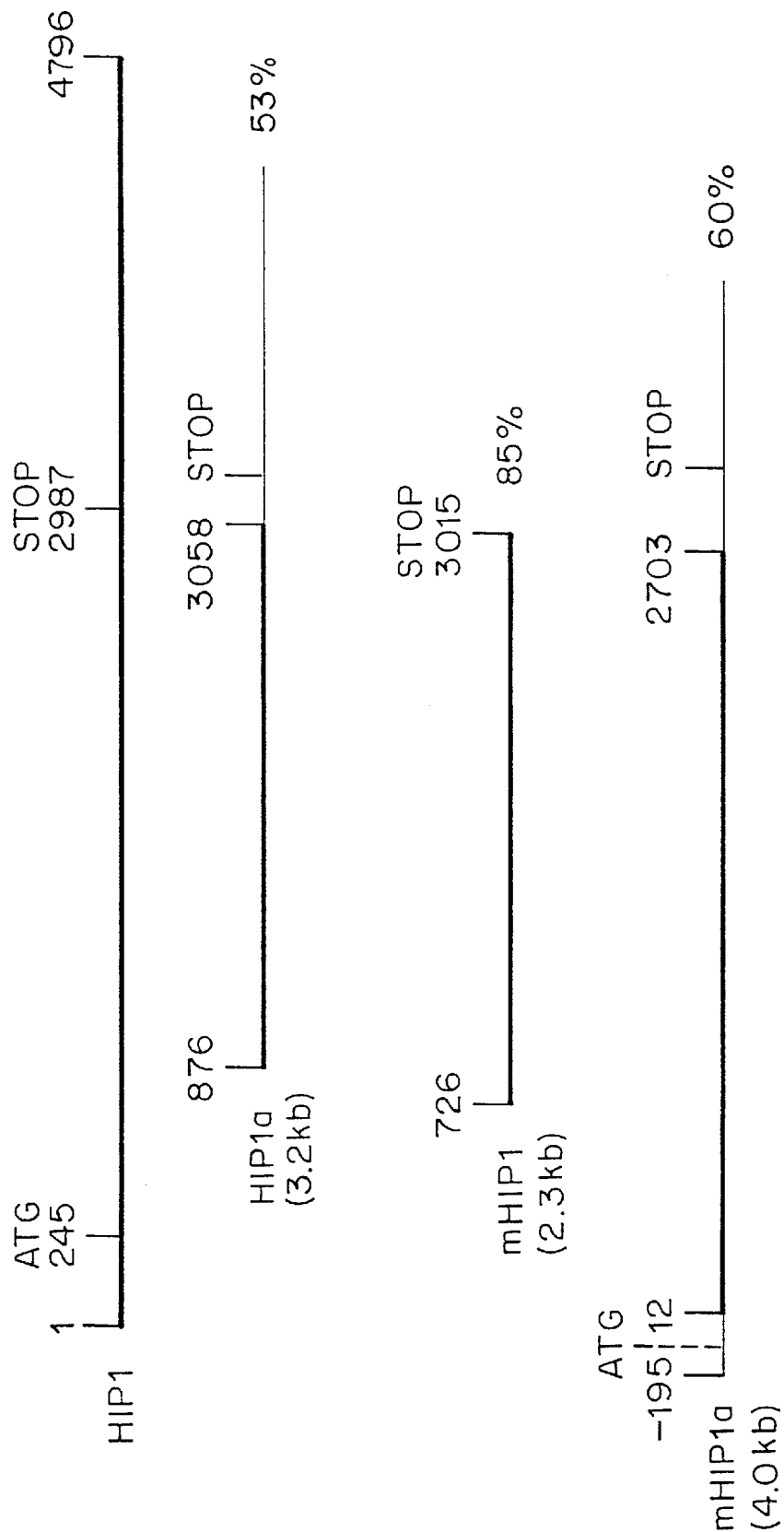
Figure 3:
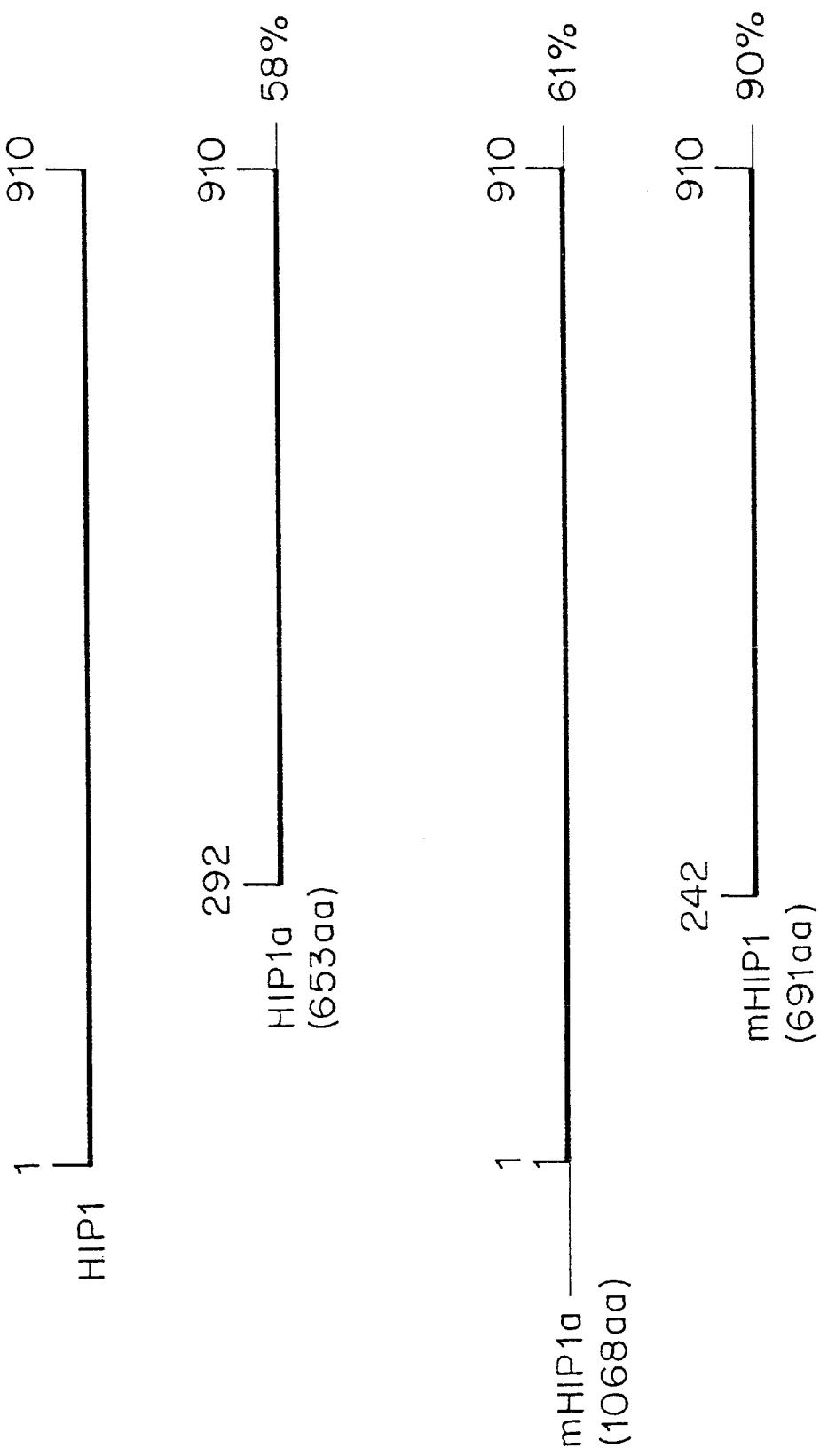

In addition to HIP1, we have identified a further human protein, HIP1a, from a human frontal cortex cDNA library. HIP1a is a family member of HIP1, and thus a HIP-apoptosis modulator in accordance with the invention. A partial sequence of HIP1a (the 5' portion of HIP1a remains to be characterized) is given by SEQ ID Nos. 6 and 7. The isolated and characterized portion of HIP1a shows 53% nucleotide identity and 58% amino acid conservation with HIP1 (Table 1, FIGS. 2 and 3).

We have also isolated 2 mouse proteins mHIP1 and mHIP1a (SEQ. ID Nos. 8–11) which appear to be the murine homologues of human HIP1 and HIP1a. As in the case of human HIP1a, the 5' portion of mHIP1 remains to be isolated. At present, mHIP1 shows 85% nucleotide identity and 90% amino acid conservation with huHIP1 (Table 1, FIGS. 2 and 3). mHIP1a shows 60% nucleotide identity and 61% amino acid conservation with huHIP1 (Table 1, FIGS. 2 and 3). mHIP1a shows stronger homology to huHIP1a; it shows 87% nucleotide identity and 91% amino acid conservation with huHIP1a (Table 1, FIGS. 2 and 3). Taken together these findings indicate that mHIP1 is the murine homologue of huHIP1 whereas mHIP1a is most likely the murine homologue of huHIP1a. As mentioned previously, HIP1 shows sequence similarity to Sla2p in *S. cerevisiae* and the hypothetical protein ZK370.3 in *C. elegans*. Similarly, huHIP1a, mHIP1, and mHIP1a show sequence similar to Sla2p and ZK370.3 (Table 2). The carboxy-terminal regions of huHIP1a, mHIP1, and mHIP1a all show considerable homology to the mammalian membrane cytoskeletal-associated protein, talin. This suggests that these 3 proteins may also play a role in the regulation of membrane events through interactions with the underlying cytoskeleton.

HIP1 contains a death effector domain (DED), a domain which is also present in a number of proteins involved in the apoptotic pathway (FIG. 4). This suggests that HIP1 may act as a modulator of the apoptosis pathway. The DED in huHIP1 is present between amino acid positions 287 and 368. Similarly, HIP1a, mHIP1, and mHIP1a also contain a DED. In huHIP1a the DED is present at amino acids 1–78 of the recovered fragment. In mHIP1 and mHIP1a, the DED are present at amino acids 128–210 and 388–470, respectively. The DED present in huHIP1a, mHIP1 and mHIP1a all show significant percentage amino acid conservation to the DED present in huHIP1 (Table 3).

Increasing expression of normal (non-expanded) huntingtin or the HIP-apoptotic modulator-binding portion thereof, a modified HIP-apoptotic modulator in which the DED has been deleted or of a DED-interacting protein or peptide can be accomplished using gene therapy approaches. In general, this will involve introduction of DNA encoding the appropriate protein or peptide in an expressable vector into the brain cells. Expression of HIP-apoptosis modulating proteins may also be useful in treatment of cancer in which case application to other cell types would be desired, and cells expressing HIP-apoptosis modulating proteins may be used for screening of therapeutic compounds. Thus, in a more general sense, expression vectors are defined herein as DNA sequences that are required for the transcription of cloned copies of genes and the translation of their mRNAs in an appropriate cell type. Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant HIP-apoptosis modulating proteins or fragments thereof in mammalian cells. Commercially available mammalian expression vectors which may be suitable for recombinant HIP-apoptosis modulating protein expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Other vectors which have been shown to be suitable expression systems in mammalian cells include the herpes simplex viral based vectors: pHSV1 (Geller et al. Proc. Natl. Acad. Sci 87:8950–8954 (1990)); recombinant retroviral vectors: MFG (Jaffee et al. Cancer Res. 53:2221–2226 (1993)); Moloney-based retroviral vectors: LN, LNSX, LNCX, LXSN (Miller and Rosman Biotechniques 7:980–989 (1989)); vaccinia viral vector: MVA (Sutter and Moss Proc. Natl. Acad. Sci. 89:10847–10851 (1992)); recombinant adenovirus vectors: pJM17 (Ali et al Gene Therapy 1:367–384 (1994)), (Berkner K. L. Biotechniques 6:616–624 1988); second generation adenovirus vector: DE1/DE4 adenoviral vectors (Wang and Finer Nature Medicine 2:714–716 (1996)); and Adeno-associated viral vectors: AAV/Neo (Muro-Cacho et al. J. Immunotherapy 11:231–237 (1992)).

The expression vector may be introduced into host cells via any one of a number of techniques including but not limited to transformation, transfection, infection, protoplast fusion, and electroporation. The expression vector-containing cells are clonally propagated and individually analyzed to determine whether they produce the desired protein. Delivery of retroviral vectors to brain and nervous system tissue has been described in U.S. Pat. Nos. 4,866,042, 5,082,670 and 5,529,774, which are incorporated herein by references. These patents disclose the use of cerebral grafts or implants as one mechanism for introducing vectors bearing therapeutic gene sequences into the brain, as well as an approach in which the vectors are transmitted across the blood brain barrier.

To further illustrate the methods of making the materials which are the subject of this invention, and the testing which has established their utility, the following non-limiting experimental procedures are provided.

EXAMPLE 1

Identification of Interacting Proteins
GAL4-HD cDNA Constructs

An HD cDNA construct (44pGBT9), with 44 CAG repeats was generated encompassing amino acids 1–540 of the published HD cDNA. This cDNA fragment was fused in frame to the GAL4 DNA-binding domain (BD) of the yeast two-hybrid vector pGBT9 (Clontech). Other HD cDNA constructs, 16pGBT9, 80pGBT9 and 128pGBT9 were constructed, identical to 44pGBT9 but included only 16, 80 or 128 CAG repeats, respectively.

Another clone (DMKDBamHIpGBT9) containing the first 544 amino acids of the myotonic dystrophy gene (a gift from R. Korneluk) was fused in-frame with the GAL4-DNA BD of pGBT9 and was used as a negative control. Plasmids expressing the GAL4-BDRAD7 (D. Gietz, unpublished) and SIR3 were used as a positive control for the β-galactosidase filter assay.

The clones IT15-23Q, IT15-44Q and HAP1 were generous gifts from Dr. C. Ross. These clones represent a previously isolated huntingtin interacting protein that has a higher affinity for the expanded form of the HD protein.

Yeast Strains, Transformations and β-galactosidase Assays

The yeast strain Y190 (MATa leu2-3,112, ura3-52, trp1-901, his3-Δ200, ade2-101, gal4Δgal80Δ, URA3::GAL-lacZ, LYS2::GAL-HIS3,cyc$^r$) was used for all transformations and assays. Yeast transformations were performed using a modified lithium acetate transformation protocol and grown at 30 C using appropriate synthetic complete (SC) dropout media.

The β-galactosidase chromogenic filter assays were performed by transferring the yeast colonies onto Whatman filters. The yeast cells were lysed by submerging the filters in liquid nitrogen for 15–20 seconds. Filters were allowed to dry at room temperature for at least five minutes and placed onto filter paper presoaked in Z-buffer (100 mM sodium phosphate (pH7.0) 10 mM KCl, 1 mM $MgSO_4$) supplemented with 50 mM 2-mercaptoethanol and 0.07 mg/ml 5-bromo-4-chloro-3-indolyl β-D-galactoside (X-gal). Filters were placed at 37 C for up to 8 hours.

Yeast Two-hybrid Screening for Huntingtin Interacting Protein (HIP)

cDNAs from an human adult brain Matchmaker™ cDNA library (Clontech) was transformed into the yeast strain Y190 already harboring the 44pGBT9 construct. The transformants were plated onto one hundred 150 mm×15 mm circular culture dishes containing SC media deficient in Trp, Leu and His. The herbicide 3-amino-triazole (3-AT) (25 mM) was utilized to limit the number of false His+ positives (31). The yeast transformants were placed at 30 C for 5 days and β-galactosidase filter assays were performed on all colonies found after this time, as described above, to identify β-galactosidase+ clones. Primary His+/β-galactosidase+ clones were then orderly patched onto a grid on SC -Trp/-Leu/-His (25 mM 3AT) plates and assayed again for His+ growth and the ability to turn blue with a filter assay. Secondary positives were identified for further analysis. Proteins encoded by positive cDNAs were designated as HIPs (Huntingtin Interactive Proteins). Approximately 4.0× $10^7$ Trp/Leu auxotrophic transformants were screened and of 14 clones isolated 12 represented the same cDNA (HIP1), and the other 2 cDNAs, HIP2 and HIP3 were each represented only once.

The HIP cDNA plasmids were isolated by growing the His+/β-galactosidase+ colony in SC -Leu media overnight, lysing the cells with acid-washed glass beads and electroporating the bacterial strain, KC8 (leuB auxotrophic) with the yeast lysate. The KC8 ampicillin resistant colonies were replica plated onto M9 (-Leu) plates. The plasmid DNA from M9+ colonies was transformed into DH5-a for further manipulation.

EXAMPLE 2

Confirmation of Interactions

The HIP1-GAL4-AD cDNA activated both the lac-Z and His reporter genes in the yeast strain Y190 only when co-transformed with the GAL4-BD-HD construct, but not the negative controls (FIG. 1) of the vector alone or a random fusion protein of the myotonin kinase gene. In order to assess the influence of the polyglutamine tract on the interaction between HIP1 and HD, semi-quantitative β-galactosidase assays were performed. GAL4-BD-HD fusion proteins with 16, 44, 80 and 128 glutamine repeats were assayed for their strength of interaction with the GAL4-AD-HIP1 fusion protein.

Liquid β-galactosidase assays were performed by inoculating a single yeast colony into appropriate synthetic complete (SC) dropout media and grown to OD600 0.6–1.5. Five milliliters of overnight culture was pelleted and washed once with 1 ml of Z-Buffer, then resuspended in 100 ml Z-Buffer supplemented with 38 mM 2-mercaptoethanol, and 0.05% SDS. Acid washed glass beads (~100 ml) were added to each sample and vortexed for four minutes, by repeatedly alternating a 30 seconds vortex, with 30 seconds on ice. Each sample was pelleted and 10 ml of lysate was added to 500 ml of lysis buffer. The samples were incubated in a 30 C waterbath for 30 seconds and then 100 ml of a 4 mg/ml o-nitrophenyl b-D galactopyranoside (ONPG) solution was added to each tube. The reaction was allowed to continue for 20 minutes at 30 C and stopped by the addition of 500 ml of 1 M $Na_2CO_3$ and placing the samples on ice. Subsequently, OD420 was taken in order to calculate the β-galactosidase activity with the equation 1000×OD420/(t×V×OD600) where t is the elapsed time (minutes) and V is the amount of lysate used.

The specificity of the HIP1-HD interaction can be observed using the chromogenic filter assay. Only yeast cells harboring HIP1 and HD activate both the HIS and lacZ reporter genes in the Y190 yeast host. The cells that contain the HIP1 with HD constructs with 80 or 128 CAG repeats turn blue approximately 45 minutes after the cells with the smaller sized repeats (16 or 44).

No difference in the β-galactosidase activity was observed between the 16 and 44 repeats or between the 80 and 128 repeats. However, a significant difference (p<0.05) in activity is seen between the smaller repeats (16 and 44) and the larger repeats (80 and 128). (FIG. 1)

EXAMPLE 3

DNA Sequencing, cDNA Isolation and 5' Race

Oligonucleotide primers were synthesized on an ABI PCR-mate oligo-synthesizer. DNA sequencing was performed using an ABI 373 fluorescent automated DNA sequencer. The HIP cDNAs were confirmed to be in-frame with the GAL4-AD by sequencing across the AD-HIP1 cloning junction using an AD oligonucleotide (5'GAA GAT ACC CCA CCA AAC3'). (Seq. ID No. 12)

Subsequently, primer walking was used to determine the remaining sequences. A human frontal cortex >4.0 kb cDNA library (a gift from S. Montal) was screened to isolate the full length HIP1 gene. Fifty nanograms of a 558 base pair Eco RI fragment from the original HIP1 cDNA was radioactively labeled with [$\alpha^{32}$P]-dCTP using nick-translation and the probe allowed to hybridized to filters containing >105 pfu/ml of the cDNA library overnight at 65° C. in Church buffer (see Northern blot protocol). The filters were washed at 65° C. for 10 minutes with 1×SSPE, 15 minutes at 65 C with 1×SSPE and 0.1% SDS, then for thirty minutes and fifteen minutes with 1×SSPE and 0.1% SDS. The filters were exposed to X-ray film (Kodak, XAR5) overnight at −70 C. Primary positives were isolated and replated and subsequent secondary positives were hybridized and washed as for the primary screen. The resulting positive phage were converted into plasmid DNA by conventional methods (Stratagene) and the cDNA isolated and sequenced.

In order to obtain the most 5' sequence of the HIP1 gene, a Rapid Amplification of cDNA Ends (RACE) protocol was performed according to the manufacturers recommendations (BRL). First strand cDNA was synthesized using the oligo HIP1-242R (5' GCT TGA CAG TGT AGT CAT AAA GGT GGC TGC AGT CC 3'). (Seq. ID No. 13) After dCTP tailing the cDNA with terminal deoxy transferase, two rounds of 35 cycles (94° C. 1 minute; 53° C. 1 minute; 72° C. 2 minutes) of PCR using HIP1-R2 (5' GGA CAT GTC CAG GGA GTT GAA TAC 3') (Seq. ID No. 14) and an anchor primer (5' (CUA)4 GGC CAC GCG TCG ACT AGT ACG GGI IGG GII GGG IIG3') (BRL, Seq. ID No. 15)) were performed. The subsequent 650 base pair PCR product was cloned using the TA cloning system (Invitrogen) and sequenced using T3 and T7 primers. Sequences ID Nos. 1 and 3 show the sequence of the HIP1 cDNAs obtained.

EXAMPLE 4

DNA and Amino Acid Analyses

Overlapping DNA sequence was assembled using the program MacVector and sent via email or Netscape to the BLAST server at NIH (http://www.ncbi.nlm.nih.gov) to search for sequence similarities with known DNA (blastn) or protein (tblastn) sequences. Amino acid alignments were performed with the program Clustalw.

EXAMPLE 5

Fish Detection System and Image Analysis

The HIP1 cDNA isolated from the two-hybrid screen was mapped by fluorescent in situ hybridization (FISH) to normal human lymphocyte chromosomes counterstained with propidium iodide and DAPI. Biotinylated probe was detected with avidin-fluorescein isothiocyanate (FITC). Images of metaphase preparations were captured by a thermoelectrically cooled charge coupled camera (Photometrics). Separate images of DAPI banded chromosomes and FITC targeted chromosomes were obtained. Hybridization signals were acquired and merged using image analysis software and pseudo colored blue (DAPI) and yellow (FITC) as described and overlaid electronically. This study showed that HIP1 maps to a single genomic locus at 7q11.2.

EXAMPLE 6

Northern Blot Analysis

RNA was isolated using the single step method of homogenization in guanidinium isothiocyante and fractionated on a 1.0% agarose gel containing 0.6 M formaldehyde. The RNA was transferred to a hybond N-membrane (Amersham) and crosslinked with ultraviolet radiation.

Hybridization of the Northern blot with b-actin as an internal control probe provided confirmation that the RNA was intact and had transferred. The 1.2 kb HIP1 cDNA was labeled using nick translation and incorporation of $\alpha^{32}$P-dCTP. Hybridization of the original 1.2 kb HIP1 cDNA was carried out in Church buffer (0.5 M sodium phosphate buffer, pH 7.2, 2.7% sodium dodecyl sulphate, 1 mM EDTA) at 55 C overnight. Following hybridization, Northern blots were washed once for 10 minutes in 2.0×SSPE, 0.1% SDS at room temperature and twice for 10 minutes in 0.15×SSPE, 0.1% SDS. Autoradiography was carried our from one to three days using Hyperfilm (Amersham) film at −70 C.

Analysis of the levels of RNA levels of HIP1 by Northern blot data revealed that the 10 kilo base HIP1 message is present in all tissue assessed. However, the levels of RNA are not uniform, with brain having highest levels of expression and peripheral tissues having less message. No apparent differences in RNA expression was noted between control samples and HD affected individuals.

EXAMPLE 7

Tissue Localization of HIP1

Tissue localization of HIP1 was studied using a variety of techniques as described below. Subcellular distribution of HIP-1 protein in adult human and mouse brain Biochemical fractionation studies revealed the HIP1 protein was found to be a membrane-associated protein. No immunoreactivity was seen by Western blotting in cytosolic fractions, using the anti-HIP1-pep1 polyclonal antibody. HIP1 immunoreactivity was observed in all membrane fractions including nuclei (P1), mitochondria and synaptosomes (P2), microsomes and plasma membranes (P3). The P3 fraction contained the most HIP1 compared to other membrane fractions. HIP1 could be removed from membranes by high salt (0.5M NaCl) buffers indicating it is not an integral membrane protein, however, since low salt (0.1–0.25M NaCl) was only able to partially remove HIP1 from membranes, its membrane association is relatively strong. The extraction of P3 membranes with the non-ionic detergent, Triton X-100 revealed HIP1 to be a Triton X-100 insoluble protein. This characteristic is shared by many cytoskeletal and cytoskeletal-associated membrane proteins including actin, which was used as a control in this study. The biochemical characteristics of HIP1 described were found to be identical in mouse and human brain and was the same for both forms of the protein (both bands of the HIP1 doublet). HIP1 co-localized with huntingtin in the P2 and P3 membrane fractions, including the high-salt membrane extractions, as well as in the Triton X-100 insoluble residue. The subcellular distribution of HIP1 was unaffected by the expression of polyglutamine-expanded huntingtin in transgenic mice and HD patient brain samples.

The localization of HIP1 protein was further investigated by immunohistochemistry in normal adult mouse brain tissue. Immunoreactivity was seen in a patchy, reticular pattern in the cytoplasm, appeared excluded from the nucleus and stained most intensely in a discontinuous pattern at the membrane. These results are consistent with the association of HIP1 with the cytoskeletal matrix and further indicate an enrichment of HIP1 at plasma membranes. Immunoreactivity occurred in all regions of the brain, including cortex, striatum, cerebellum and brainstem, but appeared most strongly in neurons and especially in cortical neurons. As described previously, huntingtin immunoreactivity was seen exclusively and uniformly in the cytosol.

The in situ hybridization studies showed HIP1 mRNA to be ubiquitously and generally expressed throughout the brain. This data is consistent with the immunohistochemical results and was identical to the distribution pattern of huntingtin mRNA in transgenic mouse brains expressing full-length human huntingtin.

Protein Preparation and Western Blotting for Expression Studies

Frozen human tissues were homogenized using a Polytron in a buffer containing 0.25M sucrose, 20 mM Tris-HCl (pH 7.5), 10 mM EGTA, 2 mM EDTA supplemented with 10 ug/ml of leupeptin, soybean trypsin inhibitor and 1 mM PMSF, then centrifuged at 4,000 rpm for 10' at 4 C to remove cellular debris. 100–150 ug/lane of protein was separated on 8% SDS-PAGE mini-gels and then transferred to PVDF membranes. Huntingtin and HIP1 were electroblotted overnight in Towbin's transfer buffer (25 mM Tris-HCl, 0.192M glycine, pH8.3, 10% methanol) at 30V onto PVDF membranes (Immobilon-P, Millipore) as described (Towbin et al, *Proc. Nat'l Acad. Sci.(USA)* 76: 4350–4354 (1979)). Membranes were blocked for 1 hour at room temperature in 5% skim milk/TBS (10 mM Tris-HCl, 0.15M NaCl, pH7.5). Antibodies against huntingtin (pAb BKP1, 1:500), actin (mAb A-4700, Sigma, 1:500) or HIP1 (pAb HIP-pep1, 1:200) were added to blocking solution for 1 hour at room temperature. After 3×10 minutes washes in TBS-T (0.05% Tween-20/TBS), secondary Ab (horseradish peroxidase conjugated IgG, Biorad) was applied in blocking solution for 1 hour at room temperature. Membranes were washed and then incubated in chemiluminescent ECL solution and visualized using Hyperfilm-ECL film (Amersham).

Generation of Antibodies

The generation of huntingtin specific antibodies GHM1 and BKP1 is described elsewhere (Kalchman, et al., *J. Biol. Chem.* 271: 19385–19394 (1996)). The HIP1 peptide (VLEKDDLMDMDASQQN, a.a. 76–91 of Seq. ID No. 2) was synthesized with Cys on the N-terminus for the coupling, and coupled to Keyhole limpet hemocyanin (KLH) (Pierce) with succinimidyl 4-(N-maleimidomethyl) cyclohexame-1-carboxylate (Pierce). Female New Zealand White rabbits were injected with HIP1 peptide-KLH and Freund's adjuvant. Antibodies against the HIP1 peptide were purified from rabbit sera using affinity column with low pH elution. Affinity column was made by incubation of HIP1 peptide with activated thio-Sepharose (Pharmacia).

Western blotting of various peripheral and brain tissues were consistent with the RNA data. The HIP1 protein levels observed was not equivalent in all tissues. The protein expression is predominant in brain tissue, with highest amounts seen in the cortex and lower levels seen in the cerebellum and caudate and putamen.

More regio-specific analysis of HIP1 expression in the brain revealed no differential expression pattern in affected individuals when compared to normal controls, with highest levels of expression seen in both controls and HD patients in the cortical regions.

EXAMPLE 8

Co-immunoprecipitation of HIP1 with Huntingtin

Confirmation of the HD-HIP1 interaction was performed using coimmunoprepitation as follows. Control human brain (frontal cortex) lysate was prepared in the same manner as for subcellular localization study. Prior to immunoprecipitation, tissue lysate was centrifuged at 5000 rpm for 2 minutes at 4 C, then the supernatant was pre-cleared by the incubated with excess amount of Protein A-Sepharose for 30 minutes at 4° C., and centrifuged at the same condition. Fifty microliters of supernatant (500 mg protein) was incubated with or without antibodies (10 ug of anti-huntingtin GHM1 (Kalchman, et al. 1996) or anti-synaptobrevin antibody) in the total 500 ul of incubation buffer (20 mM Tris-Cl (pH7.5), 40 mM NaCl, 1 mM $MgCl_2$) for 1 hour at 4° C. Twenty microliters of Protein A-Sepharose (1:1 suspension, for GHM1 and no antibody control) or Protein G-Sepharose (for anti-synaptobrevin antibody; Pharmacia) was added and incubated for 1 hour at 4° C. The beads were washed with washing buffer (incubation buffer containing 0.5% Triton X-100) three times. The samples on the beads were separated using SDS-PAGE (7.5% acrylamide) and transferred to PVDF membrane (Immobilon-P, Millipore). The membrane was cut at about 150 kDa after transfer for Western blotting (as described above). The upper piece was probed with anti-huntingtin BKP1 (1/1000) and lower piece with anti-HIP1 antibody (1/300).

The results showed that when an anti-HIP1 polyclonal antibody was immunoreacted against a blot containing the GHM1 immunoprecipitates from the brain lysate a doublet l( was observed at approximately 100 kDa. When GHM1 was immunoreacted against the same immunoprecipitate the 350 kDa HD protein was also seen The specificity of the HD-HIP1 interaction is seen as no immunoreactive bands seen are as a result of the proteins adsorbing to the Protein-A-Sepharose (Lysate+No Antibody) or when a random, non related antibody (Lysate+anti-Synaptobrevin) is used as the immunoprecipitating antibody.

EXAMPLE 9

Subcellular Fractionation of Brain Tissue

Cortical tissue (20–100 mg/ml) was homogenized, on ice, in a 2 ml pyrex-teflon IKA-RW15 homogenizer (Tekmar Company) in a buffer containing 0.303M sucrose, 20 mM Tris-HCl pH 6.9, 1 mM $MgCl_2$, 0.5 mM EDTA, 1 mM PMSF, 1 mM leupeptin, soybean trypsin inhibitor and 1 mM benzamidine (Wood et al., *Human Molec. Genet.* 5: 481–487 (1996)).

Crude membrane vesicles were isolated by two cycles of a three-step differential centrifugation protocol in a Beckman TLA 120.2 rotor at 4 C based on the methods of Wood et al (1996). The first step precipitated cellular debris and nuclei from tissue homogenates for 5 minutes at 1300×g (P1). The 1300×g supernatant was subsequently centrifuged for 20 minutes at 14000×g to isolate synaptosomes and mitochondria (P2). Finally, microsomal and plasma membrane vesicles were collected by a 35 minute centrifugation at 142000×g (P3). The remaining supernatant was defined as the cytosolic fraction.

High Salt Extraction of Membranes

Aliquots of P3 membranes were twice suspended at 2 mg/ml in 0.5M NaCl, 10 mM Tris-HCl, 2 mM $MgCl_2$, pH7.2, containing protease inhibitors (see above). The same buffer without NaCl was used as a control. The membrane suspensions were incubated on ice for 30 minutes and then centrifuged at 142000×g for 30 minutes.

Extraction of Cytoskeletal and Cytoskeletal-associated Proteins

To extract cytoskeletal proteins, crude membrane vesicles from the P3 fraction membrane were suspended in a volume of Triton X-100 extraction buffer to give a protein: detergent ratio of 5:1. The composition of the Triton X-100 extraction buffer was based on the methods of Arai et al., *J. Neuroscience* 38: 348–357 (1994) and contained 2% Triton X-100, 10 mM Tris-HCl, 2 mM $MgCl_2$, 1 mM leupeptin, soybean trypsin inhibitor, PMSF and benzamidine. Membrane pellets were suspended by hand with a round-bottom teflon pestle, and placed on ice for 40 minutes. Insoluble cytoskeletal matrices were precipitated for 35 minutes at 142000×g in a Beckman TLA 120.2 rotor. The supernatant was defined as non-cytoskeletal-associated membrane or membrane-associated protein and was removed. The remaining pellet was extracted with Triton X-100 a second time using the same conditions. We defined the final pellet as cytoskeletal and cytoskeletal-associated protein.

Solubilization of Protein and Analysis by SDS-PAGE and Western Blotting

Membrane and cytoskeletal protein was solubilized in a minimum volume of 1% SDS, 3M urea, 0.1 mM dithiothreitol in TBS buffer and sonicated. Protein concentration was determined using the BioRad DC Protein assay and samples were diluted at least 1× with 5× sample buffer (250 mM Tris-HCl pH 6.8, 10% SDS, 25% glycerol, 0.02% bromophenol blue and 7% 2-mercaptoethanol) and were loaded on 7.5% SDS-PAGE gels (Bio-Rad Mini-PROTEIN II Cell system) without boiling. Western blotting was performed as described above.

Immunohistochemistry

Brain tissue was obtained from a normal C57BL/6 adult (6 months old) male mouse sacrificed with chloroform then perfusion-fixed with 4% v/v paraformaldehyde/0.01 M phosphate buffer (4% PFA). The brain tissues were removed, immersion fixed in 4% PFA for 1 day, washed in 0.01M phosphate buffered saline, pH 7.2 (PBS) for 2 days, and then equilibrated in 25% w/v sucrose PBS for 1 week. The samples were then snap-frozen in Tissue Tek molds by isopentane cooled in liquid nitrogen. After warming to −20 C, frozen blocks derived from frontal cortex, caudate/putamen, cerebellum and brainstem were cut into 14 mm sections for immunohistochemistry. Following washing in PBS, the tissue sections were blocked using 2.5% v/v normal goat serum for 1 hour at room temperature. Primary antibodies diluted with PBS were applied to sections overnight at 4 C. Optimal dilutions for the polyclonal antibodies BKP1 and HIP1 were 1:50. Using washes of 3×5 minutes in PBS at room temperature, sections were sequentially incubated with biotinylated secondary antibody and then an avidin-biotin complex reagent (Vecta Stain ABC Kit, Vector) for 60 minutes each at room temperature. Color was developed using 3-3'-diaminobenzidine tetrahydrocholoride and ammonium nickel sulfate.

For controls, sections were treated as described above except that HIP1 antibody aliquots were preabsorbed with an excess of HIP1 peptide as well as a peptide unrelated to HIP1 prior to incubation with the tissue sections.

In Situ Hybridization

In situ hybridization was performed as previously described with some modification (Suzuki et al, *BBRC* 219: 708–713 (1996)). The RNA probes were prepared using the plasmid gt149 (Lin, B., et al., *Human Molec. Genet.* 2: 1541–1545 (1994)) or a 558 subclone of HIP1. The antisense and sense single-stranded RNA probes were synthesized using T3 and T7 RNA polymerases and the In Vitro Transcription Kit (Clontech) with the addition of $[\alpha^{35}S]$-CTP (Amersham) to the reaction mixture. Sense RNA probes were used as negative controls. For HIP1 studies normal C57BL/6 mice were used. Huntingtin probes were tested on two different transgenic mouse strains expressing full-length huntingtin, cDNA HD10366 (44CAG) C57BL/6 mice and YAC HD10366(18CAG) FVB/N mice. Frozen brain sections (10 um thick) were placed onto silane-coated slides under RNase-free conditions. The hybridization solution contained 40% w/v formamide, 0.02M Tris-HCl (pH 8.0), 0.005M EDTA, 0.3 M NaCl, 0.01M sodium phosphate (pH 7.0), 1×Denhardt's solution, 10% w/v dextran sulfate (pH 7.0), 0.2% w/v sarcosyl, yeast tRNA (500 mg/ml) and salmon sperm DNA (200 mg/ml). The radiolabelled RNA probe was added to the hybridization solution to give 1×106 cpm/200 ul/section. Sections were covered with hybridization solution and incubated on formamide paper at 65 C for 18 hours. After hybridization, the slides were washed for 30 minutes sequentially with 2×SSC, 1×SSC and high stringency wash solution (50% formamide, 2×SSC and 0.1M dithiothreitol) at 65 C, followed by treatment with RNAse A (1 mg/ml) at 37 C for 30 minutes, then washed again and air-dried. The slides were first exposed on autoradiographic film (b-max, Amersham, UK) for 48 hours and developed for 4 minutes in Kodak D-19 followed by a 5 minute fixation in Fuji-fix. For longer exposures, the slides were dipped in autoradiographic emulsion (50% w/v in distilled water, NR-2, Konica, Japan), air-dried and exposed for 20 days at 4 C then developed as described. Sections were counterstained with methyl green or Giemsa solutions.

EXAMPLE 10

Figure 5:
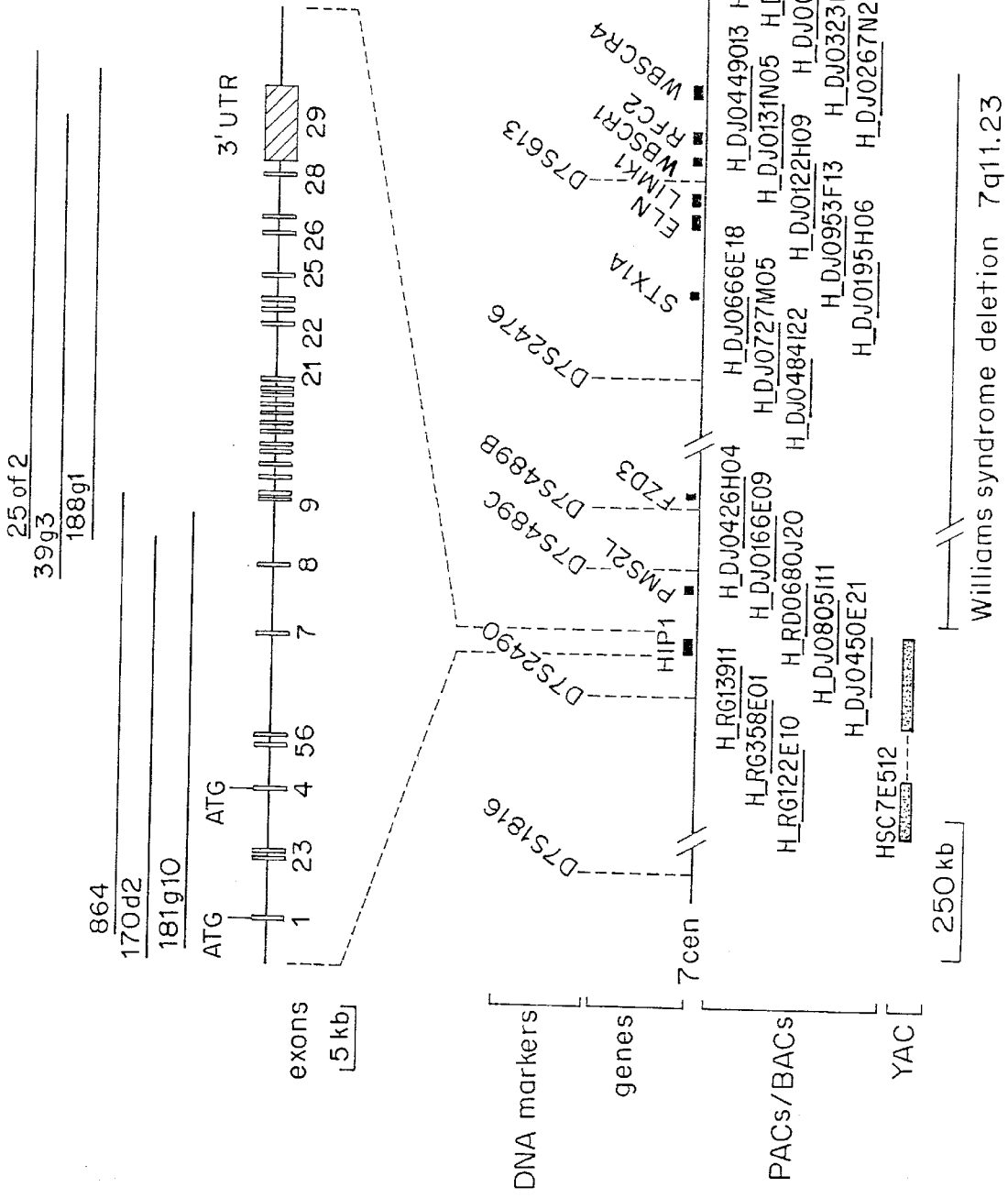
FIG. 5 shows the genomic organization of human HIP1.

We determined a more precise location of the HIP1 gene on chromosome 7 in the context of a physical and genetic map of chromosome 7, and determined its genomic organization. HIP1 maps by FISH and RH mapping to chromosome band 7q11.23, which contains the chromosomal region commonly deleted in Wilhams-Beuren syndrome (WS). We used several methods to refine the mapping of HIP1 in this region. PCR screening of a chromosome 7-YAC-library (Scherer et al., *mammalian Genome* 3: 179–181 (1992)) with primers from the 3' UTR of HIP1 resulted in the identification of only a single positive YAC clone (HSC7E512). This YAC clone had previously been shown to map near the Williams syndrome commonly deleted region (Osborne et al., *Genomics* 45: 402–406 (1997)). The HIP1 cDNA was then used to screen a chromosome 7 specific cosmid library from the Lawrence Livermore National Laboratory (LL07NC01), and the RPCI genomic P1 derived artificial chromosome (PAC) library (Pieter de Jong, Rosswell Park, Buffalo, N.Y.). Several PAC and cosmid clones that were already part of pre-assembled contigs in the Williams syndrome region at 7q11.23 were identified (FIG. 5). Restriction enzyme digestion, blot hybridization experiments and PCR screening confirmed that the clones contained the HIP1 gene.

We determined the exon-intron boundaries and intron sizes of HIP1. Primers were designed based on the sequence of the HIP1 transcript and used to sequence directly from the cosmid, PAC clone and long PCR products from PAC or genomic DNA. Whenever a PCR fragment generated was longer than predicted from the cDNA sequence, it was assumed to contain an intron. The size of the introns was determined by sequencing the intron directly or by PCR amplification of the introns from both genomic DNA and the cosmid or PAC clone from the region. Three sets of overlapping cosmids and a PAC clone that contain the entire coding sequence of HIP1 were characterized (FIG. 5). Cosmid 181G10 and 250F2 were digested with EcoRI and cloned into the plasmid bluescript. Further sequences were generated from these plasmid subclones. Intron-exon boundary sequences were then identified by comparing HIP1 genomic and transcript sequence. The gene is contained within 75 kb and comprises 29 exons and 28 introns. The intron-exon boundary sequences are shown in Table 4, along with the exon and intron sizes. A graphic summary of these data is also shown in FIG. 5. Exons 1 to 28 contained the coding regions. The last and largest exon of the HIP1 gene was found to contain approximately 7 kb. Most of the intron-exon junctions followed the canonical GT-AG rule. An AT was found at the 3' splice site of exon 1 and an AC at the 5' splice site of exon 2. Sequence data from all the exon-intron borders of the coding region and 3'-UTR is set forth in Seq. ID Nos. 16–44. (These sequence have been deposited with GenBank as Accession Nos. AF052261 to AF052288).

Sequence analysis of previously published 5' untranslated region (GenBank accession U79734) revealed the possibility that the open reading frame extends upstream of the ATG in the exon 4 to a 5' ATG in exon 1. Although we failed to obtain any additional 5' sequences despite repeated 5' RACE analyses, an additional ATG, 284 bp upstream of the previously published exon 1 is in the same reading frame and has the surrounding sequence of TGCCATGTT which is similar to the AGCCATGGG, the consensus Kozak sequence (Kozak, M. *Nucl. Acids Res.* 15: 8125–8148 (1987)). If translated from this ATG, the protein would be highly homologous to the N-terminal portion of ZK370.3 and yeast Sla2 protein (FIG. 6). The translated protein in the region of exons 1 to 3 shows an identity of >40% and similarity of >60% to the N-terminal part of ZK370.3. This suggests that the exons 1 to 3 are probably translated.

In western blot studies, HIP1 is identified as a 120 kd protein (11, 23), while the putative translation of the previously published cDNA gives a protein product of estimated molecular weight of approximately 100 kd. If HIP1 gene were translated from the ATG 284 bp upstream of the exon 1, the expected product would have an estimated molecular weight of 122 kd. RNA PCR studies with primers downstream of this ATG and primers in exon 7 amplify expected products of 576 and 600 bp. Taken together these data support the contention that exon 1 extends further 5' and that HIP1 gene is translated from the ATG in exon 1. Sequence analyses showed no TATA, CAAT box or any GC rich promoter sequence upstream of exon 1 ATG. The promoter prediction programs provided by the server http://dot.imgen.bcm.tmc.edu:9331/seq.search/gene.search.html did not predict any promoter upstream of the ATG at position −284, (position 0 corresponds to the first nucleotide of published cDNA, GenBank accession U79734). This suggests that HIP1 may have additional exons.

Finally, we evaluated HIP1 gene as a candidate gene for Huntington disease in families without CAG expansion. In a large study of 1022 patients with a clinical diagnosis of HD, no CAG repeat expansion was found in 12 patients who might represent phenocopies of HD. In at least three families, linkage studies have excluded the HD locus at 4p. Mutation in an interacting protein could result in a similar phenotype as illustrated by the discovery of mutations in dystrophin associated proteins in muscular dystrophies. A mutation in HIP1 may result in altered interaction of huntingtin and HIP1 and lead to cellular toxicity as a result of more HIP1 being free in the cytosol. Thus mutations in huntingtin interacting proteins genes may cause a phenotype suggestive of HD. We studied two of the larger families diagnosed with HD without CAG expansion in HD gene, with the highly informative marker D71816 which maps centromeric and very close to HIP1 gene. The clinical findings in both the families were compatible with a diagnosis of HD, although there were atypical features. In family 1733, HIP1 locus appears to be excluded, as there are two recombinants with the marker. Individuals II-5 and II-7 who do not share the haplotype with the affected individuals are now 41 and 39 years old and have normal neurological examinations.

In the family 1602, a lod score of 1.92 is obtained with the marker D7S1816 at $\theta_{max}$=0. Sequencing of all the coding exons did not reveal any mutation in any exon sequence. The promoter sequence has not been examined. Subsequently a whole genome scan revealed a higher lod scores for markers on chromosome 20p.

EXAMPLE 11

Figure 7:
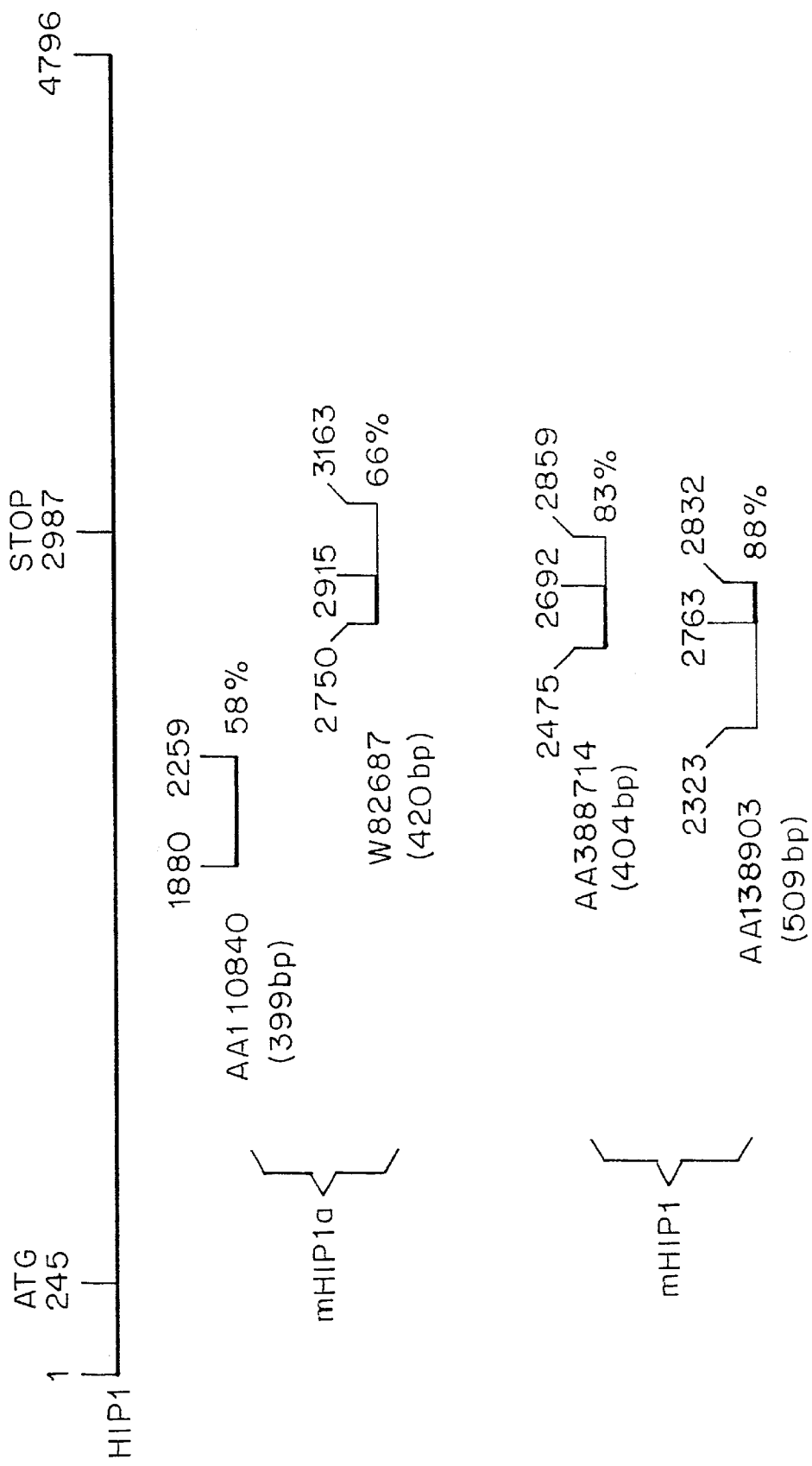
FIG. 7 shows mouse EST's with homology to human HIP1 cDNA used to screen a mouse brain library.

A mouse brain lambda ZAPII cDNA library (Stratagene #93609) was screened with various mouse ESTs which showed homology to the human HIP1 cDNA sequence (see FIG. 7). The ESTs were initially isolated from the non-redundant Database of GenBank EST Division by performing a BLASTN using a fragment of the human HIP1 cDNA as the query. We obtained 4 different ESTs which showed homology to HIP1: 1) aa110840 (clone 520282) which is 399 bp and shows 58% identity, at the nucleotide level, to position 1880 to 2259 of the HIP1 cDNA. 2) w82687 (clone 404331) which is 420 bp and shows 66% identity, at the nucleotide level, to position 2750 to 2915 of the HIP1 cDNA. 3) aa138903 (clone 586510) which is 509 bp and shows 88% identity, at the nucleotide level, to position 2763 to 2832 of the HIP1 cDNA. 4) aa388714 (569088) which is 404 bp and shows 88% identity, at the nucleotide level, to position 2475 to 2692 of the HIP1 cDNA.

mHIP1:

Fifty nanograms of a 362 bp KpnI & PvuII fragment of clone 569088 (containing EST aa388714) was radioactively labeled with [32-P]-dCTP using random-priming. The probe was allowed to hybridize to filters containing >2×10$^5$ pfu/ml of the mouse brain lambda ZAPII cDNA library (Stratagene #93609) overnight at 65° C. in Church buffer (0.5M sodium phosphate buffer (pH 7.2), 2.7% SDS, 1 mM EDTA). The filters were washed at room temperature for 15 minutes with 2×SSPE, 0.1% SDS, then at 65° C. for 20 minutes with 1×SSPE, 0.1% SDS and finally twice at 65° C. with 0.5× SSPE, 0.1% SDS. The filters were exposed to X-ray film (Kodak, XAR5) overnight at −70 C. Primary positives were isolated, replated and subsequent secondary positives were hybridized and washed as for the primary screen. The resulting positive phage was converted into plasmid DNA by conventional methods (Stratagene) and the cDNA termed 4n-n1, was isolated and sequenced 551 bp and 541 bp from the T7 and T3 end, respectively. 4n-n1 is 2.2 kb in length and the T7 end showed 72% identity, at the nucleotide level, to position 1486 to 1715 of the HIP1 cDNA. The 2.2 kb insert from 4n-n1 was excised using EcoRI. Fifty nanograms of the 2.2 kb insert was used to produced a radioactive probe and used to screen the mouse brain lambda ZAPII cDNA library (Stratagene #93609) in the same manner as above. The resulting positive phage was converted into plasmid DNA by conventional methods (Stratagene) and the cDNA termed mHIP1a, was isolated and completely sequenced. mHIP1 is 2.3 kb in length and showed 85% identity, at the nucleotide level, to position 726 to 3072 of the HIP1 cDNA.

mHIP1a:

Fifty nanograms of a 1.3 kb EcoRI & NcoI fragment of clone 404331 (containing EST w82687) was radioactively labeled with [32-P]-dCTP using random-priming. The probe was allowed to hybridize to filters containing >2×10$^5$ pfu/ml of the mouse brain lambda ZAPII cDNA library (Stratagene #93609) overnight at 65° C. in Church buffer (see above). The filters were washed at room temperature for 15 minutes with 2×SSPE, 0.1% SDS, then at 65° C. for 20 minutes with 1×SSPE, 0.1% SDS and finally twice at 65° C. with 0.2× SSPE, 0.1% SDS. The filters were exposed to X-ray film (Kodak, XAR5) overnight at −70° C. Primary positives were isolated, replated and subsequent secondary positives were hybridized and washed as for the primary screen. The resulting positive phage was converted into plasmid DNA by conventional methods (Stratagene) and the cDNA termed mHIP1a, was isolated and completely sequenced. mHIP1a is 3.96 kb in length and shows 60% identity, at the nucleotide level, to position 12 to 2703 of the HIP1 cDNA.

EXAMPLE 12

HIP1a:

The entire mHIP1a cDNA sequence was used to screen the non-redundant Database of GenBank EST Division. We identified a human EST, T08283, which showed homology to mHIP1a. T08383 (clone HIBBB80) is 391 bp and shows 87% identity, at the nucleotide level, to position 2904 to 3113 of the mHIP1a cDNA.

Fifty nanograms of a 1.6 kb HindIII & NotII fragment of clone 404331 (containing EST T08283) was radioactively labeled with [32-P]-dCTP using random-priming. The probe was allowed to hybridize to filters containing >2×10$^5$ pfu/ml of a human frontal cortex lambda cDNA library overnight at 65 C in Church buffer (see above). The filters were washed at 65 C for 10 minutes with 1×SSPE, 0.1% SDS, and then for 30 minutes and 15 minutes with 0.1×SSPE, 0.1% SDS. The filters were exposed to X-ray film (Kodak, XAR5) overnight at −70 C. Primary positives were isolated, replated and subsequent secondary positives were hybridized and washed as for the primary screen. The resulting positive phage was converted into plasmid DNA by conventional methods (Stratagene) and the cDNA termed HIP1a, was isolated and completely sequenced. HIP1a is 3.2 kb in length and shows 53% identity, at the nucleotide level, to position 876 to 3058 of the HIP1 cDNA.

EXAMPLE 13

Following the identification of a 1.2 kb partial human HIP-1 cDNA by yeast two-hybrid interaction studies, a 3.9 kb HIP-1 fragment was isolated from a cDNA library, ligated to a 5' RACE product then subcloned into the mammalian expression vector pCI-neo (Promega). This construct, CMV-HIP-1, expresses HIP-1 from the CMV promoter and was used in the cell expression studies described below. Mouse HIP-1a (mHIP-1a) was also subcloned into a CMV driven expression vector for cell culture expression studies.

EXAMPLE 14

Huntingtin proteins with expanded polyglutamine tracts can aggregate into large, irregularly shaped deposits in HD brains, transgenic mice and in vitro cell culture. We have shown that in HEK (human embryonic kidney) 293T cells the aggregation of full-length and larger huntingtin fragments occurs after the cells have been exposed to a period of apoptotic stress. In order to assess the consequence of HIP-1 expression in cultured cells, we used huntingtin aggregation as one marker of viability.

Human embryonic kidney cells (HEK 293T) were grown on glass coverslips in Dulbecco's modified Eagle medium (DMEM, Gibco, N.Y.) with 10% fetal bovine serum and antibiotics, in 5% CO2 at 37° C. The cells were transfected at 30% confluency with the calcium phosphate protocol by mixing Qiagen-prepared DNA (Qiagen, Calif.) with 2.5 M CaCl$_2$, then incubating at room temperature for 10 min. 2×HEPES buffer (240 mM NaCl, 3.0 mM Na$_2$HPO$_4$, 100 mM HEPES, pH 7.05) was added to the DNA/calcium mixture, incubated at 37° C. for 60 sec, then added to the cells. After 12–18 h, the media was removed, the cells were washed and fresh media was added. At 36 h post-transfection, the cells were exposed to an apoptotic stress by treatment with 35 uM tamoxifen (Sigma) for 1 hour, or left untreated, then processed for immunofluorescence. The cells were washed with PBS, fixed in 4% paraformaldehyde/PBS solution for 20 minutes at room temperature then permeabilized in 0.5% Triton X-100/PBS for 5 min. Following three PBS washes, the cells were incubated with anti-huntingtin antibody MAB2166 (Chemicon) (1:2500 dilution) and anti-HIP-1 antibody HIP-1fp (1:100 dilution) in 0.4% BSA/PBS for 1 h at room temperature in a humidified container. The primary antibody was removed, the cells were washed and secondary antibodies conjugated to Texas red or FITC were added at a 1:600–1:800 dilution for 30 min at room temperature. The cells were then washed again, and the coverslips were mounted onto slides with DAPI (4',6'-diamindino-2 phenylindole, Sigma) as a nuclear counterstain. Immunofluorescence was viewed using a Zeiss (Axioscope) microscope, digitally captured with a CCD camera (Princeton Instrument Inc.) and the images were colourized and overlapped using the Eclipse (Empix Imaging Inc.) software program. Appropriate control experiments were performed to determine the specificity of the antibodies, including secondary antibody only and mock transfected cells.

The huntingtin fragment HD1955 was used in the aggregation studies. This fragment represents the N-terminal 548 amino acids of huntingtin, and corresponds approximately to the polyglutamine-containing fragment produced by caspase 3 cleavage of huntingtin. Transfection of HD1955 with 15 polyglutamines (HD1955-15) results in a diffuse cytoplasmic distribution of the expressed protein. Transfection of HD1955 with 128 polyglutamines (HD1955-128) also results in diffuse cytoplasmic expression. However, exposure of cells transfected with HD1955-128 to tamoxifen results in a marked redistribution of huntingtin. In 29% of cells expressing HD1955-128, the huntingtin protein appears as dense aggregates that are localized in the perinuclear area of the cell. In contrast, less than 1% of HD1955-128 expressing cells contain aggregates in the absence of tamoxifen, and 0% of HD1955-15 cells form aggregates in the presence or absence of tamoxifen treatment.

Co-transfection of HIP-1 and HD1955 was used to test the influence of HIP-1 on huntingtin aggregation. As a control, b-galactosidase was co-transfected with HD1955. In the control transfections, 1–2% of cells expressing HD1955-128 formed aggregates in the absence of tamoxifen, similar to HD1955-128 expressed alone. However, when HD1955-128 was co-expressed with HIP-1, an average of 14% of huntingtin-expressing cells contained aggregates with no tamoxifen treatment. Double-labeling demonstrated that the majority of the cells containing aggregates also expressed HIP-1, directly implicating HIP-1 in the increase in aggregation. Therefore, these results indicate that HIP-1 provides sufficient stress on the huntingtin-expressing cells to form aggregates, to the extent that tamoxifen is no longer necessary.

EXAMPLE 15

We next designed a series of experiments to identify a region of HIP-1 sufficient for inducing aggregate formation of HD1955-128. As described above, HIP-1 contains a domain with high homology to the death effector domains (DED) present in many apoptosis-related proteins. The DED domain of HIP-1 was ligated in-frame to HD1955-128, 3' from the caspase-3 cleavage site. Transfection of the resulting fusion protein with the DED ligated in the sense orientation (HD1955-128-DEDsense) resulted in a large number (30–50%) of cells containing aggregates, without tamoxifen incubation. In contrast, expression of a huntingtin-DED fusion protein with DED in the antisense orientation (HD1955-128-DEDantisense) did not have more aggregates than the HD1955-128 no tamoxifen control. Therefore, the DED domain of HIP-1 is sufficient to stress the cells, causing aggregate formation.

EXAMPLE 16

To directly assess the effect of HIP-1 expression on cell viability, mitochondrial function tests were performed on 293T cells transfected with HIP-1. The assessment of mitochondrial function, using the MTT assay (Carmichael et al., Cancer Res. 47: 936–942 (1987); Vistica et al., Cancer Res. 51: 2515–2520 (1991)), is a standard method to measure cell viability. The MTT assay quantitates the formation of a coloured substrate (formazan), with the mitochondria of viable cells forming more substrate than non-viable cells. Since decreased mitochondrial activity is an early consequence of many cellular toxins, the MTT assay provides an early indicator of cell damage.

For cell viability assays, HEK 293T cells were seeded at a density of $5 \times 10^4$ cells into 96-well plates and transfected with 0.1 ug or 0.08 ug HIP-1 or 0.1 ug of the control construct lacZ using the calcium phosphate method described above. At 24–36 hours post-transfection tamoxifen-treated cells were incubated for 2 hours in a 1:10 dilution of WST-1 reagent (Boehringer Mannheim) and release of formazan from mitochondria was quantified at 450 nm using an ELISA plate reader (Dynatech Laboratories) (Carmichael et al., 1987; Mosmann, J. Immunol. Meth 65: 55–63 (1983)). One way ANOVA and Newman-Keuls test were used for statistical analysis. The transfection efficiency, measured by β-galactosidase staining and immunofluoresence, was approximately 50%.

Figure 8:
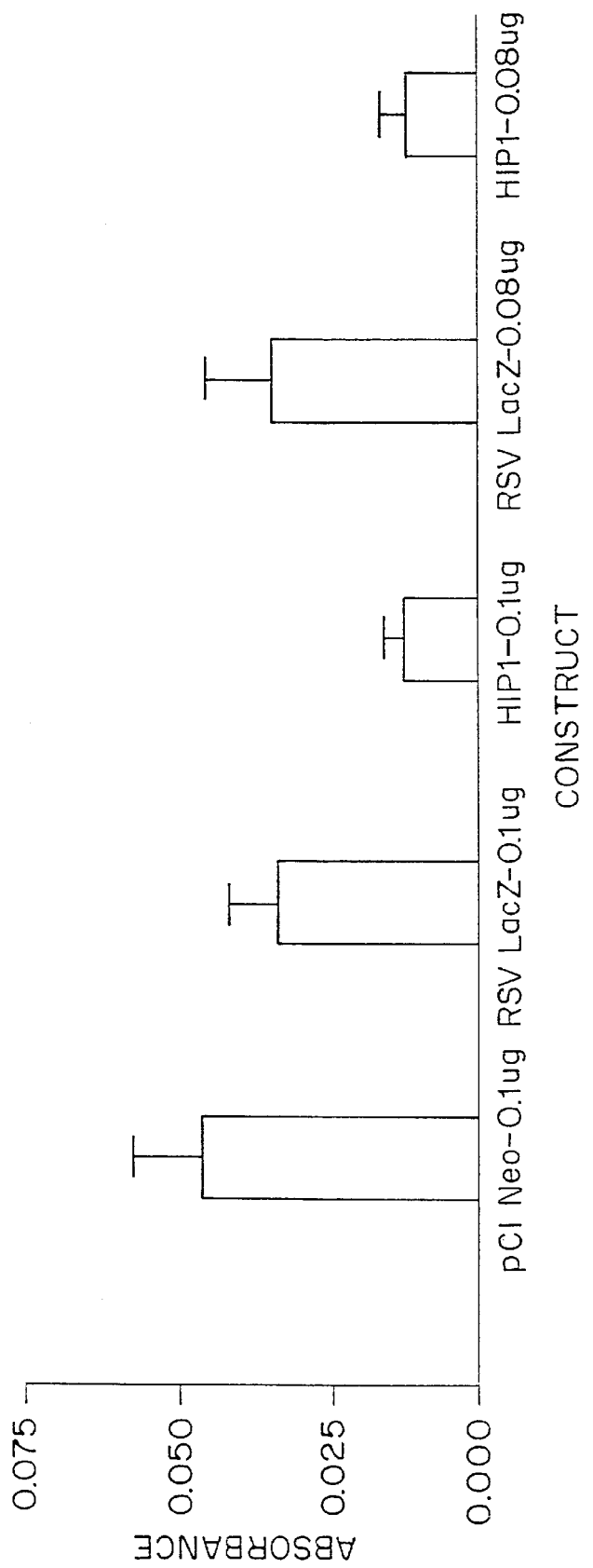
FIG. 8 shows the affect of HIP1 on susceptibility of cells to stress.

We have previously demonstrated that expression of mutant huntingtin results in increased susceptibility to an apoptotic stress induced by sub-lethal doses of tamoxifen in transfected 293T cells (Martindale et al., 1998). A similar assay was used to test the consequence of HIP-1 expression. With 0.1 ug transfected HIP-1 DNA, after 24 hr expression, HIP-1 resulted in increased cell death in response to tamoxifen, compared with the tamoxifen-treated β-galactosidase control ($p<0.01$, $n=4$). Reducing the amount of transfected HIP-1 DNA to 0.08 ug also resulted in increased cell death compared with control ($p<0.01$, $n=4$), indicating the high potency of HIP-1 (FIG. 8). Furthermore, increased cell death in cells transfected with HIP-1 was observed in the absence of apoptotic stress at 48 hrs post-transfection, but was so severe that is could not be accurately quantitated. Thus, an earlier time point (24 hr) had to be used for better reproducibility, using an apoptotic stress to unmask the phenotype.

Figure 9A:
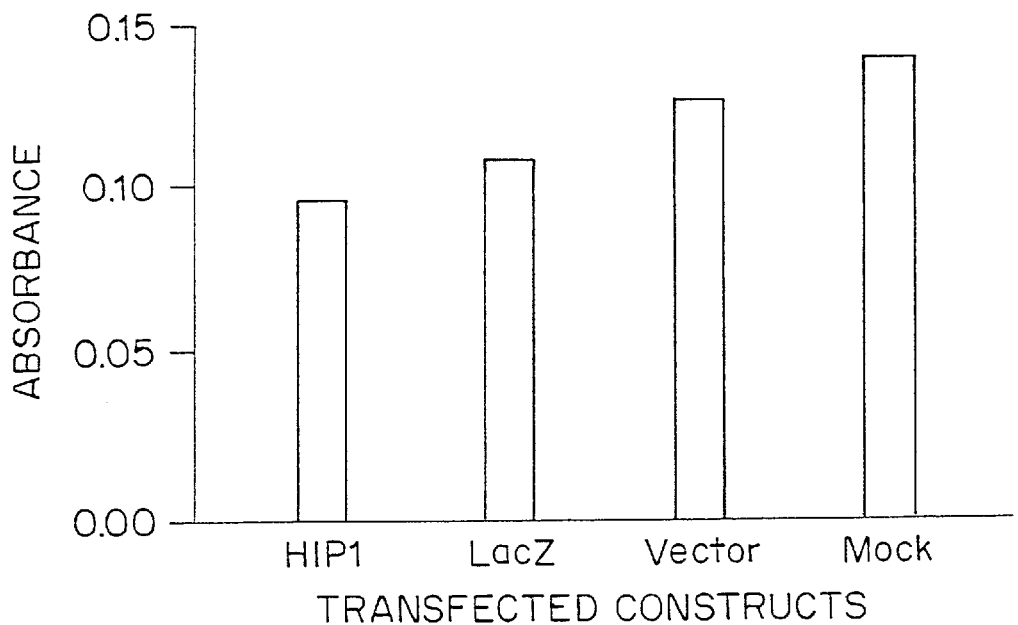
FIGS. 9A–9C show the toxicity of HIP1 in the presence of huntingtin with different lengths of polyglutamine repeats.
Figure 9B:
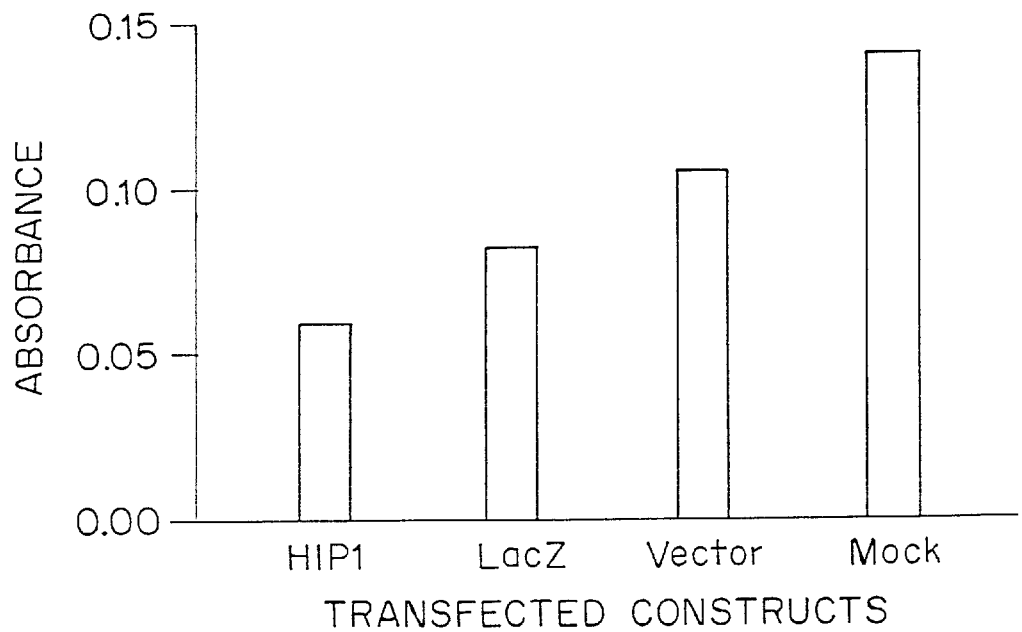
Figure 9C:
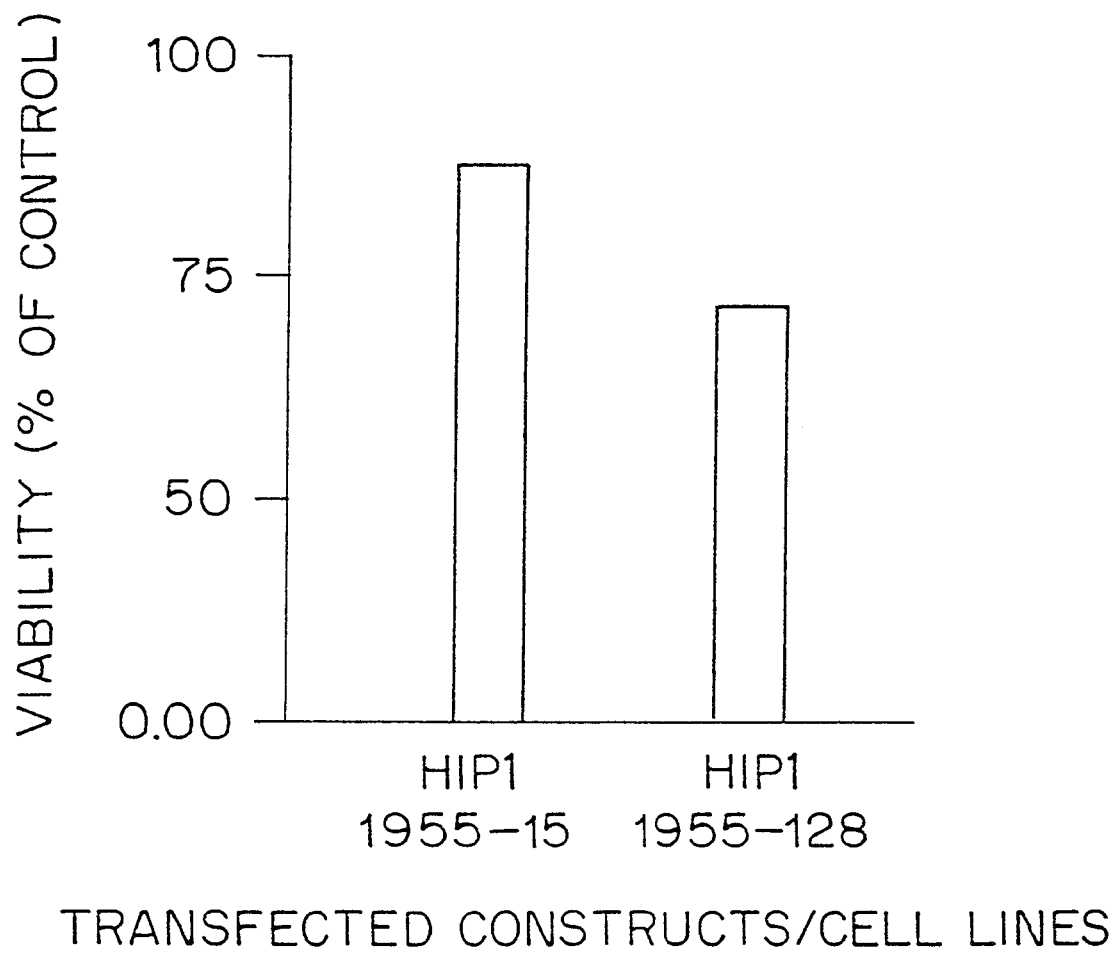

In order to model a pathogenic interaction of HIP-1 and huntingtin in the HEK 293 mammalian cell system, HIP-1 was transfected into cell lines stably expressing huntingtin. Two cell lines were chosen for the initial studies, one line expressed the truncated HD1955 construct with 15 glutamines, and the second expressed the HD1955 with 128 repeats. Western blotting indicated that the cell lines expressed huntingtin at similar levels. To assess whether HIP-1 is toxic in the presence of mutant huntingtin, 0.1 ug HIP-1 DNA was transfected into the HD1955-128 cell line. Transfection of HIP-1 into the HD1955-15 cell line was used as the wild-type huntingtin control, and transfection of LacZ into both cell lines was the control for transfection-related toxicity (FIGS. 9A and 9B). MTT toxicity assays showed that HIP-1 in the presence of mutant huntingtin (HD1955-128) was significantly more toxic than HIP-1 with wild-type huntingtin (HD1955-15), $p<0.001$, $n=4$ (FIG. 9C). This toxicity was observed at 24 hr and 36 hr post-transfection. No tamoxifen was needed to unmask the phenotype, suggesting that the combined cell stress of HIP-1 with truncated huntingtin was sufficient to reduce cell viability over control.

TABLE 1

| Alignment | Percentage Nucleotide Identity | Percentage Amino Acid Conservation |
|---|---|---|
| HIP1 vs HIP1a | 53 | 58 |
| HIP1 vs mHIP1a | 60 | 61 |
| HIP1 vs mHIP1 | 85 | 90 |
| HIP1a vs mHIP1a | 87 | 91 |
| HIP1a vs mHIP1 | 60 | 56 |
| mHIP1a vs mHIP1 | 61 | 71 |

TABLE 2

| Alignment | Percentage Nucleotide Identity | Percentage Amino Acid Conservation |
|---|---|---|
| HIP1 vs SLA2 | 29 | 37 |
| HIP1 vs ZK370.3 | 41 | 46 |
| HIP1a vs SLA2 | 34 | 35 |
| HIP1a vs ZK370.3 | 33 | 31 |
| mHIP1 vs SLA2 | 24 | 29 |
| mHIP1 vs ZK370.3 | 33 | 39 |
| mHIP1a vs SLA2 | 37 | 38 |
| mHIP1a vs ZK370.3 | 33 | 51 |

TABLE 3

| Alignment of DED | Percentage Amino Acid Conservation |
|---|---|
| HIP1 vs HIP1a | 66 |
| HIP1 vs mHIP1 | 94 |
| HIP1 vs mHIP1a | 73 |
| HIP1a vs mHIP1a | 88 |
| HIP1a vs mHIP1 | 63 |
| mHIP1 vs mHIP1a | 57 |

TABLE 4

| Exon | 5" Splice junction | cDNA position | 3" splice junction | Exon Size (bp) | Intron size (Kb) |
|---|---|---|---|---|---|
| 1 |  | 1–59 | CACGCCAGAAatatccttttggatgttgctt | 59 | 5.6 |
| 2 | ttttccataaccccccctcacCGTGCATACT | 60-202 | ACACCCGAACgtgagttcctggggctatgggg | 144 | 0.35 |
| 3 | gtgttcttttgccccctgcagGTCCTGAAGGAC | 203–259 | AGCAGGATGTgggtgagtttggagatgtact | 58 | 5.2 |
| 4 | ttcccctcctcttcctaaaagGGCCACCTGA | 260–340 | CCACACCAAAgtgagtctctgcggacagtt | 81 | 4.6 |
| 5 | ttcctctgcctccttccagAATCCCAGGT | 341–417 | TGAACAACTTgtaagtggctcctgccctgag | 77 | 0.8 |
| 6 | ctctttcctcttgggtccagTTTCCAGTTA | 418–479 | TTCCAAACAGgtgagtctcttccctcccgt | 62 | 10 |
| 7 | ccctcactttattcctagTATTCAACTC | 480–620 | CTCCACTCCTgtgagtaccgcgggccagat | 141 | 5.8 |
| 8 | ctctttccaattcttccagGCCTCCCAGC | 621–878 | AGTTTACAAAgtaagtggttcaagtaacag | 58 | 5.5 |
| 9 | aggtccttctccaccccctagGTTGAAAGAT | 679–754 | GCTGCCTGAGgtaagcatgcccaaccaca | 76 | 0.1 |
| 10 | ggatgtgtctccgtcttcagACCCACCCAA | 755–895 | CTCTCAGCAGgtgaggaccacttgggagaga | 141 | 1.5 |
| 11 | tcactccttttggtcaaccacagAATTTATTT | 896–993 | AGGATGAGAAgtgagtccaagctgggttcaa | 98 | 1.1 |
| 12 | cattcccctctctttcccagGGACCACTTAAT | 994–1066 | GAAGACTGAGgtataacttggatctgctctgcc | 73 | 1.6 |
| 13 | tgaccggagtcccccccacagAGCCAGCGGG | 1067–1250 | GAGATAGAAgtgagcggtgggtggggcg | 184 | 1.4 |
| 14 | cttggtccttacaatacagGGAAAGCTCAAG | 1251–1339 | GCTGCGGAAGgtaagaccctcagccccgtcac | 89 | 0.8 |
| 15 | acactgttcttcttttgcagAATGCAGAGGT | 1340–1456 | GGCCAGCGGAAGgtgagtgggacgaggagc | 117 | 1 |
| 16 | ctgttttcttctctttcagACTCAAGAACA | 1457–1558 | CTTCTGCCCAGgtaaataccctcctttttt | 102 | 1 |
| 17 | ccttgtggtcacctttgcagTCAGAAGCAAA | 1559–1703 | AGCACAGAGGgtcacggacatggac | 145 | 0.8 |
| 18 | acctccctggaccattttagAATCTATGTG | 1704–1838 | GGGTCTGCAGgtacacttgcaattgccagct | 135 | 1.4 |
| 19 | ccctgtgttccctctcacagATCACCTCCT | 1839–1925 | TGCCCAGAAGgtaagaatggccaaggacagt | 87 | 0.3 |
| 20 | cttctctttccaatcctggcagACATCAGTGG | 1928–2033 | CCTGCCGACTgtgagtactggggcatgagg | 107 | 0.5 |
| 21 | ctattgccttgtatctccagCACTGACCGA | 2034–2170 | CATCGGCGAGgtacttggagtagtatcattg | 137 | 5 |
| 22 | cctttgtgatgtgttcacagGAGCTCCTGCCC | 2171–2281 | CCAGAATAGAGgtaggaggttcctgcaggatc | 111 | 1.7 |
| 23 | accatgcttcttttttcacagGAGATGCTCAG | 2282–2340 | TGAATGAAAGgtcggtctgagcggcatggtgg | 59 | 1.3 |
| 24 | tcgacttgtttgtttggcagGATCCTTGGTTG | 2341–2434 | GAGCGGCAGGgtgagcgtgggtgtgggccct | 94 | 2.2 |
| 25 | actattttttatttccctagGGTACAGCATCCCC | 2435–2535 | CCACTGTCATGGTgtaagtatctattggtaccaa | 101 | 3.8 |
| 26 | ttgtcgttttccatcagGGATGCAAGCTGA | 2536–2641 | TGCATCCAAGgtaggacctggctggacctccta | 106 | 1.8 |
| 27 | aatctgctttgtcctggtagGTGAAAGCTGATA | 2642–2765 | GAAGAGACAGgtagccttccaaaggg | 123 | 3.6 |
| 28 | ttgtttccatccttgcagACAACATGGAC | 2766–2936 | TGGGAAGAAGgtaagctgactcaaaggat | 171 | 1.4 |
| 29 | aacataaattatcattgtcttttagGAACAGAGG | 2937– | 3' UTR | 7 Kb | |

What is claimed is:

1. A polypeptide comprising the sequence given by Seq. ID. No. 2.

2. A polypeptide comprising the sequence given by Seq. ID. No. 4.

3. A polypeptide comprising the sequence given by Seq. ID. No. 5.

4. A polypeptide comprising the sequence given by Seq. ID No. 7.

5. An antibody which specifically binds to a polypeptide having a sequence comprising the amino acids listed in Seq. ID. No. 2.

6. The antibody of claim 5, wherein the antibody specifically binds to amino acids 76–91 of the polypeptide having the sequence shown in Seq. ID No. 2.

* * * * *

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
       (A) LENGTH: 1164
       (B) TYPE: nucleic acid
       (C) STRANDEDNESS: single
       (D) TOPOLOGY: linear (ii) MOLECULE TYPE: cDNA (iii) HYPOTHETICAL: no (iv) ANTI-SENSE: no (vi) ORIGINAL SOURCE:
       (A) ORGANISM: human (ix) FEATURE: cDNA for Huntingtin-interacting protein (xi) SEQUENCE DESCRIPTION: SEQ ID NO:1:

| | |
|---|---|
| ACAGCTGACA CCCTGCAAGG CCACCGGGAC CGCTTCATGG AGCAGTTTAC | 50 |
| AAAGTTGAAA GATCTGTTCT ACCGCTCCAG CAACCTGCAG TACTTCAAGC | 100 |
| GGGTCATTCA GATCCCCCAG CTGCCTGAGA ACCCACCCAA CTTCCTGCGA | 150 |
| GCCTCAGCCC TGTCAGAACA TATCAGCCCT GTGGTGGTGA TCCCTGCAGA | 200 |
| GGCCTCATCC CCCGACAGCG AGCCAGTCCT AGAGAAGGAT GACCTCATGG | 250 |
| ACATGGATGC CTCTCAGCAG AATTTATTTG ACAACAAGTT TGATGACNTC | 300 |
| TTTGGCAGTT CATCCAGCAG TGATCCCTTC AATTTCAACA GTCAAAATGG | 350 |
| TGTGAACAAG GATGAGAAGG ACCACTTAAT TGAGCGACTA TACAGAGAGA | 400 |
| TCAGTGGATT GAAGGCACAG CTAGAAAACA TGAAGACTGA GAGCCAGCGG | 450 |
| GTTGTGCTGC AGCTGAAGGG CCACGTCAGC GAGCTGGAAG CAGATCTGGC | 500 |
| CGAGCAGCAG CACCTGCGGC AGCAGGCGGC CGACGACTGT GAATTCCTGC | 550 |
| GGGCAGAACT GGACGAGCTC AGGNGGCAGC GGGAGGACAC CGAGAAGGCT | 600 |
| CAGCGGAGCC TGTCTGAGAT AGAAAGGAAA GCTCAAGCCA ATGAACAGCG | 650 |
| ATATAGCAAG CTAAAGGAGA AGTACAGCGA GCTGGTTCAG AACCACGCTG | 700 |
| ACCTGCTGCG GAAGAATGCA GAGGTGACCA AACAGGTGTC CATGGCCAGA | 750 |
| CAAGCCCAGG TAGATTTGGA ACGAGAGAAA AAAGAGCTGG AGGATTCGTT | 800 |
| GGAGCGCATC AGTGACCAGG GCCAGCGGAA GACTCAAGAA CAGCTGGAAG | 850 |
| TTCTAGAGAG CTTGAAGCAG GAACTTGGCA CAAGCCAACG GGAGCTTCAG | 900 |
| GTTCTGCAAG GCAGCCTGGA AACTTCTGCC CAGTCAGAAG CAAACTGGGC | 950 |
| AGCCGAGTTC GCCGAGCTAG AGAAGGAGCG GGACAGCCTG GTGAGTGGCG | 1000 |
| CAGCTCATAG GGAGGAGGAA TTATCTGCTC TTCGGAAAGA ACTGCAGGAC | 1050 |
| ACTCAGCTCA AACTGGCCAG CACAGAGGAA TCTATGTGCC AGCTTGCCAA | 1100 |
| AGACCAACGA AAAATGCTTC TGGTGGGGTC CAGGAAGGCT GCGGAGCAGG | 1150 |
| TGATACAAGA CGCG | 1164 |

(2) INFORMATION FOR SEQ ID NO:2:

(i) SEQUENCE CHARACTERISTICS:
    (A) LENGTH: 386
    (B) TYPE: amino acid
    (D) TOPOLOGY: linear (ii) MOLECULE TYPE: protein (iii) HYPOTHETICAL: no (vi) ORIGINAL SOURCE:
    (A) ORGANISM: human (ix) FEATURE:
    (D) OTHER INFORMATION: Huntington-interacting protein (xi) SEQUENCE DESCRIPTION: SEQ ID NO:2:

```
Thr Ala Asp Thr Leu Gln Gly His Arg Asp Arg Phe Met Glu Gln
  1               5                  10                  15

Phe Thr Lys Leu Lys Asp Leu Phe Tyr Arg Ser Ser Asn Leu Gln
                 20                  25                  30

Tyr Phe Lys Arg Val Ile Gln Ile Pro Gln Leu Pro Glu Asn Pro
                 35                  40                  45

Pro Asn Phe Leu Arg Ala Ser Ala Leu Ser Glu His Ile Ser Pro
                 50                  55                  60

Val Val Val Ile Pro Ala Glu Ala Ser Ser Pro Asp Ser Glu Pro
                 65                  70                  75

Val Leu Glu Lys Asp Asp Leu Met Asp Met Asp Ala Ser Gln Gln
                 80                  85                  90

Asn Leu Phe Asp Asn Lys Phe Asp Asp Phe Gly Ser Ser Ser Ser
                 95                 100                 105

Ser Asp Pro Phe Asn Phe Asn Ser Gln Asn Gly Val Asn Lys Asp
                110                 115                 120

Glu Lys Asp His Leu Ile Glu Arg Leu Tyr Arg Glu Ile Ser Gly
                125                 130                 135

Leu Lys Ala Gln Leu Glu Asn Met Lys Thr Glu Ser Gln Arg Val
                140                 145                 150

Val Leu Gln Leu Lys Gly His Val Ser Glu Leu Glu Ala Asp Leu
                155                 160                 165

Ala Glu Gln Gln His Leu Arg Gln Gln Ala Ala Asp Asp Cys Glu
                170                 175                 180

Phe Leu Arg Ala Glu Leu Asp Glu Leu Arg Gln Arg Glu Asp Thr
                185                 190                 195

Glu Lys Ala Gln Arg Ser Leu Ser Glu Ile Glu Arg Lys Ala Gln
                200                 205                 210

Ala Asn Glu Gln Arg Tyr Ser Lys Leu Lys Glu Lys Tyr Ser Glu
                215                 220                 225

Leu Val Gln Asn His Ala Asp Leu Leu Arg Lys Asn Ala Glu Val
                230                 235                 240

Thr Lys Gln Val Ser Met Ala Arg Gln Ala Gln Val Asp Leu Glu
                245                 250                 255

Arg Glu Lys Lys Glu Leu Glu Asp Ser Leu Glu Arg Ile Ser Asp
                260                 265                 270

Gln Gly Gln Arg Lys Thr Gln Glu Gln Leu Glu Val Leu Glu Ser
                275                 280                 285

Leu Lys Gln Glu Leu Gly Thr Ser Gln Arg Glu Leu Gln Val Leu
                290                 295                 300

Gln Gly Ser Leu Glu Thr Ser Ala Gln Ser Glu Ala Asn Trp Ala
```

```
                    305                 310                 315
Ala Glu Phe Ala Glu Leu Glu Lys Glu Arg Asp Ser Leu Val Ser
                320                 325                 330

Gly Ala Ala His Arg Glu Glu Leu Ser Ala Leu Arg Lys Glu
                335                 340                 345

Leu Gln Asp Thr Gln Leu Lys Leu Ala Ser Thr Glu Ser Met
                350                 355                 360

Cys Gln Leu Ala Lys Asp Gln Arg Lys Met Leu Leu Val Gly Ser
                365                 370                 375

Arg Lys Ala Ala Glu Gln Val Ile Gln Asp Ala
                380                 385

(2) INFORMATION FOR SEQ ID NO:3:

(i) SEQUENCE CHARACTERISTICS:
        (A) LENGTH: 4796
        (B) TYPE: nucleic acid
        (C) STRANDEDNESS: single
        (D) TOPOLOGY: linear (ii) MOLECULE TYPE: cDNA (iii) HYPOTHETICAL: no (iv) ANTI-SENSE: no (vi) ORIGINAL SOURCE:
         (A) ORGANISM: human (ix) FEATURE:
         (D) OTHER INFORMATION: cDNA for Huntington-interacting protein (xi) SEQUENCE DESCRIPTION: SEQ ID NO: 3:

CAGTGTACGG TTGATCATAT AACGCCGCGG GCGGGGATTG GTTTATATAT              50

CGCAAATTGA TNTAGGGGGG GGGGGATGGN CAGAGATTTC GCTTCATTAG             100

GCCATTATAA GCAGGAAGGG TTTCAAGGAA AAAAACCCAG AAAGTGCATA             150

TTGCACCCAC CATGAGAAAG GGCAACAGA CCTTNTGTTN TGTTNTCAAC              200

CGCCTGCTTC TGTTTTAGCA ACGCAGTGTT TTGGTGGAAG TTGTGCCATG             250

TGTTCCACAA ANTCTTCCGA GATGGACACC CGAACGTCCT GAAGGACTTT             300

GTGAGATACA GAAATGAATT GAGTGACATG AGCAGGATGT GGGGCCACCT             350

GAGCGAGGGG TATGGCCAGC TGTGCAGCAT CTACCTGAAA CTGCTAAGAA             400

CCAAGATGGA GTACCACACC AAAAATCCCA GGTTCCCAGG CAACCTGCAG             450

ATGAGTGACC GCCAGCTGGA CGAGGCTGGA GAAAGTGACG TGAACAACTT             500

TTTCCAGTTA ACAGTGGAGA TGTTTGACTA CCTGGAGTGT GAACTCAACC             550

TCTTCCAAAC AGTATTCAAC TCCCTGGACA TGTCCCGCTC TGTGTCCGTG             600

ACGGCAGCAG GGCAGTGCCG CCTCGCCCCG CTGATCCAGG TCATCTTGGA             650

CTGCAGCCAC CTTTATGACT ACACTGTCAA GCTTCTCTTC AAACTCCACT             700

CCTGCCTCCC AGCTGACACC CTGCAAGGCC ACCGGGACCG CTTCATGGAG             750

CAGTTTACAA AGTTGAAAGA TCTGTTCTAC CGCTCCAGCA ACCTGCAGTA             800

CTTCAAGCGG CTCATTCAGA TCCCCCAGCT GCCTGAGAAC CCACCCAACT             850

TCCTGCGAGC CTCAGCCCTG TCAGAACATA TCAGCCCTGT GGTGGTGATC             900

CCTGCAGAGG CCTCATCCCC CGACAGCGAG CCAGTCCTAG AGAAGGATGA             950

CCTCATGGAC ATGGATGCCT CTCAGCAGAA TTTATTTGAC AACAAGTTTG            1000
```

-continued

```
ATGACATCTT TGGCAGTTCA TTCAGCAGTG ATCCCTTCAA TTTCAACAGT        1050

CAAAATGGTG TGAACAAGGA TGAGAAGGAC CACTTAATTG AGCGACTATA        1100

CAGAGAGATC AGTGGATTGA AGGCACAGCT AGAAAACATG AAGACTGAGA        1150

GCCAGCGGGT TGTGCTGCAG CTGAAGGGCC ACGTCAGCGA GCTGGAAGCA        1200

GATCTGGCCG AGCAGCAGCA CCTGCGGCAG CAGGCGGCCG ACGACTGTGA        1250

ATTCCTGCGG GCAGAACTGG ACGAGCTCAG GAGGCAGCGG GAGGACACCG        1300

AGAAGGCTCA GCGGAGCCTG TCTGAGATAG AAAGGAAAGC TCAAGCCAAT        1350

GAACAGCGAT ATAGCAAGCT AAAGGAGAAG TACAGCGAGC TGGTTCAGAA        1400

CCACGCTGAC CTGCTGCGGA AGAATGCAGA GGTGACCAAA CAGGTGTCCA        1450

TGGCCAGACA AGCCCAGGTA GATTTGGAAC GAGAGAAAAA AGAGCTGGAG        1500

GATTCGTTGG AGCGCATCAG TGACCAGGGC CAGCGGAAGA CTCAAGAACA        1550

GCTGGAAGTT CTAGAGAGCT TGAAGCAGGA ACTTGGCACA AGCCAACGGG        1600

AGCTTCAGGT TCTGCAAGGC AGCCTGGAAA CTTCTGCCCA GTCAGAAGCA        1650

AACTGGGCAG CCGAGTTCGC CGAGCTAGAG AAGGAGCGGG ACAGCCTGGT        1700

GAGTGGCGCA GCTCATAGGG AGGAGGAATT ATCTGCTCTT CGGAAAGAAC        1750

TGCAGGACAC TCAGCTCAAA CTGGCCAGCA CAGAGGAATC TATGTGCCAG        1800

CTTGCCAAAG ACCAACGAAA AATGCTTCTG GTGGGGTCCA GGAAGGCTGC        1850

GGAGCAGGTG ATACAAGACG CCCTGAACCA GCTTGAAGAA CCTCCTCTCA        1900

TCAGCTGCGC TGGGTCTGCA GATCACCTCC TCTCCACGGT CACATCCATT        1950

TCCAGCTGCA TCGAGCAACT GGAGAAAAGC TGGAGCCAGT ATCTGGCCTG        2000

CCCAGAAGAC ATCAGTGGAC TTCTCCATTC CATAACCCTG CTGGCCCACT        2050

TGACCAGCGA CGCCATTGCT CATGGTGCCA CCACCTGCCT CAGAGCCCCA        2100

CCTGAGCCTG CCGACTCACT GACCGAGGCC TGTAAGCAGT ATGGCAGGGA        2150

AACCCTCGCC TACCTGGCCT CCCTGGAGGA AGAGGGAAGC CTTGAGAATG        2200

CCGACAGCAC AGCCATGAGG AACTGCCTGA GCAAGATCAA GGCCATCGGC        2250

GAGGAGCTCC TGCCCAGGGG ACTGGACATC AAGCAGGAGG AGCTGGGGGA        2300

CCTGGTGGAC AAGGAGATGG CGGCCACTTC AGCTGCTATT GAAACTTGCA        2350

CGGCCAGAAT AGAGGAGATG CTCAGCAAAT CCCGAGCAGG AGACACAGGA        2400

GTCAAATTGG AGGTGAATGA AAGGATCCTT CGTTGCTGTA CCAGCCTCAT        2450

GCAAGCTATT CAGGTGCTCA TCGTGGCCTC TAAGGACCTC CAGAGAGAGA        2500

TTGTGGAGAG CGGCAGGGGT ACAGCATCCC CTAAAGAGTT TTATGCCAAG        2550

AACTCTCGAT GGACAGAAGG ACTTATCTCA GCCTCCAAGG CTGTGGGCTG        2600

GGGAGCCACT GTCATGGTGG ATGCAGCTGA TCTGGTGGTA CAAGGCAGAG        2650

GGAAATTTGA GGAGCTAATG GTGTGTTCTC ATGAAATTGC TGCTAGCACA        2700

GCCCAGCTTG TGGCTGCATC CAAGGTGAAA GCTGATAAGG ACAGCCCCAA        2750

CCTAGCCCAG CTGCAGCAGG CCTCTCGGGG AGTGAACCAG GCCACTGCCG        2800

GCGTTGTGGC CTCAACCATT TCCGGCAAAT CACAGATCGA AGAGACAGAC        2850

AACATGGACT TCTCAAGCAT GACGCTGACA CAGATCAAAC GCCAAGAGAT        2900

GGATTCTCAG GTTAGGGTGC TAGAGCTAGA AAATGAATTG CAGAAGGAGC        2950
```

-continued

```
GTCAAAAACT GGGAGAGCTT CGGAAAAAGC ACTACGAGCT TGCTGGTGTT        3000

GCTGAGGGCT GGGAAGAAGG AACAGAGGCA TCTCCACCTA CACTGCAAGA        3050

AGTGGTAACC GAAAAAGAAT AGAGCCAAAC CAACACCCCA TATGTCAGTG        3100

TAAATCCTTG TTACCTATCT CGTGTGTGTT ATTTCCCCAG CCACAGGCCA        3150

AATCCTTGGA GTCCCAGGGG CAGCCACACC ACTGCCATTA CCCAGTGCCG        3200

AGGACATGCA TGACACTTCC CAAAGATCCC TCCATAGCGA CACCCTTTCT        3250

GTTTGGACCC ATGGTCATCT CTGTTCTTTT CCCGCCTCCC TAGTTAGCAT        3300

CCAGGCTGGC CAGTGCTGCC CATGAGCAAG CCTAGGTACG AAGAGGGGTG        3350

GTGGGGGGCA GGGCCACTCA ACAGAGAGGA CCAACATCCA GTCCTGCTGA        3400

CTATTTGACC CCCACAACAA TGGGTATCCT TAATAGAGGA GCTGCTTGTT        3450

GTTTGTTGAC AGCTTGGAAA GGGAAGATCT TATGCCTTTT CTTTTCTGTT        3500

TTCTTCTCAG TCTTTTCAGT TTCATCATTT GCACAAACTT GTGAGCATCA        3550

GAGGGCTGAT GGATTCCAAA CCAGGACACT ACCCTGAGAT CTGCACAGTC        3600

AGAAGGACGG CAGGAGTGTC CTGGCTGTGA ATGCCAAAGC CATTCTCCCC        3650

CTCTTTGGGC AGTGCCATGG ATTTCCACTG CTTCTTATGG TGGTTGGTTG        3700

GGTTTTTTGG TTTTGTTTTT TTTTTTAAG TTTCACTCAC ATAGCCAACT         3750

CTCCCAAAGG GCACACCCCT GGGGCTGAGT CTCCAGGGCC CCCCAACTGT        3800

GGTAGCTCCA GCGATGGTGC TGCCCAGGCC TCTCGGTGCT CCATCTCCGC        3850

CTCCACACTG ACCAAGTGCT GGCCCACCCA GTCCATGCTC CAGGGTCAGG        3900

CGGAGCTGCT GAGTGACAGC TTTCCTCAAA AGCAGAAGG AGAGTGAGTG         3950

CCTTTCCCTC CTAAAGCTGA ATCCCGGCGG AAAGCCTCTG TCCGCCTTTA        4000

CAAGGGAGAA GACAACAGAA AGAGGACAA GAGGGTTCAC ACAGCCCAGT         4050

TCCCGTGACG AGGCTCAAAA ACTTGATCAC ATGCTTGAAT GGAGCTGGTG        4100

AGATCAACAA CACTACTTCC CTGCCGGAAT GAACTGTCCG TGAATGGTCT        4150

CTGTCAAGCG GGCCGTCTCC CTTGGCCCAG AGACGGAGTG TGGGAGTGAT        4200

TCCCAACTCC TTTCTGCAGA CGTCTGCCTT GGCATCCTCT TGAATAGGAA        4250

GATCGTTCCA CTTTCTACGC AATTGACAAA CCCGGAAGAT CAGATGCAAT        4300

TGCTCCCATC AGGGAAGAAC CCTATACTTG GTTTGCTACC CTTAGTATTT        4350

ATTACTAACC TCCCTTAAGC AGCAACAGCC TACAAAGAGA TGCTTGGAGC        4400

AATCAGAACT TCAGGTGTGA CTCTAGCAAA GCTCATCTTT CTGCCCGGCT        4450

ACATCAGCCT TCAAGAATCA GAAGAAAGCC AAGGTGCTGG ACTGTTACTG        4500

ACTTGGATCC CAAAGCAAGG AGATCATTTG GAGCTCTTGG GTCAGAGAAA        4550

ATGAGAAAGG ACAGAGCCAG CGGCTCCAAC TCCTTTCAGC CACATGCCCC        4600

AGGCTCTCGC TGCCCTGTGG ACAGGATGAG GACAGAGGGC ACATGAACAG        4650

CTTGCCAGGG ATGGGCAGCC AACAGCACT TTTCCTCTTC TAGATGGACC         4700

CCAGCATTTA AGTGACCTTC TGATCTTGGG AAAACAGCGT CTTCCTTCTT        4750

TATCTATAGC AACTCATTGG TGGTAGCCAT CAAGCACTTC GGAATT           4796
```

(2) INFORMATION FOR SEQ ID NO: 4:

(i) SEQUENCE CHARACTERISTICS:
        (A) LENGTH: 914

(B) TYPE: amino acid
            (D) TOPOLOGY: linear (ii) MOLECULE TYPE: protein (iii) HYPOTHETICAL: no (vi) ORIGINAL SOURCE:
          (A) ORGANISM: human (ix) FEATURE: Huntington-interacting protein (xi) SEQUENCE DESCRIPTION: SEQ ID NO: 4:

```
Met Ser Arg Met Trp Gly His Leu Ser Glu Gly Tyr Gly Gln Leu
 1               5                  10                  15

Cys Ser Ile Tyr Leu Lys Leu Leu Arg Thr Lys Met Glu Tyr His
                20                  25                  30

Thr Lys Asn Pro Arg Phe Pro Gly Asn Leu Gln Met Ser Asp Arg
                35                  40                  45

Gln Leu Asp Glu Ala Gly Glu Ser Asp Val Asn Asn Phe Phe Gln
                50                  55                  60

Leu Thr Val Glu Met Phe Asp Tyr Leu Glu Cys Glu Leu Asn Leu
                65                  70                  75

Phe Gln Thr Val Phe Asn Ser Leu Asp Met Ser Arg Ser Val Ser
                80                  85                  90

Val Thr Ala Ala Gly Gln Cys Arg Leu Ala Pro Leu Ile Gln Val
                95                 100                 105

Ile Leu Asp Cys Ser His Leu Tyr Asp Tyr Thr Val Lys Leu Leu
               110                 115                 120

Phe Lys Leu His Ser Cys Leu Pro Ala Asp Thr Leu Gln Gly His
               125                 130                 135

Arg Asp Arg Phe Met Glu Gln Phe Thr Lys Leu Lys Asp Leu Phe
               140                 145                 150

Tyr Arg Ser Ser Asn Leu Gln Tyr Phe Lys Arg Leu Ile Gln Ile
               155                 160                 165

Pro Gln Leu Pro Glu Asn Pro Asn Phe Leu Arg Ala Ser Ala
               170                 175                 180

Leu Ser Glu His Ile Ser Pro Val Val Ile Pro Ala Glu Ala
               185                 190                 195

Ser Ser Pro Asp Ser Glu Pro Val Leu Glu Lys Asp Leu Met
               200                 205                 210

Asp Met Asp Ala Ser Gln Gln Asn Leu Phe Asp Asn Lys Phe Asp
               215                 220                 225

Asp Ile Phe Gly Ser Ser Phe Ser Ser Asp Pro Phe Asn Phe Asn
               230                 235                 240

Ser Gln Asn Gly Val Asn Lys Asp Glu Lys Asp His Leu Ile Glu
               245                 250                 255

Arg Leu Tyr Arg Glu Ile Ser Gly Leu Lys Ala Gln Leu Glu Asn
               260                 265                 270

Met Lys Thr Glu Ser Gln Arg Val Val Leu Gln Leu Lys Gly His
               275                 280                 285

Val Ser Glu Leu Glu Ala Asp Leu Ala Glu Gln Gln His Leu Arg
               290                 295                 300

Gln Gln Ala Ala Asp Asp Cys Glu Phe Leu Arg Ala Glu Leu Asp
               305                 310                 315

Glu Leu Arg Arg Gln Arg Glu Asp Thr Glu Lys Ala Gln Arg Ser
               320                 325                 330
```

-continued

```
Leu Ser Glu Ile Glu Arg Lys Ala Gln Ala Asn Glu Gln Arg Tyr
            335                 340                 345
Ser Lys Leu Lys Glu Lys Tyr Ser Glu Leu Val Gln Asn His Ala
            350                 355                 360
Asp Leu Leu Arg Lys Asn Ala Glu Val Thr Lys Gln Val Ser Met
            365                 370                 375
Ala Arg Gln Ala Gln Val Asp Leu Glu Arg Glu Lys Lys Glu Leu
            380                 385                 390
Glu Asp Ser Leu Glu Arg Ile Ser Asp Gln Gly Gln Arg Lys Thr
            395                 400                 405
Gln Glu Gln Leu Glu Val Leu Glu Ser Leu Lys Gln Glu Leu Gly
            410                 415                 420
Thr Ser Gln Arg Glu Leu Gln Val Leu Gln Gly Ser Leu Glu Thr
            425                 430                 435
Ser Ala Gln Ser Glu Ala Asn Trp Ala Ala Glu Phe Ala Glu Leu
            440                 445                 450
Glu Lys Glu Arg Asp Ser Leu Val Ser Gly Ala Ala His Arg Glu
            455                 460                 465
Glu Glu Leu Ser Ala Leu Arg Lys Glu Leu Gln Asp Thr Gln Leu
            470                 475                 480
Lys Leu Ala Ser Thr Glu Glu Ser Met Cys Gln Leu Ala Lys Asp
            485                 490                 495
Gln Arg Lys Met Leu Leu Val Gly Ser Arg Lys Ala Ala Glu Gln
            500                 505                 510
Val Ile Gln Asp Ala Leu Asn Gln Leu Glu Glu Pro Pro Leu Ile
            515                 520                 525
Ser Cys Ala Gly Ser Ala Asp His Leu Leu Ser Thr Val Thr Ser
            530                 535                 540
Ile Ser Ser Cys Ile Glu Gln Leu Glu Lys Ser Trp Ser Gln Tyr
            545                 550                 555
Leu Ala Cys Pro Glu Asp Ile Ser Gly Leu Leu His Ser Ile Thr
            560                 565                 570
Leu Leu Ala His Leu Thr Ser Asp Ala Ile Ala His Gly Ala Thr
            575                 580                 585
Thr Cys Leu Arg Ala Pro Pro Glu Pro Ala Asp Ser Leu Thr Glu
            590                 595                 600
Ala Cys Lys Gln Tyr Gly Arg Gly Thr Leu Ala Tyr Leu Ala Ser
            605                 610                 615
Leu Glu Glu Glu Gly Ser Leu Glu Asn Ala Asp Ser Thr Ala Met
            620                 625                 630
Arg Asn Cys Leu Ser Lys Ile Lys Ala Ile Gly Glu Glu Leu Leu
            635                 640                 645
Pro Arg Gly Leu Asp Ile Lys Gln Glu Glu Leu Gly Asp Leu Val
            650                 655                 660
Asp Lys Glu Met Ala Ala Thr Ser Ala Ala Ile Glu Thr Cys Thr
            665                 670                 675
Ala Arg Ile Glu Glu Met Leu Ser Lys Ser Arg Ala Gly Asp Thr
            680                 685                 690
Gly Val Lys Leu Glu Val Asn Glu Arg Ile Leu Arg Cys Cys Thr
            695                 700                 705
Ser Leu Met Gln Ala Ile Gln Val Leu Ile Val Ala Ser Lys Asp
            710                 715                 720
```

```
Leu Gln Arg Glu Ile Val Glu Ser Gly Arg Gly Thr Ala Ser Pro
                725                 730                 735

Lys Glu Phe Tyr Ala Lys Asn Ser Arg Trp Thr Glu Gly Leu Ile
                740                 745                 750

Ser Ala Ser Lys Ala Val Gly Trp Gly Ala Thr Val Met Val Asp
                755                 760                 765

Ala Ala Asp Leu Val Val Gln Gly Arg Gly Lys Phe Glu Glu Leu
                770                 775                 780

Met Val Cys Ser His Glu Ile Ala Ala Ser Thr Ala Gln Leu Val
                785                 790                 795

Ala Ala Ser Lys Val Lys Ala Asp Lys Asp Ser Pro Asn Leu Ala
                800                 805                 810

Gln Leu Gln Gln Ala Ser Arg Gly Val Asn Gln Ala Thr Ala Gly
                815                 820                 825

Val Val Ala Ser Thr Ile Ser Gly Lys Ser Gln Ile Glu Glu Thr
                830                 835                 840

Asp Asn Met Asp Phe Ser Ser Met Thr Leu Thr Gln Ile Lys Arg
                845                 850                 855

Gln Glu Met Asp Ser Gln Val Arg Val Leu Glu Leu Glu Asn Glu
                860                 865                 870

Leu Gln Lys Glu Arg Gln Lys Leu Gly Glu Leu Arg Lys Lys His
                875                 880                 885

Tyr Glu Leu Ala Gly Val Ala Glu Gly Trp Glu Glu Gly Thr Glu
                890                 895                 900

Ala Ser Pro Pro Thr Leu Gln Glu Val Val Thr Glu Lys Glu
                905                 910                 914

(2) INFORMATION FOR SEQ ID NO:5:

(i) SEQUENCE CHARACTERISTICS:
        (A) LENGTH: 1090
        (B) TYPE: amino acid
        (D) TOPOLOGY: linear (ii) MOLECULE TYPE: protein (iii) HYPOTHETICAL: no (vi) ORIGINAL SOURCE:
        (A) ORGANISM: human (ix) FEATURE:
        (D) OTHER INFORMATION: Huntington-interacting protein (xi) SEQUENCE DESCRIPTION: SEQ ID NO: 5:

Met Leu Leu Cys Gln Gly Ser Glu Trp Arg Arg Asp Gln Gln Leu
                 5                  10                  15

Gly Thr Ala Asn Ala Arg Gln Trp Cys Pro Leu Pro Gln Asp Ala
                20                  25                  30

Gln Pro Ala Gly Ser Trp Glu Arg Cys Pro Pro Leu Pro Pro Ala
                35                  40                  45

Gly Arg Leu Gln Gly Thr Asp His Pro Trp Gly Trp Gly Arg Leu
                50                  55                  60

Ala Gly Gly Gly Glu Arg Gly Gly Leu Trp Glu Gly Leu Ser His
                65                  70                  75

Ser Gln Arg Leu Ile His Leu Ile Leu Leu Ser Leu Pro Leu Leu
                80                  85                  90

Val Phe Gln Thr Val Ser Ile Asn Lys Ala Ile Asn Thr Gln Glu
                95                 100                 105
```

-continued

```
Val Ala Val Lys Glu Lys His Ala Arg Thr Cys Ile Leu Gly Thr
            110                 115                 120

His His Glu Lys Gly Ala Gln Thr Phe Trp Ser Val Val Asn Arg
            125                 130                 135

Leu Pro Leu Ser Ser Asn Ala Val Leu Cys Trp Lys Phe Cys His
            140                 145                 150

Val Phe His Lys Leu Leu Arg Asp Gly His Pro Asn Val Leu Lys
            155                 160                 165

Asp Ser Leu Arg Tyr Arg Asn Glu Leu Ser Asp Met Ser Arg Met
            170                 175                 180

Trp Gly His Leu Ser Glu Gly Tyr Gly Gln Leu Cys Ser Ile Tyr
            185                 190                 195

Leu Lys Leu Leu Arg Thr Lys Met Glu Tyr His Thr Lys Asn Pro
            200                 205                 210

Arg Phe Pro Gly Asn Leu Gln Met Ser Asp Arg Gln Leu Asp Glu
            215                 220                 225

Ala Gly Glu Ser Asp Val Asn Asn Phe Phe Gln Leu Thr Val Glu
            230                 235                 240

Met Phe Asp Tyr Leu Glu Cys Glu Leu Asn Leu Phe Gln Thr Val
            245                 250                 255

Phe Asn Ser Leu Asp Met Ser Arg Ser Val Ser Val Thr Ala Ala
            260                 265                 270

Gly Gln Cys Arg Leu Ala Pro Leu Ile Gln Val Ile Leu Asp Cys
            275                 288                 285

Ser His Leu Tyr Asp Tyr Thr Val Lys Leu Leu Phe Lys Leu His
            290                 295                 300

Ser Cys Leu Pro Ala Asp Thr Leu Gln Gly His Arg Asp Arg Phe
            305                 310                 315

Met Glu Gln Phe Thr Lys Leu Lys Asp Leu Phe Tyr Arg Ser Ser
            320                 325                 330

Asn Leu Gln Tyr Phe Lys Arg Leu Ile Gln Ile Pro Gln Leu Pro
            335                 340                 345

Glu Asn Pro Pro Asn Phe Leu Arg Ala Ser Ala Leu Ser Glu His
            350                 355                 360

Ile Ser Pro Val Val Ile Pro Ala Glu Ala Ser Ser Pro Asp
            365                 370                 375

Ser Glu Pro Val Leu Glu Lys Asp Asp Leu Met Asp Met Asp Ala
            380                 385                 390

Ser Gln Gln Asn Leu Phe Asp Asn Lys Phe Asp Asp Ile Phe Gly
            395                 400                 405

Ser Ser Phe Ser Ser Asp Pro Phe Asn Phe Asn Ser Gln Asn Gly
            410                 415                 420

Val Asn Lys Asp Glu Lys Asp His Leu Ile Glu Arg Leu Tyr Arg
            425                 430                 435

Glu Ile Ser Gly Leu Lys Ala Gln Leu Glu Asn Met Lys Thr Glu
            440                 445                 450

Ser Gln Arg Val Val Leu Gln Leu Lys Gly His Val Ser Glu Leu
            455                 460                 465

Glu Ala Asp Leu Ala Glu Gln His Leu Arg Gln Ala Ala
            470                 475                 480

Asp Asp Cys Glu Phe Leu Arg Ala Glu Leu Asp Glu Leu Arg Arg
            485                 490                 495
```

```
Gln Arg Glu Asp Thr Glu Lys Ala Gln Arg Ser Leu Ser Glu Ile
                500                 505                 510

Glu Arg Lys Ala Gln Ala Asn Glu Gln Arg Tyr Ser Lys Leu Lys
            515                 520                 525

Glu Lys Tyr Ser Glu Leu Val Gln Asn His Ala Asp Leu Leu Arg
        530                 535                 540

Lys Asn Ala Glu Val Thr Lys Gln Val Ser Met Ala Arg Gln Ala
    545                 550                 555

Gln Val Asp Leu Glu Arg Glu Lys Lys Glu Leu Glu Asp Ser Leu
560                 565                 570

Glu Arg Ile Ser Asp Gln Gly Gln Arg Lys Thr Gln Glu Gln Leu
                575                 588                 585

Glu Val Leu Glu Ser Leu Lys Gln Glu Leu Ala Thr Ser Gln Arg
            590                 595                 600

Glu Leu Gln Val Leu Gln Gly Ser Leu Glu Thr Ser Ala Gln Ser
        605                 610                 615

Glu Ala Asn Trp Ala Ala Glu Phe Ala Glu Leu Glu Lys Glu Arg
    620                 625                 630

Asp Ser Leu Val Ser Gly Ala Ala His Arg Glu Glu Glu Leu Ser
635                 640                 645

Ala Leu Arg Lys Glu Leu Gln Asp Thr Gln Leu Lys Leu Ala Ser
                650                 655                 660

Thr Glu Glu Ser Met Cys Gln Leu Ala Lys Asp Gln Arg Lys Met
            665                 670                 675

Leu Leu Val Gly Ser Arg Lys Ala Ala Glu Gln Val Ile Gln Asp
        680                 685                 690

Ala Leu Asn Gln Leu Glu Glu Pro Pro Leu Ile Ser Cys Ala Gly
    695                 700                 705

Ser Ala Asp His Leu Leu Ser Thr Val Thr Ser Ile Ser Ser Cys
710                 715                 720

Ile Glu Gln Leu Glu Lys Ser Trp Ser Gln Tyr Leu Ala Cys Pro
                725                 730                 735

Glu Asp Ile Ser Gly Leu Leu His Ser Ile Thr Leu Leu Ala His
            740                 745                 750

Leu Thr Ser Asp Ala Ile Ala His Gly Ala Thr Thr Cys Leu Arg
        755                 760                 765

Ala Pro Pro Glu Pro Ala Asp Ser Leu Thr Glu Ala Cys Lys Gln
    770                 775                 780

Tyr Gly Arg Glu Thr Leu Ala Tyr Leu Ala Ser Leu Glu Glu Glu
785                 790                 795

Gly Ser Leu Glu Asn Ala Asp Ser Thr Ala Met Arg Asn Cys Leu
                800                 805                 810

Ser Lys Ile Lys Ala Ile Gly Glu Glu Leu Leu Pro Arg Gly Leu
            815                 820                 825

Asp Ile Lys Gln Glu Glu Leu Gly Asp Leu Val Asp Lys Glu Met
        830                 835                 840

Ala Ala Thr Ser Ala Ala Ile Glu Thr Ala Thr Ala Arg Ile Glu
    845                 850                 855

Glu Met Leu Ser Lys Ser Arg Ala Gly Asp Thr Gly Val Lys Leu
860                 865                 870

Glu Val Asn Glu Arg Ile Leu Gly Cys Cys Thr Ser Leu Met Gln
                875                 888                 885

Ala Ile Gln Val Leu Ile Val Ala Ser Lys Asp Leu Gln Arg Glu
```

```
                    890                 895                 900
Ile Val Glu Ser Gly Arg Gly Thr Ala Ser Pro Lys Glu Phe Tyr
                905                 910                 915

Ala Lys Asn Ser Arg Trp Thr Glu Gly Leu Ile Ser Ala Ser Lys
                920                 925                 930

Ala Val Gly Trp Gly Ala Thr Val Met Val Asp Ala Ala Asp Leu
                935                 940                 945

Val Val Gln Gly Arg Gly Lys Phe Glu Glu Leu Met Val Cys Ser
                950                 955                 960

His Glu Ile Ala Ala Ser Thr Ala Gln Leu Val Ala Ala Ser Lys
                965                 970                 975

Val Lys Ala Asp Lys Asp Ser Pro Asn Leu Ala Gln Leu Gln Gln
                980                 985                 990

Ala Ser Arg Gly Val Asn Gln Ala Thr Ala Gly Val Val Ala Ser
                995                1000                1005

Thr Ile Ser Gly Lys Ser Gln Ile Glu Glu Thr Asp Asn Met Asp
               1010                1015                1020

Phe Ser Ser Met Thr Leu Thr Gln Ile Lys Arg Gln Glu Met Asp
               1025                1030                1035

Ser Gln Val Arg Val Leu Glu Leu Glu Asn Glu Leu Gln Lys Glu
               1040                1045                1050

Arg Gln Lys Leu Gly Glu Leu Arg Lys Lys His Tyr Glu Leu Ala
               1055                1060                1065

Gly Val Ala Glu Gly Trp Glu Glu Gly Thr Glu Ala Ser Pro Pro
               1070                1075                1080

Thr Leu Gln Glu Val Val Thr Glu Lys Glu
               1085                1090

(2) INFORMATION FOR SEQ ID NO:6:

(i) SEQUENCE CHARACTERISTICS:
        (A) LENGTH: 3251
        (B) TYPE: nucleic acid
        (C) STRANDEDNESS: single
        (D) TOPOLOGY: linear (ii) MOLECULE TYPE: cDNA (iii) HYPOTHETICAL: no (iv) ANTI-SENSE: no (vi) ORIGINAL SOURCE:
        (A) ORGANISM: human (ix) FEATURE:
        (D) OTHER INFORMATION: cDNA for Huntington-interacting protein (xi) SEQUENCE DESCRIPTION: SEQ ID NO: 6:

CGGTGAGCTG GAGGAGCAGC GGAAGCAGAA GCAGAAGGCC CTGGTGGATA           50

ATGAGCAGCT CCGCCACGAG CTGGCCCAGC TGAGGGCTGC CCAGCTGGAG          100

CGCGAGCGGA GCCAGGGCCT GCGTGAGGAG GCTGAGAGGA AGGCCAGTGC          150

CACGGAGGCG CGCTACAACA AGCTGAAGGA AAAGCACAGT GAGCTCGTCC          200

ATGTGCACGC GGAGCTGCTC AGAAAGAACG CGGACACAGC CAAGCAGCTG          250

ACGGTGACGC AGCAAAGCCA GGAGGAGGTG GCGCGGGTGA AGGAGCAGCT          300

GGCCTTCCAG GTGGAGCAGG TGAAGCGGGA GTCGGAGTTG AAGCTAGAGG          350

AGAAGAGCGA CCAGCAGGAG AAGCTCAAGA GGGAGCTGGA GGCCAAGGCC          400
```

```
GGAGAGCTGG CCCGCGCGCA GGAGGCCCTG AGCCACACAG AGCAGAGCAA         450

GTCGGAGCTG AGCTCACGGC TGGACACACT GAGTGCGGAG AAGGATGCTC         500

TGAGTGGAGC TGTGCGGCAG CGGGAGGCAG ACCTGCTGGC GGCGCAGAGC         550

CTGGTGCGCG AGACAGAGGC GGCGCTGAGC CGGGAGCAGC AGCGCAGCTC         600

CCAGGAGCAG GGCGAGTTGC AGGGCCGGCT GGCAGAGAGG GAGTCTCAGG         650

AGCAGGGGCT GCGGCAGAGG CTGCTGGACG AGCAGTTCGC AGTGTTGCGG         700

GGCGCTGCTG CCGAGGCCGC GGGCATCCTG CAGGATGCCG TGAGCAAGCT         750

GGACGACCCC CTGCACCTGC GCTGTACCAG CTCCCCAGAC TACCTGGTGA         800

GCAGGGCCCA GGAGGCCTTG GATGCCGTGA GCACCCTGGA GGAGGGCCAC         850

GCCCAGTACC TGACCTCCTT GGCAGACGCC TCCGCCCTGG TGGCAGCTCT         900

GACCCGCTTC TCCCACCTGG CTGCGGATAC CATCATCAAT GGCGGTGCCA         950

CCTCGCACCT GGCTCCCACC GACCCTGCCG ACCGCCTCAT AGACACCTGC         1000

AGGGAGTGCG GGGCCCGGGC TCTGGAGCTC ATGGGGCAGC TGCAGGACCA         1050

GCAGGCTCTG CGGCACATGC AGGCCAGCCT GGTGCGGACA CCCCTGCAGG         1100

GCATCCTTCA GCTGGGCCAA GAACTGAAAC CCAAGAGCCT AGATGTGCGG         1150

CAGGAGGAGC TGGGGGCCGT GGTCGACAAG GAGATGGCGG CCACATCCGC         1200

AGCCATTGAA GATGCTGTGC GGAGGATTGA GGACATGATG AACCAGGCAC         1250

GCCACGCCAG CTCGGGGGTG AAGCTGGAGG TGAACGAGAG GATCCTCAAC         1300

TCCTGCACAG ACCTGATGAA GGCTATCCGG CTCCTGGTGA CGACATCCAC         1350

TAGCCTGCAG AAGGAGATCG TGGAGAGCGG CAGGGGGGCA GCCACGCAGC         1400

AGGAATTTTA CGCCAAGAAC TCGCGCTGGA CCGAAGGCCT CATCTCGGCC         1450

TCCAAGGCTG TGGGCTGGGG AGCCACACAG CTGGTGGAGG CAGCTGACAA         1500

GGTGGTGCTT CACACGGGCA AGTATGAGGA GCTCATCGTC TGCTCCCACG         1550

AGATCGCAGC CAGCACGGCC CAGCTGGTGG CGGCCTCCAA GGTGAAGGCC         1600

AACAAGCACA GCCCCCACCT GAGCCGCCTG CAGGAATGTT CTCGCACAGT         1650

CAATGAGAGG GCTGCCAATG TGGTGGCCTC CACCAAGTCA GGCCAGGAGC         1700

AGATTGAGGA CAGAGACACC ATGGATTTCT CCGGCCTGTC CCTCATCAAG         1750

CTGAAGAAGC AGGAGATGGA GACGCAGGTG CGTGTCCTGG AGCTGGAGAA         1800

GACGCTGGAG GCTGAACGCA TGCGGCTGGG GGAGTTGCGG AAGCAACACT         1850

ACGTGCTGGC TGGGGCATCA GGCAGCCCTG GAGAGGAGGT GGCCATCCGG         1900

CCCAGCACTG CCCCCCGAAG TGTAACCACC AAGAAACCAC CCCTGGCCCA         1950

GAAGCCCAGC GTGGCCCCCA GACAGGACCA CCAGCTTGAC AAAAAGGATG         2000

GCATCTACCC AGCTCAACTC GTGAACTACT AGGCCCCCCA GGGGTCCAGC         2050

AGGGTGGCTG GTGACAGGCC TGGGCCTCTG CAACTGCCCT GACAGGACCG         2100

AGAGGCCTTG CCCCTCCACC TGGTGCCCAA GCCTCCCGCC CCACCGTCTG         2150

GATCAATGTC CTCAAGGCCC CTGGCCCTTA CTGAGCCTGC AGGGTCCTGG         2200

GCCATGTGGG TGGTGCTTCT GGATGTGAGT CTCTTATTTA TCTGCAGAAG         2250

GAACTTTGGG GTGCAGCCAG GACCCGGTAG GCCTGAGCCT CAACTCTTCA         2300

GAAAATAGTG TTTTTAATAT TCCTCTTCAG AAAATAGTGT TTTTAATATT         2350
```

```
CCGAGCTAGA GCTCTTCTTC CTACGTTTGT AGTCAGCACA CTGGGAAACC        2400
GGGCCAGCGT GGGGCTCCCT GCCTTCTGGA CTCCTGAAGG TCGTGGATGG        2450
ATGGAAGGCA CACAGCCCGT GCCGGCTGAT GGGACGAGGG TCAGGCATCC        2500
TGTCTGTGGC CTTCTGGGGC ACCGATTCTA CCAGGCCCTC CAGCTGCGTG        2550
GTCTCCGCAG ACCAGGCTCT GTGTGGGCTA GAGGAATGTC GCCCATTACC        2600
TCCTCAGGCC CTGGCCCTCG GGCCTCCGTG ATGGGAGCCC CCAGGAGGG         2650
GTCAGATGCT GGAAGGGGCC GCTTTCTGGG GAGTGAGGTG AGACATAGCG        2700
GCCCAGGCGC TGCCTTCACT CCTGGAGTTT CCATTTCCAG CTGGAATCTG        2750
CAGCCACCCC CATTTCCTGT TTTCCATTCC CCCGTTCTGG CCGCGCCCCA        2800
CTGCCCACCT GAAGGGGTGG TTTCCAGCCC TCCGGAGAGT GGGCTTGGCC        2850
CTAGGCCCTC CAGCTCAGCC AGAAAAAGCC CAGAAACCCA GGTGCTGGAC        2900
CAGGGCCCTC AGGGAGGGAC CCTGCGGCTA GAGTGGGCTA GGCCCTGGCT        2950
TTGCCCGTCA GATTTGAACG AATGTGTGTC CCTTGAGCCC AAGGAGAGCG        3000
GCAGGAGGGG TGGGACCAGG CTGGGAGGAC AGAGCCAGCA GCTGCCATGC        3050
CCTCCTGCTC CCCCCACCCC AGCCCTAGCC CTTTAGCCTT TCACCCTGTG        3100
CTCTGGAAAG GCTACCAAAT ACTGGCCAAG GTCAGGAGGA GCAAAAATGA        3150
GCCAGCACCA GCGCCTTGGC TTTGTGTTAG CATTTCCTCC TGAAGTGTTC        3200
TGTTGGCAAT AAAATGCACT TTGACTGTTA AAAAAAAAAA AAAAAAAAA        3250
A                                                            3251
```

(2) INFORMATION FOR SEQ ID NO:7:

(i) SEQUENCE CHARACTERISTICS:
        (A) LENGTH: 676
        (B) TYPE: amino acid
        (D) TOPOLOGY: linear (ii) MOLECULE TYPE: protein (iii) HYPOTHETICAL: no (vi) ORIGINAL SOURCE:
        (A) ORGANISM: human (ix) FEATURE:
        (D) OTHER INFORMATION: Huntington-interacting protein (xi) SEQUENCE DESCRIPTION: SEQ ID NO: 7:

```
Gly Glu Leu Glu Glu Gln Arg Lys Gln Lys Gln Lys Ala Leu Val
                 5                  10                  15

Asp Asn Glu Gln Leu Arg His Glu Leu Ala Gln Leu Arg Ala Ala
                20                  25                  30

Gln Leu Glu Arg Glu Arg Ser Gln Gly Leu Arg Glu Glu Ala Glu
                35                  40                  45

Arg Lys Ala Ser Ala Thr Glu Ala Arg Tyr Asn Lys Leu Lys Glu
                50                  55                  60

Lys His Ser Glu Leu Val His Val His Ala Glu Leu Leu Arg Lys
                65                  70                  75

Asn Ala Asp Thr Ala Lys Gln Leu Thr Val Thr Gln Ser Gln
                80                  85                  90

Glu Glu Val Ala Arg Val Lys Glu Gln Leu Ala Phe Gln Val Glu
                95                 100                 105
```

```
Gln Val Lys Arg Glu Ser Glu Leu Lys Leu Glu Glu Lys Ser Asp
            110                 115                 120

Gln Gln Glu Lys Leu Lys Arg Glu Leu Glu Ala Lys Ala Gly Glu
            125                 130                 135

Leu Ala Arg Ala Gln Glu Ala Leu Ser His Thr Gln Ser Lys
            140                 145                 150

Ser Glu Leu Ser Ser Arg Leu Asp Thr Leu Ser Ala Glu Lys Asp
            155                 160                 165

Ala Leu Ser Gly Ala Val Arg Gln Arg Glu Ala Asp Leu Leu Ala
            170                 175                 180

Ala Gln Ser Leu Val Arg Glu Thr Glu Ala Ala Leu Ser Arg Glu
            185                 190                 195

Gln Gln Arg Ser Ser Gln Glu Gln Gly Glu Leu Gln Gly Arg Leu
            200                 205                 210

Ala Glu Arg Glu Ser Gln Glu Gln Gly Leu Arg Gln Arg Leu Leu
            215                 220                 225

Asp Glu Gln Phe Ala Val Leu Arg Gly Ala Ala Glu Ala Ala
            230                 235                 240

Gly Ile Leu Gln Asp Ala Val Ser Lys Leu Asp Asp Pro Leu His
            245                 250                 255

Leu Arg Cys Thr Ser Ser Pro Asp Tyr Leu Val Ser Arg Ala Gln
            260                 265                 270

Glu Ala Leu Asp Ala Val Ser Thr Leu Glu Glu Gly His Ala Gln
            275                 288                 285

Tyr Leu Thr Ser Leu Ala Asp Ala Ser Ala Leu Val Ala Ala Leu
            290                 295                 300

Thr Arg Phe Ser His Leu Ala Ala Asp Thr Ile Ile Asn Gly Gly
            305                 310                 315

Ala Thr Ser His Leu Ala Pro Thr Asp Pro Ala Asp Arg Leu Ile
            320                 325                 330

Asp Thr Cys Arg Glu Cys Gly Ala Arg Ala Leu Glu Leu Met Gly
            335                 340                 345

Gln Leu Gln Asp Gln Gln Ala Leu Arg His Met Gln Ala Ser Leu
            350                 355                 360

Val Arg Thr Pro Leu Gln Gly Ile Leu Gln Leu Gly Gln Glu Leu
            365                 370                 375

Lys Pro Lys Ser Leu Asp Val Arg Gln Glu Glu Leu Gly Ala Val
            380                 385                 390

Val Asp Lys Glu Met Ala Ala Thr Ser Ala Ala Ile Glu Asp Ala
            395                 400                 405

Val Arg Arg Ile Glu Asp Met Met Asn Gln Ala Arg His Ala Ser
            410                 415                 420

Ser Gly Val Lys Leu Glu Val Asn Glu Arg Ile Leu Asn Ser Cys
            425                 430                 435

Thr Asp Leu Met Lys Ala Ile Arg Leu Leu Val Thr Thr Ser Thr
            440                 445                 450

Ser Leu Gln Lys Glu Ile Val Glu Ser Gly Arg Gly Ala Ala Thr
            455                 460                 465

Gln Gln Glu Phe Tyr Ala Lys Asn Ser Arg Trp Thr Glu Gly Leu
            470                 475                 480

Ile Ser Ala Ser Lys Ala Val Gly Trp Gly Ala Thr Gln Leu Val
            485                 490                 495

Glu Ala Ala Asp Lys Val Val Leu His Thr Gly Lys Tyr Glu Glu
```

```
                    500              505              510
Leu Ile Val Cys Ser His Glu Ile Ala Ala Ser Thr Ala Gln Leu
                515                  520                  525
Val Ala Ala Ser Lys Val Lys Ala Asn Lys His Ser Pro His Leu
                530                  535                  540
Ser Arg Leu Gln Glu Cys Ser Arg Thr Val Asn Glu Arg Ala Ala
                545                  550                  555
Asn Val Val Ala Ser Thr Lys Ser Gly Gln Glu Gln Ile Glu Asp
                560                  565                  570
Arg Asp Thr Met Asp Phe Ser Gly Leu Ser Leu Ile Lys Leu Lys
                575                  588                  585
Lys Gln Glu Met Glu Thr Gln Val Arg Val Leu Glu Leu Glu Lys
                590                  595                  600
Thr Leu Glu Ala Glu Arg Met Arg Leu Gly Glu Leu Arg Lys Gln
                605                  610                  615
His Tyr Val Leu Ala Gly Ala Ser Gly Ser Pro Gly Glu Val
                620                  625                  630
Ala Ile Arg Pro Ser Thr Ala Pro Arg Ser Val Thr Thr Lys Lys
                635                  640                  645
Pro Pro Leu Ala Gln Lys Pro Ser Val Ala Pro Arg Gln Asp His
                650                  655                  660
Gln Leu Asp Lys Lys Asp Gly Ile Tyr Pro Ala Gln Leu Val Asn
                665                  670                  675
Tyr
```

(2) INFORMATION FOR SEQ ID NO:8:

(i) SEQUENCE CHARACTERISTICS:
        (A) LENGTH: 2301
        (B) TYPE: nucleic acid
        (C) STRANDEDNESS: single
        (D) TOPOLOGY: linear (ii) MOLECULE TYPE: cDNA (iii) HYPOTHETICAL: no (iv) ANTI-SENSE: no (vi) ORIGINAL SOURCE:
        (A) ORGANISM: mouse (ix) FEATURE:
        (D) OTHER INFORMATION: cDNA for Huntington-interacting
            protein - mHIP1

(xi) SEQUENCE DESCRIPTION: SEQ ID NO: 8:

```
GGCACGAGGG CTCATTCAGA TCCCCCAGCT GCCCGAGAAT CCACCCAACT           50

TCCTACGAGC CTCGGCCCTG TCAGAGCACA TCAGTCCTGT GGTGGTGATC          100

CCGGCAGAGG TGTCATCCCC AGACAGTGAG CCTGTCCTGG AGAAGGATGA          150

CCTCATGGAC ATGGACGCCT CCCAGCAGAC TTTGTTTGAC AACAAGTTTG          200

ATGACGTCTT TGGCAGCTCA TTGAGCAGCG ACCCTTTCAA TTTCAACAAT          250

CAAAATGGCG TGAACAAGGA CGAGAAGGAC CACTTGATTG AACGCCTGTA          300

CAGAGAGATC AGTGGACTGA CAGGGCAGCT GGACAACATG AAGATTGAGA          350

GCCAGCGGGC CATGCTGCAG CTGAAGGGTC GAGTGAGTGA GCTGGAGGCA          400

GAGCTAGCAG AGCAGCAGCA CTTGGGCCGG CAGGCTATGG ATGACTGCGA          450
```

```
GTTCCTGCGC ACTGAGCTGG ATGAACTGAA GAGGCAGCGA GAGGACACGG      500

AGAAGGCACA GCGCAGCCTG ACTGAGATAG AAAGAAAGGC CCAGGCTAAT      550

GAACAGAGGT ATAGCAAGTT AAAAGAGAAG TACAGTGAAC TGGTGCAGAA      600

CCATGCTGAC CTGCTGCGGA GAACGCAGA  GGTGACCAAA CAGGTGTCCG      650

TGGCCCGGCA AGCCCAGGTG GATTTGGAAA GAGAGAAAAA AGAGCTAGCA      700

GATTCCTTTG CACGTGTAAG TGACCAGGCC CAGCGGAAGA CTCAAGAGCA      750

ACAGGATGTT CTAGAGAACC TGAAGCATGA ACTGGCCACC AGCAGACAGG      800

AGCTGCAGGT CCTCCACAGC AACCTGGAAA CCTCTGCCCA GTCAGAAGCG      850

AAATGGCTGA CACAGATCGC CGAGTTGGAG AAGGAACAAG GCAGCTTGGC      900

GACTGTTGCA GCTCAGAGAG AGGAAGAGTT ATCAGCCCTC CGAGACCAGC      950

TGGAAAGCAC CCAGATCAAG CTGGCTGGGG CCCAGGAATC CATGTGCCAG     1000

CAGGTGAAGG ACCAGAGGAA AACCCTCTTG GCAGGGATCA GGAAGGCTGC     1050

GGAGCGTGAG ATACAGGAGG CGCTGAGCCA GCTTGAGGAA CCCACCCTCA     1100

TCAGCTGTGC AGGATCCACA GATCACCTTC TCTCCAAAGT CAGCTCCGTT     1150

TCCAGCTGCC TCGAGCAACT GGAAAAGAAC GGCAGCCAGT ATCTGGCCTG     1200

CCCAGAAGAT ATTAGTGAGC TTCTGCACTC GATCACCCTG CTTGCCCACT     1250

TGACCGGTGA CACTGTCATC CAGGGGAGTG CCACCAGCCT CCGGGCCCCA     1300

CCGGAGCCAG CCGACTCGTT GACGGAGGCC TGTAGGCAGT ATGGCAGAGA     1350

AACCCTGGCC TATCTGTCCT CCCTGGAGGA GAGGGAACT  GTGGAGAATG     1400

CTGACGTCAC AGCCCTTAGG AATTGCCTCA GCAGGGTCAA GACCCTTGGC     1450

GAGGAGCTGC TGCCCAGGGG CCTGGACATC AAGCAGGAAG AGCTGGGTGA     1500

CCTGGTGGAC AAGGAGATGG CAGCCACTTC AGCTGCCATT GAAGCTGCCA     1550

CCACCCGGAT AGAGGAAATT CTCAGTAAGT CCCGAGCAGG AGACACGGGA     1600

GTCAAGCTGG AGGTGAATGA GAGGATCCTG GGTTCCTGTA CCAGCCTGAT     1650

GCAGGCCATC AAGGTGCTCG TTGTGGCCTC CAAGGACCTC CAGAAGGAGA     1700

TAGTGGAGAG TGGCAGGGGT AGTGCATCCC CTAAAGAATT TTACGCCAAG     1750

AACTCTCGGT GGACGGAAGG GCTGATATCC GCCTCCAAAG CTGTTGGTTG     1800

GGGAGCTACC ATCATGGTGG ATGCTGCTGA TCTTGTGGTC CAAGGCAAAG     1850

GGAAGTTCGA GGAGCTGATG GTGTGTTCAC GCGAGATTGC TGCCAGTACT     1900

GCCCAGCTCG TGGCTGCATC CAAGGTGAAA GCGAACAAGG GCAGCCTCAA     1950

TCTGACCCAG CTGCAGCAGG CCTCTCGAGG AGTGAACCAG GCCACAGCCG     2000

CTGTGGTGGC CTCAACCATT TCTGGCAAAT CTCAGATTGA GGAAACAGAC     2050

AGTATGGACT TCTCAAGCAT GACACTGACC CAGATCAAGC GCCAGGAGAT     2100

GGATTCCCAG GTTAGGGTGC TGGAGCTGGA AAATGACCTG CAGAAGGAGC     2150

GTCAGAAACT AGGAGAGCTA CGGAAGAAAC ACTACGAGCT GGAGGGCGTG     2200

GCTGAGGGCT GGGAGGAAGG GACAGAAGCA TCACCGTCTA CTGTCCAAGA     2250

AGCAATACCG GACAAAGAGT AGAGCCAAGC CGACACCCCA CACATCAGAA     2300

A                                                         2301
```

(2) INFORMATION FOR SEQ ID NO: 9:

-continued

```
    (i) SEQUENCE CHARACTERISTICS:
        (A) LENGTH: 756
        (B) TYPE: amino acid
        (D) TOPOLOGY: linear (ii) MOLECULE TYPE: protein (iii) HYPOTHETICAL: no (vi) ORIGINAL SOURCE:
        (A) ORGANISM: mouse (ix) FEATURE:
        (D) OTHER INFORMATION: Huntington-interacting protein (xi) SEQUENCE DESCRIPTION: SEQ ID NO: 9:
```

Ala Arg Gly Leu Ile Gln Ile Pro Gln Leu Pro Glu Asn Pro Pro
                  5                  10                  15

Asn Phe Leu Arg Ala Ser Ala Leu Ser Glu His Ile Ser Pro Val
                 20                  25                  30

Val Val Ile Pro Ala Glu Val Ser Ser Pro Asp Ser Glu Pro Val
                 35                  40                  45

Leu Glu Lys Asp Asp Leu Met Asp Met Asp Ala Ser Gln Gln Thr
                 50                  55                  60

Leu Phe Asp Asn Lys Phe Asp Asp Val Phe Gly Ser Ser Leu Ser
                 65                  70                  75

Ser Asp Pro Phe Asn Phe Asn Asn Gln Asn Gly Val Asn Lys Asp
                 80                  85                  90

Glu Lys Asp His Leu Ile Glu Arg Leu Tyr Arg Glu Ile Ser Gly
                 95                 100                 105

Leu Thr Gly Gln Leu Asp Asn Met Lys Ile Glu Ser Gln Arg Ala
                110                 115                 120

Met Leu Gln Leu Lys Gly Arg Val Ser Glu Leu Glu Ala Glu Leu
                125                 130                 135

Ala Glu Gln Gln His Leu Gly Arg Gln Ala Met Asp Asp Cys Glu
                140                 145                 150

Phe Leu Arg Thr Glu Leu Asp Glu Leu Lys Arg Gln Arg Glu Asp
                155                 160                 165

Thr Glu Lys Ala Gln Arg Ser Leu Thr Glu Ile Glu Arg Lys Ala
                170                 175                 180

Gln Ala Asn Glu Gln Arg Tyr Ser Lys Leu Lys Glu Lys Tyr Ser
                185                 190                 195

Glu Leu Val Gln Asn His Ala Asp Leu Leu Arg Lys Asn Ala Glu
                200                 205                 210

Val Thr Lys Gln Val Ser Val Ala Arg Gln Ala Gln Val Asp Leu
                215                 220                 225

Glu Arg Glu Lys Lys Glu Leu Ala Asp Ser Phe Ala Arg Val Ser
                230                 235                 240

Asp Gln Ala Gln Arg Lys Thr Gln Glu Gln Gln Asp Val Leu Glu
                245                 250                 255

Asn Leu Lys His Glu Leu Ala Thr Ser Arg Gln Glu Leu Gln Val
                260                 265                 270

Leu His Ser Asn Leu Glu Thr Ser Ala Gln Ser Glu Ala Lys Trp
                275                 288                 285

Leu Thr Gln Ile Ala Glu Leu Glu Lys Glu Gln Gly Ser Leu Ala
                290                 295                 300

Thr Val Ala Ala Gln Arg Glu Glu Leu Ser Ala Leu Arg Asp
                305                 310                 315

-continued

```
Gln Leu Glu Ser Thr Gln Ile Lys Leu Ala Gly Ala Gln Glu Ser
            320                 325                 330

Met Cys Gln Gln Val Lys Asp Gln Arg Lys Thr Leu Leu Ala Gly
            335                 340                 345

Ile Arg Lys Ala Ala Glu Arg Glu Ile Gln Glu Ala Leu Ser Gln
            350                 355                 360

Leu Glu Glu Pro Thr Leu Ile Ser Cys Ala Gly Ser Thr Asp His
            365                 370                 375

Leu Leu Ser Lys Val Ser Ser Val Ser Ser Cys Leu Glu Gln Leu
            380                 385                 390

Glu Lys Asn Gly Ser Gln Tyr Leu Ala Cys Pro Glu Asp Ile Ser
            395                 400                 405

Glu Leu Leu His Ser Ile Thr Leu Leu Ala His Leu Thr Gly Asp
            410                 415                 420

Thr Val Ile Gln Gly Ser Ala Thr Ser Leu Arg Ala Pro Pro Glu
            425                 430                 435

Pro Ala Asp Ser Leu Thr Glu Ala Cys Arg Gln Tyr Gly Arg Glu
            440                 445                 450

Thr Leu Ala Tyr Leu Ser Ser Leu Glu Glu Gly Thr Val Glu
            455                 460                 465

Asn Ala Asp Val Thr Ala Leu Arg Asn Cys Leu Ser Arg Val Lys
            470                 475                 480

Thr Leu Gly Glu Glu Leu Leu Pro Arg Gly Leu Asp Ile Lys Gln
            485                 490                 495

Glu Glu Leu Gly Asp Leu Val Asp Lys Glu Met Ala Ala Thr Ser
            500                 505                 510

Ala Ala Ile Glu Ala Ala Thr Thr Arg Ile Glu Glu Ile Leu Ser
            515                 520                 525

Lys Ser Arg Ala Gly Asp Thr Gly Val Lys Leu Glu Val Asn Glu
            530                 535                 540

Arg Ile Leu Gly Ser Cys Thr Ser Leu Met Gln Ala Ile Lys Val
            545                 550                 555

Leu Val Val Ala Ser Lys Asp Leu Gln Lys Glu Ile Val Glu Ser
            560                 565                 570

Gly Arg Gly Ser Ala Ser Pro Lys Glu Phe Tyr Ala Lys Asn Ser
            575                 588                 585

Arg Trp Thr Glu Gly Leu Ile Ser Ala Ser Lys Ala Val Gly Trp
            590                 595                 600

Gly Ala Thr Ile Met Val Asp Ala Ala Asp Leu Val Val Gln Gly
            605                 610                 615

Lys Gly Lys Phe Glu Glu Leu Met Val Cys Ser Arg Glu Ile Ala
            620                 625                 630

Ala Ser Thr Ala Gln Leu Val Ala Ala Ser Lys Val Lys Ala Asn
            635                 640                 645

Lys Gly Ser Leu Asn Leu Thr Gln Leu Gln Gln Ala Ser Arg Gly
            650                 655                 660

Val Asn Gln Ala Thr Ala Ala Val Val Ala Ser Thr Ile Ser Gly
            665                 670                 675

Lys Ser Gln Ile Glu Glu Thr Asp Ser Met Asp Phe Ser Ser Met
            680                 685                 690

Thr Leu Thr Gln Ile Lys Arg Gln Glu Met Asp Ser Gln Val Arg
            695                 700                 705
```

-continued

```
Val Leu Glu Leu Glu Asn Asp Leu Gln Lys Glu Arg Gln Lys Leu
            710                 715                 720

Gly Glu Leu Arg Lys Lys His Tyr Glu Leu Glu Gly Val Ala Glu
            725                 730                 735

Gly Trp Glu Glu Gly Thr Glu Ala Ser Pro Ser Thr Val Gln Glu
            740                 745                 750

Ala Ile Pro Asp Lys Glu
            755
```

(2) INFORMATION FOR SEQ ID NO:10:

(i) SEQUENCE CHARACTERISTICS:
        (A) LENGTH: 3979
        (B) TYPE: nucleic acid
        (C) STRANDEDNESS: single
        (D) TOPOLOGY: linear (ii) MOLECULE TYPE: cDNA (iii) HYPOTHETICAL: no (iv) ANTI-SENSE: no (vi) ORIGINAL SOURCE:
        (A) ORGANISM: mouse (ix) FEATURE:
        (D) OTHER INFORMATION: cDNA for Huntington-interacting
            protein - mHIP1a (xi) SEQUENCE DESCRIPTION: SEQ ID NO: 10:

```
GGCACGAGGC GGCGCGCGGC CTCCGTGTGC CTAGGCTTGA GGCGGGCGGT              50

GACGCCTCAT TCGCGCGGAG CCGGGCCGGG ACACGGTCGG CGGCAGCATG             100

AACAGCATCA AGAATGTGCC GGCGCGGGTG CTGAGCCGCA GGCCGGGCCA             150

CAGCCTAGAG GCCGAGCGCG AGCAGTTCGA CAAGACGCAG GCCATCAGTA             200

TCAGCAAAGC CATCAACAGC CAGGAGGCCC CAGTGAAGGA GAAGCATGCC             250

CGGCGTATCA TCCTGGGCAC GCATCATGAG AAGGGAGCCT TCACCTTCTG             300

GTCCTATGCC ATCGGCCTGC CGCTGTCCAG CAGCTCCATC CTCAGCTGGA             350

AGTTCTGTCA CGTCCTTCAC AAGGTCCTCC GGGACGGACA CCCCAACGTC             400

CTGCATGACT ATCAGCGGTA CCGGAGCAAC ATACGTGAGA TCGGTGACTT             450

GTGGGGCCAC CTTCGTGACC AGTATGGACA CCTGGTGAAT ATCTATACCA             500

AACTGTTGCT GACTAAGATC TCCTTCCACC TTAAGCACCC CCAGTTTCCT             550

GCAGGCCTGG AGGTAACAGA TGAGGTGTTG GAGAAGGCGG CGGGAACTGA             600

TGTCAACAAC ATTTTTCAGC TTACCGTGGA GATGTTTGAC TACATGGACT             650

GTGAACTGAA GCTTTCTGAG TCAGTTTTCC GGCAGCTCAA CACGGCCATC             700

GCAGTGTCCC AGATGTCTTC TGGCCAGTGT CGCCTAGCGC CGCTCATCCA             750

GGTCATTCAG GACTGCAGCC ACCTGTACCA CTACACAGTG AAGCTCATGT             800

TTAAGCTGCA CTCCTGTCTC CCGGCAGACA CCCTGCAAGG CCACAGGGAT             850

CGGTTCCACG AGCAGTTCCA CAGCCTCAAA AACTTCTTCC GCCGGGCTTC             900

AGACATGCTG TACTTCAAGA GGCTCATCCA GATCCCGCGG CTGCCTGAGG             950

GACCCCCCAA TTTCCTGCGG GCTTCAGCCC TGGCTGAGCA CATCAAGCCG            1000

GTGGTGGTGA TTCCCGAGGA GGCCCCAGAG GAAGAGGAGC CTGAGAACCT            1050

AATTGAAATC AGCAGTGCGC CCCCTGCTGG GGAGCCAGTG GTGGTGGCTG            1100
```

-continued

| | | |
|---|---|---|
| ACCTCTTTGA TCAGACCTTT GGACCCCCCA ATGGCTCCAT GAAGGATGAC | | 1150 |
| AGGGACCTCC AAATCGAGAA CTTGAAGAGA GAGGTGGAGA CCCTCCGTGC | | 1200 |
| TGAGCTGGAG AAGATTAAGA TGGAGGCACA GCGGTACATC TCCCAGCTGA | | 1250 |
| AGGGCCAGGT GAATGGCCTG GAGGCAGAGC TGGAGGAGCA GCGCAAGCAG | | 1300 |
| AAGCAGAAGG CCCTGGTGGA CAACGAGCAG CTGCGCCACG AGCTGGCCCA | | 1350 |
| GCTCAAGGCC CTGCAGCTGG AGGGCGCCCG CAACCAGGGC CTTCGAGAGG | | 1400 |
| AAGCAGAGAG GAAGGCCAGT GCCACGGAGG CACGCTACAG CAAGCTGAAG | | 1450 |
| GAGAAACACA GCGAACTCAT TAACACGCAC GCCGAGCTGC TCAGGAAGAA | | 1500 |
| CGCAGACACG GCCAAGCAGC TGACAGTGAC ACAGCAGAGC CAGGAGGAGG | | 1550 |
| TGGCACGGGT AAAGGAACAG CTGGCCTTCC AGATGGAGCA AGCGAAGCGT | | 1600 |
| GAGTCTGAGA TGAAGATGGA AGAGCAGAGC GACCAGTTGG AGAAGCTCAA | | 1650 |
| GAGGGAGCTG GCGGCCAGGG CAGGAGAGCT GGCCCGTGCG CAGGAGGCCC | | 1700 |
| TGAGCCGCAC AGAACAGAGT GGGTCAGAGC TGAGCTCACG GCTGGACACA | | 1750 |
| CTGAACGCGG AGAAGGAAGC CCTGAGTGGA GTCGTTCGGC AGCGTGAGGC | | 1800 |
| AGAGCTGCTG GCCGCTCAGA GCCTGGTGCG GGAGAAGGAG GAGGCGCTTA | | 1850 |
| GCCAAGAGCA GCAGCGGAGC TCCCAGGAGA AGGGCGAGCT ACGGGGGCAG | | 1900 |
| CTGGCAGAAA AGGAGTCTCA GGAGCAGGGG CTTCGGCAGA AGCTGCTGGA | | 1950 |
| TGAGCAGTTG GCGGTGTTGC GAAGTGCAGC CGCCGAGGCA GAGGCCATCC | | 2000 |
| TACAGGATGC AGTGAGCAAG CTGGACGACC CCCTGCACCT CCGCTGCACC | | 2050 |
| AGCTCCCCAG ACTACTTGGT GAGCCGGGCT CAGGCAGCCC TGGACAGCGT | | 2100 |
| GAGCGGCCTG GAGCAGGGCC ACACCCAGTA CCTGGCTTCC TCCGAAGATG | | 2150 |
| CTTCTGCCCT GGTGGCAGCG CTGACCCGCT TCTCCCATTT GGCTGCGGAC | | 2200 |
| ACCATTGTCA ATGGTGCCGC CACCTCCCAC CTGGCCCCCA CCGACCCCGC | | 2250 |
| CGACCGCCTG ATGGACACAT GCAGGGAGTG TGGAGCCCGG GCTCTGGAGC | | 2300 |
| TGGTGGGACA GCTGCAAGAC CAGACAGTGC TACGGAGGGC TCAGCCCAGC | | 2350 |
| CTGATGCGGG CCCCCCTGCA GGGCATTCTG CAGTTGGGCC AGGACTTGAA | | 2400 |
| GCCTAAGAGC CTGGATGTAC GGCAAGAGGA GCTAGGGGCC ATGGTGGACA | | 2450 |
| AGGAGATGGC GGCCACCTCG GCAGCCATTG AGGACGCTGT GCGGAGGATC | | 2500 |
| GAGGACATGA TGAGCCAGGC CCGCCACGAG AGCTCAGGCG TGAAACTGGA | | 2550 |
| GGTGAATGAG AGGATCCTCA ACTCCTGCAC AGACCTGATG AAGGCTATCC | | 2600 |
| GGCTCCTGGT GATGACCTCC ACCAGCCTGC AGAAGGAAAT TGTGGAGAGC | | 2650 |
| GGCAGGGGGG CAGCAACGCA GCAGGAATTT TATGCCAAGA ATTCACGGTG | | 2700 |
| GACTGAAGGC CTCATCTCAG CCTCTAAGGC AGTGGGCTGG GGAGCCACAC | | 2750 |
| AGCTGGTGGA GTCAGCTGAC AAGGTTGTGC TTCACATGGG CAAATACGAG | | 2800 |
| GAACTCATCG TCTGCTCCCA TGAGATTGCG GCCAGCACGG CCCAGCTGGT | | 2850 |
| GGCAGCCTCG AAGGTGAAAG CCAACAAGAA CAGTCCCCAC TTGAGCCGCC | | 2900 |
| TGCAGGAATG TTCCCGCACT GTCAACGAGA GGGCTGCCAA CGTCGTGGCC | | 2950 |
| TCCACCAAAT CTGGCCAGGA GCAGATTGAG ACAGAGACA CCATGGATTT | | 3000 |
| CTCTGGCCTG TCCCTCATCA AGTTGAAGAA GCAGGAGATG GAGACACAGG | | 3050 |

-continued

```
TGCGAGTCTT GGAGCTGGAG AAGACACTAG AGGCAGAGCG TGTCCGGCTC       3100

GGGGAGCTTC GGAAACAGCA CTATGTACTG GCTGGGGGGA TGGGAACACC       3150

TAGCGAAGAA GAACCCAGCA GACCCAGCCC AGCTCCCCGA AGTGGGGCCA       3200

CTAAGAAGCC ACCGCTGGCC CAGAAACCCA GCATAGCCCC CAGGACAGAC       3250

AACCAGCTCG ACAAAAAGGA TGGTGTCTAC CCAGCTCAAC TTGTGAACTA       3300

CTAGGCCCCT AAGGTGTTCA GCAGGATGGC TGGTGGTTGT GCCTGGGCTT       3350

CATGTGGCTG TCTGGCAGTG GTCAAGGGGC CTCTGAGAAG CCTCCAACTC       3400

CTGCCCAAGG GGCCTAGTCT GTGGGACAGT TCATCTGGAT GTGAATCTAT       3450

TTATCTTAAG TAGGAACTGC CTCGAGCAGC TGGGACCCAG CAGGCCTGAG       3500

CCACAAATCT GCAGCGGACA TCAGAGATAG TCTGAATGCT GCGAGGTATT       3550

TCTTTCTTCG TAAGTTTAGT CAGCACACTG GGAAAAGGTC ACATAAGCCA       3600

GGAGCCTCCT TGTCTCTGGA CTCAAAAGTC TGAGGCCTTA AGTGAACAAC       3650

AGAAAGAGGG TCCCTGCTGG CTACCAGGGA TAAGGGGATG ACCTGTGACC       3700

CTTGAGCCAG GGAGAGCAGG TAAGCTGGGT GGTGTCATCA CCTGGGGGCC       3750

TGGTGCTAGG GCATCCATGC TGGGAGCCCC AGGAGACCAG GCTTTGTGTG       3800

GGAGCCTGGC ATCATCGTGG CTGGGGCAGC CCCTGCTCAG GTGCTGTCTC       3850

TGCCCGTGAC CTTGAAGCCA CCCTCCCCCC GTACAGTTTT CCATTCTCCT       3900

GGCTACTAGT GTGGCTGTTC ATTGCCTACC TTGATGAGTA GATTTCAGCC       3950

CTCCTAAAGC TGGGGCCTTT CCTCGTGCC                              3979
```

(2) INFORMATION FOR SEQ ID NO: 11:

(i) SEQUENCE CHARACTERISTICS:
        (A) LENGTH: 1068
        (B) TYPE: amino acid
        (D) TOPOLOGY: linear (ii) MOLECULE TYPE: protein (iii) HYPOTHETICAL: no (vi) ORIGINAL SOURCE:
        (A) ORGANISM: mouse (ix) FEATURE:
        (D) OTHER INFORMATION: Huntington-interacting protein -mHIP1a (xi) SEQUENCE DESCRIPTION: SEQ ID NO:11:

```
Met Asn Ser Ile Lys Asn Val Pro Ala Arg Val Leu Ser Arg Arg
              5                  10                  15

Pro Gly His Ser Leu Glu Ala Glu Arg Glu Gln Phe Asp Lys Thr
             20                  25                  30

Gln Ala Ile Ser Ile Ser Lys Ala Ile Asn Ser Gln Glu Ala Pro
             35                  40                  45

Val Lys Glu Lys His Ala Arg Arg Ile Ile Leu Gly Thr His His
             50                  55                  60

Glu Lys Gly Ala Phe Thr Phe Trp Ser Tyr Ala Ile Gly Leu Pro
             65                  70                  75

Leu Ser Ser Ser Ile Leu Ser Trp Lys Phe Cys His Val Leu
             80                  85                  90

His Lys Val Leu Arg Asp Gly His Pro Asn Val Leu His Asp Tyr
             95                 100                 105
```

```
Gln Arg Tyr Arg Ser Asn Ile Arg Glu Ile Gly Asp Leu Trp Gly
            110                 115                 120

His Leu Arg Asp Gln Tyr Gly His Leu Val Asn Ile Tyr Thr Lys
            125                 130                 135

Leu Leu Leu Thr Lys Ile Ser Phe His Leu Lys His Pro Gln Phe
            140                 145                 150

Pro Ala Gly Leu Glu Val Thr Asp Glu Val Leu Glu Lys Ala Ala
            155                 160                 165

Gly Thr Asp Val Asn Asn Ile Phe Gln Leu Thr Val Glu Met Phe
            170                 175                 180

Asp Tyr Met Asp Cys Glu Leu Lys Leu Ser Glu Ser Val Phe Arg
            185                 190                 195

Gln Leu Asn Thr Ala Ile Ala Val Ser Gln Met Ser Ser Gly Gln
            200                 205                 210

Cys Arg Leu Ala Pro Leu Ile Gln Val Ile Gln Asp Cys Ser His
            215                 220                 225

Leu Tyr His Tyr Thr Val Lys Leu Met Phe Lys Leu His Ser Cys
            230                 235                 240

Leu Pro Ala Asp Thr Leu Gln Gly His Arg Asp Arg Phe His Glu
            245                 250                 255

Gln Phe His Ser Leu Lys Asn Phe Phe Arg Arg Ala Ser Asp Met
            260                 265                 270

Leu Tyr Phe Lys Arg Leu Ile Gln Ile Pro Arg Leu Pro Glu Gly
            275                 280                 285

Pro Pro Asn Phe Leu Arg Ala Ser Ala Leu Ala Glu His Ile Lys
            290                 295                 300

Pro Val Val Val Ile Pro Glu Glu Ala Pro Glu Glu Glu Glu Pro
            305                 310                 315

Glu Asn Leu Ile Glu Ile Ser Ser Ala Pro Pro Ala Gly Glu Pro
            320                 325                 330

Val Val Val Ala Asp Leu Phe Asp Gln Thr Phe Gly Pro Pro Asn
            335                 340                 345

Gly Ser Met Lys Asp Asp Arg Asp Leu Gln Ile Glu Asn Leu Lys
            350                 355                 360

Arg Glu Val Glu Thr Leu Arg Ala Glu Leu Glu Lys Ile Lys Met
            365                 370                 375

Glu Ala Gln Arg Tyr Ile Ser Gln Leu Lys Gly Gln Val Asn Gly
            380                 385                 390

Leu Glu Ala Glu Leu Glu Gln Arg Lys Gln Lys Gln Lys Ala
            395                 400                 405

Leu Val Asp Asn Glu Gln Leu Arg His Glu Leu Ala Gln Leu Lys
            410                 415                 420

Ala Leu Gln Leu Glu Gly Ala Arg Asn Gln Gly Leu Arg Glu Glu
            425                 430                 435

Ala Glu Arg Lys Ala Ser Ala Thr Glu Ala Arg Tyr Ser Lys Leu
            440                 445                 450

Lys Glu Lys His Ser Glu Leu Ile Asn Thr His Ala Glu Leu Leu
            455                 460                 465

Arg Lys Asn Ala Asp Thr Ala Lys Gln Leu Thr Val Thr Gln Gln
            470                 475                 480

Ser Gln Glu Glu Val Ala Arg Val Lys Glu Gln Leu Ala Phe Gln
            485                 490                 495

Met Glu Gln Ala Lys Arg Glu Ser Glu Met Lys Met Glu Glu Gln
```

```
                500                 505                 510
Ser Asp Gln Leu Glu Lys Leu Lys Arg Glu Leu Ala Ala Arg Ala
                515                 520                 525
Gly Glu Leu Ala Arg Ala Gln Glu Ala Leu Ser Arg Thr Glu Gln
                530                 535                 540
Ser Gly Ser Glu Leu Ser Ser Arg Leu Asp Thr Leu Asn Ala Glu
                545                 550                 555
Lys Glu Ala Leu Ser Gly Val Val Arg Gln Arg Glu Ala Glu Leu
                560                 565                 570
Leu Ala Ala Gln Ser Leu Val Arg Glu Lys Glu Glu Ala Leu Ser
                575                 580                 585
Gln Glu Gln Gln Arg Ser Ser Gln Glu Lys Gly Glu Leu Arg Gly
                590                 595                 600
Gln Leu Ala Glu Lys Glu Ser Gln Glu Gln Gly Leu Arg Gln Lys
                605                 610                 615
Leu Leu Asp Glu Gln Leu Ala Val Leu Arg Ser Ala Ala Ala Glu
                620                 625                 630
Ala Glu Ala Ile Leu Gln Asp Ala Val Ser Lys Leu Asp Asp Pro
                635                 640                 645
Leu His Leu Arg Cys Thr Ser Ser Pro Asp Tyr Leu Val Ser Arg
                650                 655                 660
Ala Gln Ala Ala Leu Asp Ser Val Ser Gly Leu Glu Gln Gly His
                665                 670                 675
Thr Gln Tyr Leu Ala Ser Ser Glu Asp Ala Ser Ala Leu Val Ala
                680                 685                 690
Ala Leu Thr Arg Phe Ser His Leu Ala Ala Asp Thr Ile Val Asn
                695                 700                 705
Gly Ala Ala Thr Ser His Leu Ala Pro Thr Asp Pro Ala Asp Arg
                710                 715                 720
Leu Met Asp Thr Cys Arg Glu Cys Gly Ala Arg Ala Leu Glu Leu
                725                 730                 735
Val Gly Gln Leu Gln Asp Gln Thr Val Leu Arg Arg Ala Gln Pro
                740                 745                 750
Ser Leu Met Arg Ala Pro Leu Gln Gly Ile Leu Gln Leu Gly Gln
                755                 760                 765
Asp Leu Lys Pro Lys Ser Leu Asp Val Arg Gln Glu Glu Leu Gly
                770                 775                 780
Ala Met Val Asp Lys Glu Met Ala Ala Thr Ser Ala Ala Ile Glu
                785                 790                 795
Asp Ala Val Arg Arg Ile Glu Asp Met Met Ser Gln Ala Arg His
                800                 805                 810
Glu Ser Ser Gly Val Lys Leu Glu Val Asn Glu Arg Ile Leu Asn
                815                 820                 825
Ser Cys Thr Asp Leu Met Lys Ala Ile Arg Leu Leu Val Met Thr
                830                 835                 840
Ser Thr Ser Leu Gln Lys Glu Ile Val Glu Ser Gly Arg Gly Ala
                845                 850                 855
Ala Thr Gln Gln Glu Phe Tyr Ala Lys Asn Ser Arg Trp Thr Glu
                860                 865                 870
Gly Leu Ile Ser Ala Ser Lys Ala Val Gly Trp Gly Ala Thr Gln
                875                 880                 885
Leu Val Glu Ser Ala Asp Lys Val Val Leu His Met Gly Lys Tyr
                890                 895                 900
```

```
Glu Glu Leu Ile Val Cys Ser His Glu Ile Ala Ala Ser Thr Ala
            905                 910                 915

Gln Leu Val Ala Ala Ser Lys Val Lys Ala Asn Lys Asn Ser Pro
            920                 925                 930

His Leu Ser Arg Leu Gln Glu Cys Ser Arg Thr Val Asn Glu Arg
            935                 940                 945

Ala Ala Asn Val Val Ala Ser Thr Lys Ser Gly Gln Glu Gln Ile
            950                 955                 960

Glu Asp Arg Asp Thr Met Asp Phe Ser Gly Leu Ser Leu Ile Lys
            965                 970                 975

Leu Lys Lys Gln Glu Met Glu Thr Gln Val Arg Val Leu Glu Leu
            980                 985                 990

Glu Lys Thr Leu Glu Ala Glu Arg Val Arg Leu Gly Glu Leu Arg
            995                 1000                1005

Lys Gln His Tyr Val Leu Ala Gly Gly Met Gly Thr Pro Ser Glu
            1010                1015                1020

Glu Glu Pro Ser Arg Pro Ser Pro Ala Pro Arg Ser Gly Ala Thr
            1025                1030                1035

Lys Lys Pro Pro Leu Ala Gln Lys Pro Ser Ile Ala Pro Arg Thr
            1040                1045                1050

Asp Asn Gln Leu Asp Lys Lys Asp Gly Val Tyr Pro Ala Gln Leu
            1055                1060                1065

Val Asn Tyr
```

(2) INFORMATION FOR SEQ ID NO:12:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: other DNA (iii) HYPOTHETICAL: no (iv) ANTI-SENSE: no (vi) ORIGINAL SOURCE:
        (A) ORGANISM: human (xi) SEQUENCE DESCRIPTION: SEQ ID NO: 12:

GAAGATACCC CACCAAAC                            18

(2) INFORMATION FOR SEQ ID NO:13:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: other DNA (iii) HYPOTHETICAL: no (iv) ANTI-SENSE: no (vi) ORIGINAL SOURCE:
        (A) ORGANISM: human (xi) SEQUENCE DESCRIPTION: SEQ ID NO: 13:

GCTTGACAGT GTAGTCATAA AGGTGGCTGC AGTCC            35

(2) INFORMATION FOR SEQ ID NO:14:

(i) SEQUENCE CHARACTERISTICS:
       (A) LENGTH: 24
       (B) TYPE: nucleic acid
       (C) STRANDEDNESS: single
       (D) TOPOLOGY: linear (ii) MOLECULE TYPE: other DNA (iii) HYPOTHETICAL: no (iv) ANTI-SENSE: no (vi) ORIGINAL SOURCE:
       (A) ORGANISM: human (xi) SEQUENCE DESCRIPTION: SEQ ID NO: 14:

GGACATGTCC AGGGAGTTGA ATAC                                              24

(2) INFORMATION FOR SEQ ID NO:15:

(i) SEQUENCE CHARACTERISTICS:
       (A) LENGTH: 51
       (B) TYPE: nucleic acid
       (C) STRANDEDNESS: single
       (D) TOPOLOGY: linear (ii) MOLECULE TYPE: other nucleic acid (iii) HYPOTHETICAL: no (iv) ANTI-SENSE: yes (vi) ORIGINAL SOURCE:
       (A) ORGANISM: human (ix) FEATURE:
       (D) OTHER INFORMATION: N at 39, 40, 44, 45, 49, and 50
           is Inosine (xi) SEQUENCE DESCRIPTION: SEQ ID NO: 15:

CUACUACUAC UACUAGGCCA CGCGTCGACT AGTACGGGNN GGGNNGGGNN G                 51

(2) INFORMATION FOR SEQ ID NO:16:

(i) SEQUENCE CHARACTERISTICS:
       (A) LENGTH: 516
       (B) TYPE: nucleic acid
       (C) STRANDEDNESS: double
       (D) TOPOLOGY: linear (ii) MOLECULE TYPE: genomic DNA (iii) HYPOTHETICAL: no (iv) ANTI-SENSE: no (vi) ORIGINAL SOURCE:
       (A) ORGANISM: human (x) FEATURE:
       (D) OTHER INFORMATION: exon 1 of HIP1

(xi) SEQUENCE DESCRIPTION: SEQ ID NO: 16:

TCTGTGGAAG GTTTGGAGGG GAGAGAGGGG CAGCTGGATG CTCTTGGGCC ACGGTCGCCC        60

CTGATCTCTG CGCCTCTTCC TCCTGCTCCG GGAGAAATAA TGTTTCCCTG GGGGATGAAA       120

GCATCTCTTT GTGCGGGCTT TAATTGCCAT GTTGTTGTGC CAAGGGAGTG AGTGGCGGCG       180

GGACCAGCAG CTGGGCACAG CCAATGCCAG GCAGTGGTGC CCACTCCCTC AGGACGCCCA       240

```
GCCAGCTGGC TCCTGGGAGC GCTGCCCACC TCTGCCCCCA GCTGGGCGCC TGCAAGGAAC        300

CGACCACCCG TGGGGCTGGG GGAGGTTGGC TGGAGGAGGA GAAAGGGGCG GGCTCTGGGA        360

GGGTCTCAGC CACTCTCAGA GGCTTATTCA TCTCATCCTC CTTTCCCTCC CCCTTCTTGT        420

TTTTCAGACT GTCAGCATCA ATAAGGCCAT TAATACGCAG GAAGTGGCTG TAAAGGAAAA        480

ACACGCCAGA AATATCCTTT GGATGTTGCT TGGAAG                                 516
```

(2) INFORMATION FOR SEQ ID NO:17:

(i) SEQUENCE CHARACTERISTICS:
        (A) LENGTH: 193
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 2 of HIP1

(xi) SEQUENCE DESCRIPTION: SEQ ID NO: 17:

```
TGTTTTCCAT AACCCCCCCT CACCGTGCAT ACTGGGCACC CACCATGAGA AAGGGGCACA         60

GACCTTCTGG TCTGTTGTCA ACCGCCTGCC TCTGTCTAGC AACCCAGTGC TCTGCTGGAA        120

GTTCTGCCAT GTGTTCCACA AACTCCTCCG AGATGGACAC CCGAACGTGA GTTCCTGGGG        180

CTATGGGGTG GCA                                                          193
```

(2) INFORMATION FOR SEQ ID NO:18:

(i) SEQUENCE CHARACTERISTICS:
        (A) LENGTH: 104
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 3 of HIP1

(xi) SEQUENCE DESCRIPTION: SEQ ID NO: 18:

```
GTGTTCTTTT GCCCCTGCAG GTCCTGAAGG ACTCTCTGAG ATACAGAAAT GAATTGAGTG         60

ACATGAGCAG GATGTGGGTG AGTTTGGAGA TGTACTCAGG AGCC                        104
```

(2) INFORMATION FOR SEQ ID NO: 19:

(i) SEQUENCE CHARACTERISTICS:

(xi) SEQUENCE DESCRIPTION: SEQ ID NO: 19:

This sequence is intentionally skipped.

(2) INFORMATION FOR SEQ ID NO:20:

(i) SEQUENCE CHARACTERISTICS:
        (A) LENGTH: 327
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 4 of HIP1

(xi) SEQUENCE DESCRIPTION: SEQ ID NO: 20:

```
AATTCCTGGC TGCAGATCTC TTGACTGTTA TGTTCTTGTT GTTGACTCTG TTTCCCCTCC      60

TCTTCCTAAA AGGGCCACCT GAGCGAGGGG TATGGCCAGC TGTGCAGCAT CTACCTGAAA     120

CTGCTAAGAA CCAAGATGGA GTACCACACC AAAGTGAGTC TCTGCGGACA GTTCTGCCGC     180

CACCGCCGCC TCCCCTGCTC CATCCCTTCA GCCCCTCCCT GGGCTCATTT GTCAGCTCTT     240

TCAGGTAATA GACAGCCCAG GCTTCTGAGG AAGTGTGCAC ATCATGTACC CAAGCTGTGA     300

GAGAGGAAAG CCACCGCCAG GCCCACG                                         327
```

(2) INFORMATION FOR SEQ ID NO:21:

(i) SEQUENCE CHARACTERISTICS:
        (A) LENGTH: 331
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 5 of HIP1

(xi) SEQUENCE DESCRIPTION: SEQ ID NO: 21:

```
GGGCTCAAGC AATCCTCCCA CCTCGGCCTC CCAAGTAGCT GGGACCACAG GCGTGTGCCA      60

CCACGCCCGG CTGAGAGAGG GCTCTTCATG TCTTCTGCCC TGACTCCCTT CCTCTGCCTC     120

CCTTCCAGAA TCCCAGGTTC CCAGGCAACC TGCAGATGAG TGACCGCCAG CTGGACGAGG     180

CTGGAGAAAG TGACGTGAAC AACTTGTAAG TGGCTCCTGC CCTGAGCCCA GGGAGGGAGA     240

AAGCTTTTGT GAATGCTGAC ACTTCTCATA AGGGTCATGG AGGGCCTGAT GGGGGGAGGC     300

CGTGGCTGGG ATGGGGACCA AAGCCCCTGG G                                    331
```

(2) INFORMATION FOR SEQ ID NO:22:

(i) SEQUENCE CHARACTERISTICS:
        (A) LENGTH: 470
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
    (A) ORGANISM: human (x) FEATURE:
    (D) OTHER INFORMATION: exon 6 of HIP1

(xi) SEQUENCE DESCRIPTION: SEQ ID NO: 22:

```
ACTGTCGCTG TCACTGTTGA CTTCACCAGG CTGCATGGCC ATAATACCCA CAAGGCTAAG      60

ACTTGGAGCT GGAGTTGTGT GTGTGTTTGC GCATGCACAT GAGCATTGGA GACTGGAGTA     120

GCGTAGAGCG TGGGGAGGG  GACAGGTAAC AGACCGGCCT CAGGCTGTGG AGTGTAAGCT     180

CTCTTTCCTC TTGGGTCCAG TTTCCAGTTA ACAGTGGAGA TGTTTGACTA CCTGGAGTGT     240

GAACTCAACC TCTTCCAAAC AGGTGAGTCT CTTCCCTCCC GTCTAACCCA GGCTCTCATG     300

GGAACTACCT AATTCCTAGT CCTCCTCTCC CTGCAAAGTG TGCAGCACAA GGGGTAGGAA     360

AATGGAGACA TTCACACCCC ATCTCTGGTC TCTCCAACCC TCGTGCAGGG AGGGACTGAA     420

CCTCTTCAGT ATTTTTCTTT TTAAGAGACA AGGTCTCGGC CGGGTGCAGT                470
```

(2) INFORMATION FOR SEQ ID NO:23:

(i) SEQUENCE CHARACTERISTICS:
    (A) LENGTH: 565
    (B) TYPE: nucleic acid
    (C) STRANDEDNESS: double
    (D) TOPOLOGY: linear (ii) MOLECULE TYPE: genomic DNA (iii) HYPOTHETICAL: no (iv) ANTI-SENSE: no (vi) ORIGINAL SOURCE:
    (A) ORGANISM: human (x) FEATURE:
    (D) OTHER INFORMATION: exon 7 of HIP1

(xi) SEQUENCE DESCRIPTION: SEQ ID NO: 23:

```
TCTTCACCTG TTTAATGGGG ATACGTTTAC CTATCTCATG GGAGTGTTGT GAAGGTTAAA      60

TGAATTAGAT GAGGTAAAGC ACGCACAGAA TCGGTCCTTG GTGTATGTTG ACCCCTGCC     120

TCTGCCCCTC TGAAGAGGCT GCCTGTAATC CCCTGGCTCT ACCACCTTTC TCCCTCACTT     180

TTATTTCCTA GTATTCAACT CCCTGGACAT GTCCCGCTCT GTGTCCGTGA CGGCAGCAGG     240

GCAGTGCCGC CTCGCCCCGC TGATCCAGGT CATCTTGGAC TGCAGCCACC TTTATGACTA     300

CACTGTCAAG CTTCTCTTCA AACTCCACTC CTGTGAGTAC CGCGGGCCAG ATCTTCTTAC     360

ATGAGATTCA GGCCAGAGGG AGGATCCCAG CCTGAGGATG TCCCCAGAGA AACGCAGTCC     420

TTCTCAGTGC CTTTGGCTGT CTGCTTCTGT TCCAAAAGGC CCCGGAGCTT CTGACCATTG     480

TGAGGATAAA AGAGCAGGGC CCAGGCTTTG GTGACCCCAG TAAAGCCCCT GGCTTGCCAC     540

TCTTGCGTCC AGTGTTACAG GATCT                                           565
```

(2) INFORMATION FOR SEQ ID NO:24:

(i) SEQUENCE CHARACTERISTICS:
    (A) LENGTH: 233
    (B) TYPE: nucleic acid
    (C) STRANDEDNESS: double (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 8 of HIP1

(xi) SEQUENCE DESCRIPTION: SEQ ID NO: 24:

```
GGGACAGCTC TAGGCCAGTC GTGGCCCCTG GCAGTGCTGG CCACATGCCC CAGGGTAGCT      60

GGGCCCCTCC CCCTCGAGAG CCCCGCTGTG GCTTCCCTGC CCTCTGGTCC CCCTCCCCTC     120

TCACACTCTT TCCAATTTCT TCCAGGCCTC CCAGCTGACA CCCTGCAAGG CCACCGGGAC     180

CGCTTCATGG AGCAGTTTAC AAAGTAAGTG GTTCAAGTAA CAGGAATGGA GGT            233
```

(2) INFORMATION FOR SEQ ID NO:25:

(i) SEQUENCE CHARACTERISTICS:
        (A) LENGTH: 578
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exons 9 and 10 of HIP1

(xi) SEQUENCE DESCRIPTION: SEQ ID NO: 25:

```
TGAATCCCAG CACCATGGAG TTTATCTCCT TGACAGCCTG TGCCTTTGGG CTGGGGAGGG      60

GGCAGGAAAG CCAGGTGGCT GCTCTGTCCC CTACATGGGG CTGATGAAGA CACCCAGCAC     120

CCCTCAGGTC CTTCTCCACC CCTAGGTTGA AAGATCTGTT CTACCGCTCC AGCAACCTGC     180

AGTACTTCAA GCGGCTCATT CAGATCCCCC AGCTGCCTGA GGTAAGCATG CCCAACCACA     240

CACCCTCGGC ACTGCAGAGG CCCCAGGTAC TCTCTTAAGG GCCGGCGGGG CCTGGCAAGC     300

AAGCACTATT TGAGGATGTG TCTCCGTCTT CAGAACCCAC CCAACTTCCT GCGAGCCTCA     360

GCCCTGTCAG AACATATCAG CCCTGTGGTG GTGATCCCTG CAGAGGCCTC ATCCCCCGAC     420

AGCGAGCCAG TCCTAGAGAA GGATGACCTC ATGGACATGG ATGCCTCTCA GCAGGTGAGG     480

ACCACTTGGG AGAGAAACTT GGCCTTTCCT CTCACCTGCA AGTACAGGGG AGAGGCTGGG     540

GGAGACCCTG GCCAAAGCCC ATTGACTCTA ACCAGGTT                            578
```

(2) INFORMATION FOR SEQ ID NO:26:

(i) SEQUENCE CHARACTERISTICS:
        (A) LENGTH: 390
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
                  (A) ORGANISM: human (x) FEATURE:
                  (D) OTHER INFORMATION: exon 11 of HIP1

(xi) SEQUENCE DESCRIPTION: SEQ ID NO: 26:

```
AAAAAAATTT AAAAAATTAA ACAGGTCTGA ACCGTTTAAT TCGAGAAAGG GGGCATTCTC      60

CCATATCACT CAACTGACCC ACACACAGAA TTCTCTGGCT CTCTGACTTA TTCTCACTCC     120

TTTTTGGTCA ACCACAGAAT TTATTTGACA ACAAGTTTGA TGACATCTTT GGCAGTTCAT     180

TCAGCAGTGA TCCCTTCAAT TTCAACAGTC AAAATGGTGT GAACAAGGAT GAGAAGTGAG     240

TCCAAGCTGG GTTCAAGCAG ATGGTTCAGG AGCTAAGTTA AGCCATGGTC TGCCTCAAAA     300

CACTAACCAA AGAGGAATTC TTAATGATAC TGGGGCTTCT TAGATACAGA ACATCTTGAA     360

GGGTTGGGGG CAATGGCTTA TGCCTGTAAT                                      390
```

(2) INFORMATION FOR SEQ ID NO:27:

(i) SEQUENCE CHARACTERISTICS:
                  (A) LENGTH: 547
                  (B) TYPE: nucleic acid
                  (C) STRANDEDNESS: double
                  (D) TOPOLOGY: linear (ii) MOLECULE TYPE: genomic DNA (iii) HYPOTHETICAL: no (iv) ANTI-SENSE: no (vi) ORIGINAL SOURCE:
                  (A) ORGANISM: human (x) FEATURE:
                  (D) OTHER INFORMATION: exon 12 of HIP1

(xi) SEQUENCE DESCRIPTION: SEQ ID NO: 27:

```
AAAATCAATA ACCATGGATT TATGAGTATT AGATTAGTAT CTGGTAACAT TTAGAGTATA      60

ATTTATGGCA TTTCAAAGAA TTGTCCCCAA ATTAATACCA GCTTTTAATT TCCTCCCCTG     120

AGCTCACAAT TAAAAACAGA GGGATAGAAG CACTATGAAA GCAAACTCAT TCCCCTTCTC     180

TTCCCAGGGA CCACTTAATT GAGCGACTAT ACAGAGAGAT CAGTGGATTG AAGGCACAGC     240

TAGAAAACAT GAAGACTGAG GTATAACTTG GATCTGCTCT GCCTTTGCGC TTCACCAAAA     300

CACGGTAGAT TTGAATGTTA AATTTGCATC ACACTAGCCA GGCACAGTGG CTCACACCTG     360

TAATCCTAGC ACTTTGGGAG GCCAAGGCAG GAGGATTACC TGAGGTCGGG AGTTCGAGAC     420

CAGCCTGGGC AACAGGGTGA AACCCCCGTC TTCAATAAAA ATGCAATAAT TAGCCGGGTG     480

TGTTGGCAGG CACCTGTAAT CCCAGCTACT CGGGAAGCTG AGGCATGAGA ATTGCTTGAA     540

CTTGGGA                                                               547
```

(2) INFORMATION FOR SEQ ID NO:28:

(i) SEQUENCE CHARACTERISTICS:
                  (A) LENGTH: 436
                  (B) TYPE: nucleic acid
                  (C) STRANDEDNESS: double
                  (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 13 of HIP1

(xi) SEQUENCE DESCRIPTION: SEQ ID NO: 28:

| | | | | | |
|---|---|---|---|---|---|
| CCCCCAGCCA | CTCTAAAGAG | GACCACAATT | CCCCGGCCAT | CATCCCCTGT | TATTGTTGTT | 60 |
| GATTGAGGGG | CTCCTAATGA | CCAGATGGTC | CAACCCTCCT | GGGACGTGGA | GAGTTGACTT | 120 |
| AGGGGAATCA | GGTATTTACT | TGGAAGCATG | GTAGGACCCG | CTTCTCCGGC | CCATGCCCGT | 180 |
| GACCCGTGGC | AGTGGGCGGT | TGGCCTCATG | ACCGGAGTCC | CCCCACAGAG | CCAGCGGGTT | 240 |
| GTGCTGCAGC | TGAAGGGCCA | CGTCAGCGAG | CTGGAAGCAG | ATCTGGCCGA | GCAGCAGCAC | 300 |
| CTGCGGCAGC | AGGCGGCCGA | CGACTGTGAA | TTCCTGCGGG | CAGAACTGGA | CGAGCTCAGG | 360 |
| AGGCAGCGGG | AGGACACCGA | GAAGGCTCAG | CGGAGCCTGT | CTGAGATAGA | AAGTGAGCGG | 420 |
| TGGGTGGGGG | CGGGGG | | | | | 436 |

(2) INFORMATION FOR SEQ ID NO:29:

(i) SEQUENCE CHARACTERISTICS:
        (A) LENGTH: 469
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 14 of HIP1

(xi) SEQUENCE DESCRIPTION: SEQ ID NO: 29:

| | | | | | |
|---|---|---|---|---|---|
| GACTTGAGCC | CAAGGAGGTC | AAGGCTGCAG | TGAACAGTGA | TTGTGCCACT | GCACCCCAGC | 60 |
| CTGGGTGACA | GAGCAAGACT | GTCTCAAAAC | AAAACAAGGA | GGACCTTCTA | GGGACCCTGG | 120 |
| CTCATTGCAA | GGAAGGCAAG | GGTCCCTGCT | AGGTTAGACT | CCTCACCTTG | GTCCTTTACA | 180 |
| ATACAGGGAA | AGCTCAAGCC | AATGAACAGC | GATATAGCAA | GCTAAAGGAG | AAGTACAGCG | 240 |
| AGCTGGTTCA | GAACCACGCT | GACCTGCTGC | GGAAGGTAAG | ACCCTCAGCC | CCTGTCACCA | 300 |
| TCCTGCAGGC | CCTGCACCTC | TAGGGAGAGA | GCGGCTCAGG | CCTGTGGCTT | CCCCGGGGCC | 360 |
| AGCAACCCCT | ACATTGATCT | CTAAGGCATT | GCCGTCATCT | CGGGAACCAC | ACCTTTTCAG | 420 |
| GCTTCCTTGC | CTCTGTGTCT | TGGGCTGTGT | CCTGGGTGCC | AATCCCATG | | 469 |

(2) INFORMATION FOR SEQ ID NO:30:

(i) SEQUENCE CHARACTERISTICS:
        (A) LENGTH: 359
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
    (A) ORGANISM: human (x) FEATURE:
    (D) OTHER INFORMATION: exon 15 of HIP1

(xi) SEQUENCE DESCRIPTION: SEQ ID NO: 30:

```
GGGTAGGAAA GTGATTCCTG TGTCTGACTC TAGGGCACGC ACAGCCTGAG TATGATTGTC    60

CTAGAAGGAG GATGTCCTCT AAGCCTGGGA TCTCCTGGTT CAAGACACTG TTCTTCTTTT   120

GCAGAATGCA GAGGTGACCA AACAGGTGTC CATGGCCAGA CAAGCCCAGG TAGATTTGGA   180

ACGAGAGAAA AAAGAGCTGG AGGATTCGTT GGAGCGCATC AGTGACCAGG GCCAGCGGAA   240

GGTGAGTGGG ACGAGGAGCA CTCGGGAAAT GAGGGAGGGG GCTGTTGAGT TGGTGGCGGG   300

GGCTTTGTGG CCTTCTGCTC CATGGGCAGT TCTGTGGGTC GGTTGGCATC ACACAGCAG    359
```

(2) INFORMATION FOR SEQ ID NO:31:

(i) SEQUENCE CHARACTERISTICS:
        (A) LENGTH: 209
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 16 of HIP1

(xi) SEQUENCE DESCRIPTION: SEQ ID NO: 31:

```
GTTGATCGCT TGGGACGTTT TTACATTTTT ATATTCTTTG TCACTGTCAC CCAGATCAGA    60

GTCCCTCTGT TTTTCTTCTC TTTCAGACTC AAGAACAGCT GGAAGTTCTA GAGAGCTTGA   120

AGCAGGAACT TGCCACAAGC CAACGGGAGC TTCAGGTTCT GCAAGGCAGC CTGGAAACTT   180

CTGCCCAGGT AAATACCTCC TTTTTTTTT                                     209
```

(2) INFORMATION FOR SEQ ID NO:32:

(i) SEQUENCE CHARACTERISTICS:
        (A) LENGTH: 485
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 17 of HIP1

(xi) SEQUENCE DESCRIPTION: SEQ ID NO: 32:

```
CCCCCACTGC AATCAGTGTG TCCCCGGGAG GGAATCAGAG TGGCAGGTTA AAGAGCCATC    60
```

```
ACCTTCCCAG TCCTTGCAAC CCGGTGGTGG GTTGGACCTC TGGGAAGTAG GGACTGTTTA      120

ACTCAACCAG CGTCTCCCTC TTTCCTTGTG GTCACCTTTG CAGTCAGAAG CAAACTGGGC      180

AGCCGAGTTC GCCGAGCTAG AGAAGGAGCG GGACAGCCTC GTGAGTGGCG CAGCTCATAG      240

GGAGGAGGAA TTATCTGCTC TTCGGAAAGA ACTGCAGGAC ACTCAGCTCA AACTGGCCAG      300

CACAGAGGGT CACGGACATG GACACGAGCG AGCACCTGTG AATTCCCACC GAGGGCCTCT      360

GCGCATGCAC GGAGGCTGGG AGGACCCCGG GGCTGCTGAG AAGGGGTTTG GGGCCTTGGC      420

CTGATTGTGC AGACATTCTG TAGGTGTAAT GCCAGCAGGC CCTGCATTGC CTGCAGAGTC      480

CATGA                                                                  485
```

(2) INFORMATION FOR SEQ ID NO:33:

(i) SEQUENCE CHARACTERISTICS:
        (A) LENGTH: 468
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 18 of HIP1

(xi) SEQUENCE DESCRIPTION: SEQ ID NO: 33:

```
TTACTGGCTT GGACCTCATT GGCCATGACT TGAGCTAAGA TGCTAAGAGC CCCAGCCAGG       60

TCATCCTGCT CAGGTTCATT ATGGAGTCTA GGGCAGACTC TCACCTCCCT GGACCATTTT      120

TAGAATCTAT GTGCCAGCTT GCCAAAGACC AACGAAAAAT GCTTCTGGTG GGGTCCAGGA      180

AGGCTGCGGA GCAGGTGATA CAAGACGCCC TGAACCAGCT TGAAGAACCT CCTCTCATCA      240

GCTGCGCTGG GTCTGCAGGT ACACTTGCAA TTGCCCAGCT GGCAGGGGCC AGGTCCTTAC      300

AGCCTGAGAC TCTGTTGATG TTGAATCTCA TGTGAGACTT AGCTCAGGGG CTCTCAGCCC      360

AGCAGCATGT CAGCATTACC TTAGGGGCGC CCAGGCCCCA TCCTAGATCA GTTACATGTG      420

GAAACTCTGT GCATTAGTGC CTATACACTA GTATTTTAGT ATTTTCTT                   468
```

(2) INFORMATION FOR SEQ ID NO:34:

(i) SEQUENCE CHARACTERISTICS:
        (A) LENGTH: 393
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 19 of HIP1

(xi) SEQUENCE DESCRIPTION: SEQ ID NO: 34:

```
CACTAGTAAG CTCCTCCATT CAGTGCTTAA TTAACGAGGA TGAAGCCAGC TATGAGAACT       60
```

```
TGCTCTGACC TTGCCCTGTG TTCCCTCTCA CAGATCACCT CCTCTCCACG GTCACATCCA      120

TTTCCAGCTG CATCGAGCAA CTGGAGAAAA GCTGGAGCCA GTATCTGGCC TGCCCAGAAG      180

GTAAGAATGG CCAAGGACAG TCTCTGTCGG CTAGTGATGG CCAGACAGGG TTCAGAAGCA      240

CCTGAATGCG GGGATAGTGA CAGGTCCCTC TGCATCAAGA AAGGCATGTA GGCAACTCAT      300

ACAAGAAAGG CATGTAGGCA ACTCATAAAA CGGGAGGAGA GGGTATGAAA GTGTCACCAT      360

CAACCAGACC TGAGAAACTT CTCTTTCCAA TCC                                   393

(2) INFORMATION FOR SEQ ID NO:35:

(i) SEQUENCE CHARACTERISTICS:
        (A) LENGTH: 421
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 20 of HIP1

(xi) SEQUENCE DESCRIPTION: SEQ ID NO: 35:

GGCCTGCCCA GAAGGTAAGA ATGGCCAAGG ACAGTCTCTG TCGGCTAGTG ATGGCCAGAC       60

AGGGTTCAGA AGCACCTGAA TGCGGGGATA GTGACAGGTC CCTCTGCATC AAGAAAGGCA      120

TGTAGGCAAC TCATACAAGA AAGGCATGTA GGCAACTCAT AAAACGGGAG GAGAGGGTAT      180

GAAAGTGTCA CCATCAACCA GACCTGAGAA ACTTCTCTTT CCAATCCTGG CAGACATCAG      240

TGGACTTCTC CATTCCATAA CCCTGCTGGC CCACTTGACC AGCGACGCCA TTGCTCATGG      300

TGCCACCACC TGCCTCAGAG CCCCACCTGA GCCTGCCGAC TGTGAGTACT GGGGCATGAG      360

GGGCTGTTCA TGGACCAGGG GAGCAGGGGG CCTTTAAAAG TCTCTGTTGG GCCGGGCGCA      420

G                                                                     421

(2) INFORMATION FOR SEQ ID NO:36:

(i) SEQUENCE CHARACTERISTICS:
        (A) LENGTH: 498
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 21 of HIP1

(xi) SEQUENCE DESCRIPTION: SEQ ID NO: 36:

AGGCCGAGGC AGGAGAATCG CTTGAACTCA GGAGGCGGAG TTTGCAGTGA GCCGAGATGG       60

CGCCACTGCA CTCCAGCCTG GGCAACAAGA GCGAGACTCC ATCTCAAAAA AAAAGTGTCT      120
```

| | |
|---|---:|
| ATTGCCTTGT ATCTCCAGCA CTGACCGAGG CCTGTAAGCA GTATGGCAGG GAAACCCTCG | 180 |
| CCTACCTGGC CTCCCTGGAG GAAGAGGGAA GCCTTGAGAA TGCCGACAGC ACAGCCATGA | 240 |
| GGAACTGCCT GAGCAAGATC AAGGCCATCG GCGAGGTACT TGGAGTAGTA TCATTGAGGA | 300 |
| GCATTGTTAT TCTTCTGGGT GTGCGTGCTG GTGAATGGCC AGGGAATCGG TGATGTTCTG | 360 |
| AGCTAGTTCT TTCTGCACTT AGAACTTGAT TCTAGAAAGA GATTGTTAAA ATTGGAAAAT | 420 |
| CTGGCCGGGT GCAGTGATTT ATGCGTGTAA TCCCAGCACT TTGGGAGGCC GAGTCAGGAG | 480 |
| GATCACTTGA GGCTAGAC | 498 |

(2) INFORMATION FOR SEQ ID NO:37:

(i) SEQUENCE CHARACTERISTICS:
      (A) LENGTH: 427
      (B) TYPE: nucleic acid
      (C) STRANDEDNESS: double
      (D) TOPOLOGY: linear (ii) MOLECULE TYPE: genomic DNA (iii) HYPOTHETICAL: no (iv) ANTI-SENSE: no (vi) ORIGINAL SOURCE:
      (A) ORGANISM: human (x) FEATURE:
      (D) OTHER INFORMATION: exon 22 of HIP1

(xi) SEQUENCE DESCRIPTION: SEQ ID NO: 37:

| | |
|---|---:|
| CCCTGTGGCT TGCAGAAGGT GTTTGCTGGG TGGCCTCCTG CCTTGCCATC TTGTAAGGGT | 60 |
| TACAGATGGC AGAGGAGAAG AGACAGGAGG CCCCAAGGTC AGTTCAGCCT TTGTGATGTG | 120 |
| TTCACAGGAG CTCCTGCCCA GGGGACTGGA CATCAAGCAG GAGGAGCTGG GGACCTGGT | 180 |
| GGACAAGGAG ATGGCGGCCA CTTCAGCTGC TATTGAAACT GCCACGGCCA GAATAGAGGT | 240 |
| AGGAGGTTCC TGCAGGATCT CCTGAAACGA TGCCTTTGCA GCTGCCCTTC TGCAACACTG | 300 |
| CTCATTAAAC ATGTCACAGT CGTTCATTAA GGCCATGGCA ACCCCTAAG ACAGAAACCA | 360 |
| GAATTTGCCA GGCACAGTGG CTCATGCCTG TAACCCCAGC ACCTTGGGAG GATCACTTGA | 420 |
| GTCCAGG | 427 |

(2) INFORMATION FOR SEQ ID NO:38:

(i) SEQUENCE CHARACTERISTICS:
      (A) LENGTH: 367
      (B) TYPE: nucleic acid
      (C) STRANDEDNESS: double
      (D) TOPOLOGY: linear (ii) MOLECULE TYPE: genomic DNA (iii) HYPOTHETICAL: no (iv) ANTI-SENSE: no (vi) ORIGINAL SOURCE:
      (A) ORGANISM: human (x) FEATURE:
      (D) OTHER INFORMATION: exon 23 of HIP1

(xi) SEQUENCE DESCRIPTION: SEQ ID NO: 38:

| | |
|---|---:|
| CCCCCTGAAT AGGTTAGAGT CTGGATTCTT TTCTGACTCT CTCAAGAATG TGGGCAGGGA | 60 |
| CTTGGGGACT TCCAGATTCA GGTTTCCCAG CTACCACACG ATGTTGGACT GAAAGTATAG | 120 |

TAAGACATTA GTGGATCCTT AATATTCAAG GCACATTTAG AAACCATGCT TCTTTTTCAC        180

AGGAGATGCT CAGCAAATCC CGAGCAGGAG ACACAGGAGT CAAATTGGAG GTGAATGAAA        240

GGTCGGTCTG AGCGGCATGG TGGGACCTAG GGGAGCAGGA TCTGTCTTCC TGACATTGGT        300

CTATACTTTG CATACTTATT AGGGAATTAG AGGAGAGCAG TAGCAGCCAC GGGGAAGGGC        360

TGAGTTG                                                                 367

(2) INFORMATION FOR SEQ ID NO:39:

(i) SEQUENCE CHARACTERISTICS:
        (A) LENGTH: 502
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 24 of HIP1

(xi) SEQUENCE DESCRIPTION: SEQ ID NO: 39:

CCCCGCAGAA TGTTCCAGCA ACCTCAGCAC CCTTCTTACC TCCCTTTCCC ATTCCAAGCT        60

TGCCTTTGGC TAGGAGTGGG GAAGAGAACC GTCGTGTTCA TTGATCTTGG ATCTTGATCT        120

CAGTGTATCC TCGACTTGTT TGTTTGGCAG GATCCTTGGT TGCTGTACCA GCCTCATGCA        180

AGCTATTCAG GTGCTCATCG TGGCCTCTAA GGACCTCCAG AGAGAGATTG TGGAGAGCGG        240

CAGGGTGAGC GTGGGTGTGG GCCCTGGGCA GGAAGAGGAG GCATCGGTGA CAGACTCCCG        300

CTCCAACGGA CTCTGTGATG CTGCCGTCTT ACTCTGTGTG TCCACCTGAG TACAGAGCAG        360

CCACTCCTGT AGATATCAGC AGAGGCCCTG GGGAGAAGTC AGAGCTCCAG GACCTCCCCA        420

GAGGGTGGCC AGGCATGTGT CCCAACTCCA GCTCCCTTCG CACAGGCAGA CATTGTTGGA        480

ACTTGCTGTG GGAGCCCTTT TT                                                502

(2) INFORMATION FOR SEQ ID NO:40:

(i) SEQUENCE CHARACTERISTICS:
        (A) LENGTH: 437
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 25 of HIP1

(xi) SEQUENCE DESCRIPTION: SEQ ID NO: 40:

TTTTGGTCTC TGAATCTTCT TCTTTTTTGT AAAATGGGAA TACTAATGCT TATGTCTCAG        60

AGTTACTATG AGGATGATTT GGGATAATAT ATGTATAAAA GCACCTGCCA TATAGTACAT        120

```
GCTCAATAAA AGGTGGCTAT TACTATTTTT TATTTCCCTA GGGTACAGCA TCCCCTAAAG      180

AGTTTTATGC CAAGAACTCT CGATGGACAG AAGGACTTAT CTCAGCCTCC AAGGCTGTGG      240

GCTGGGGAGC CACTGTCATG GTGTAAGTAT CTATTGGTAC CAAGGGTCCT CCCATGACCC      300

CTCTTCCATT GATCCACTCC AAACAATAGC TAAGGAGGGA AAAAAAAATC TGTCCCTTAG      360

AAATAAACTA TTGATCAGGA AGTCAATAGG ACCGAGTTTA CAAGGGAGCC TGGCTCTCCC      420

AGGGGACACA GGGCAGG                                                    437
```

(2) INFORMATION FOR SEQ ID NO:41:

(i) SEQUENCE CHARACTERISTICS:
        (A) LENGTH: 351
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 26 of HIP1

(xi) SEQUENCE DESCRIPTION: SEQ ID NO: 41:

```
GGGAGCCTGG CTCTCCCAGG GGACACAGGG CAGGCAGCCT CCCCTCCCTG TTTAGCCAAG       60

GGCGATGGGG TGGTCTGGAG GTGGGATTGT GGAGGAGTTG CAGCTCATTT GCCCGTAACC      120

TAGTCCCTCT TGTCGTTTTC CATCAGGGAT GCAGCTGATC TGGTGGTACA AGGCAGAGGG      180

AAATTTGAGG AGCTAATGGT GTGTTCTCAT GAAATTGCTG CTAGCACAGC CCAGCTTGTG      240

GCTGCATCCA AGGTAGGACC TGGCTGGACC TCCTAGGACG CTGGAAGGCC TGGTTAGAGA      300

GTACTAGGCT AGGTTAAAGA GTACTTGGCT GCGTTAGGCA GTACTTGGCT G               351
```

(2) INFORMATION FOR SEQ ID NO:42:

(i) SEQUENCE CHARACTERISTICS:
        (A) LENGTH: 418
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 27 of HIP1

(xi) SEQUENCE DESCRIPTION: SEQ ID NO: 42:

```
CTTTTTATAT GATAGATATG TCAGGAGCTG ACTATAGTCA GCAGATTTTG AGAAGCTGAT       60

TGGTGATTGC CGTTTGGCCC ACATATGTTT GCTAAGAACC ATCAGAGCAA TTATCTGATT      120

CAGTCCTTGT TGCTCTAGGT GTTGTATGAA CCTAAATCTG CTTTGTCCTG GTAGGTGAAA      180

GCTGATAAGG ACAGCCCCAA CCTAGCCCAG CTGCAGCAGG CCTCTCGGGG AGTGAACCAG      240

GCCACTGCCG GCGTTGTGGC CTCAACCATT TCCGGCAAAT CACAGATCGA AGAGACAGGT      300
```

```
AGCCTTTCCA AAGGGACCCT TTTCTTACCC ACCCTGTTGA GCTCTTCTCT GCATCCTTCC      360

CTGTGATCCC AACCAAATCC CACAGGACTG TGTCTAAATT CTTTCATATT TTTCATCT       418
```

(2) INFORMATION FOR SEQ ID NO:43:

(i) SEQUENCE CHARACTERISTICS:
        (A) LENGTH: 279
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 28 of HIP1

(xi) SEQUENCE DESCRIPTION: SEQ ID NO: 43:

```
TTTCCACAGA GCATTGGCAT TGGCTGCCTC TCAGGTGCCA GTCAGCCAGG GTAGAATTTG       60

ATGAGACCTT CTTGTTTCCA TCCTTGCAGA CAACATGGAC TTCTCAAGCA TGACGCTGAC      120

ACAGATCAAA CGCCAAGAGA TGGATTCTCA GGTTAGGGTG CTAGAGCTAG AAAATGAATT      180

GCAGAAGGAG CGTCAAAAAC TGGGAGAGCT TCGGAAAAAG CACTACGAGC TTGCTGGTGT      240

TGCTGAGGGC TGGGAAGAAG GTAAGCTGAC TCAAAGGAT                             279
```

(2) INFORMATION FOR SEQ ID NO:44:

(i) SEQUENCE CHARACTERISTICS:
        (A) LENGTH: 3715
        (B) TYPE: nucleic acid
        (C) STRANDEDNESS: double
        (D) TOPOLOGY: linear (ii) MOLECULE TYPE: genomic DNA (iii) HYPOTHETICAL: no (iv) ANTI-SENSE: no (vi) ORIGINAL SOURCE:
        (A) ORGANISM: human (x) FEATURE:
        (D) OTHER INFORMATION: exon 29 and partial cds of HIP1

(xi) SEQUENCE DESCRIPTION: SEQ ID NO: 44:

```
AACATAAATT ATCATTGTCT TTTAGGAACA GAGGCATCTC CACCTACACT GCAAGAAGTG       60

GTAACCGAAA AAGAATAGAG CCAAACCAAC ACCCCATATG TCAGTGTAAA TCCTTGTTAC      120

CTATCTCGTG TGTGTTATTT CCCCAGCCAC AGGCCAAATC CTTGGAGTCC CAGGGGCAGC      180

CACACCACTG CCATTACCCA GTGCCGAGGA CATGCATGAC ACTTCCCAAA GACTCCCTCC      240

ATAGCGACAC CCTTTCTGTT TGGACCCATG GTCATCTCTG TTCTTTTCCC GCCTCCCTAG      300

TTAGCATCCA GGCTGGCCAG TGCTGCCCAT GAGCAAGCCT AGGTACGAAG AGGGGTGGTG      360

GGGGGCAGGG CCACTCAACA GAGAGGACCA ACATCCAGTC CTGCTGACTA TTTGACCCCC      420

ACAACAATGG GTATCCTTAA TAGAGGAGCT GCTTGTTGTT TGTTGACAGC TTGGAAAGGG      480

AAGATCTTAT GCCTTTTCTT TTCTGTTTTC TTCTCAGTCT TTTCAGTTTC ATCATTTGCA      540
```

```
CAAACTTGTG AGCATCAGAG GGCTGATGGA TTCCAAACCA GGACACTACC CTGAGATCTG    600

CACAGTCAGA AGGACGGCAG GAGTGTCCTG GCTGTGAATG CCAAAGCCAT TCTCCCCCTC    660

TTTGGGCAGT GCCATGGATT TCCACTGCTT CTTATGGTGG TTGGTTGGGT TTTTTGGTTT    720

TGTTTTTTTT TTTTAAGTTT CACTCACATA GCCAACTCTC CCAAAGGGCA CACCCCTGGG    780

GCTGAGTCTC CAGGGCCCCC CAACTGTGGT AGCTCCAGCG ATGGTGCTGC CCAGGCCTCT    840

CGGTGCTCCA TCTCCGCCTC CACACTGACC AAGTGCTGGC CCACCCAGTC CATGCTCCAG    900

GGTCAGGCGG AGCTGCTGAG TGACAGCTTT CCTCAAAAAG CAGAAGGAGA GTGAGTGCCT    960

TTCCCTCCTA AAGCTGAATC CCGGCGGAAA GCCTCTGTCC GCCTTTACAA GGGAGAAGAC   1020

AACAGAAAGA GGGACAAGAG GGTTCACACA GCCCAGTTCC CGTGACGAGG CTCAAAAACT   1080

TGATCACATG CTTGAATGGA GCTGGTGAGA TCAACAACAC TACTTCCCTG CCGGAATGAA   1140

CTGTCCGTGA ATGGTCTCTG TCAAGCGGGC CGTCTCCCTT GGCCCAGAGA CGGAGTGTGG   1200

GAGTGATTCC CAACTCCTTT CTGCAGACGT CTGCCTTGGC ATCCTCTTGA ATAGGAAGAT   1260

CGTTCCACTT TCTACGCAAT TGACAAACCC GGAAGATCAG ATGCAATTGC TCCCATCAGG   1320

GAAGAACCCT ATACTTGGTT TGCTACCCTT AGTATTTATT ACTAACCTCC CTTAAGCAGC   1380

AACAGCCTAC AAAGAGATGC TTGGAGCAAT CAGAACTTCA GGTGTGACTC TAGCAAAGCT   1440

CATCTTTCTG CCCGGCTACA TCAGCCTTCA AGAATCAGAA GAAAGCCAAG GTGCTGGACT   1500

GTTACTGACT TGGATCCCAA AGCAAGGAGA TCATTTGGAG CTCTTGGGTC AGAGAAAATG   1560

AGAAAGGACA GAGCCAGCGG CTCCAACTCC TTTCAGCCAC ATGCCCCAGG CTCTCGCTGC   1620

CCTGTGGACA GGATGAGGAC AGAGGGCACA TGAACAGCTT GCCAGGGATG GGCAGCCCAA   1680

CAGCACTTTT CCTCTTCTAG ATGGACCCCA GCATTTAAGT GACCTTCTGA TCTTGGGAAA   1740

ACAGCGTCTT CCTTCTTTAT CTATAGCAAC TCATTGGTGG TAGCCATCAA GCACTTCCCA   1800

GGATCTGCTC AACAGAATA TTGCTAGGTT TTGCTACATG ACGGGTTGTG AGACTTCTGT   1860

TTGATCACTG TGAACCAACC CCCATCTCCC TAGCCCACCC CCCTCCCCAA CTCCCTCTCT   1920

GTGCATTTTC TAAGTGGGAC ATTCAAAAAA CTCTCTCCCA GGACCTCGGA TGACCATACT   1980

CAGACGTGTG ACCTCCATAC TGGGTTAAGG AAGTATCAGC ACTAGAAATT GGGCAGTCTT   2040

AATGTTGAAT GCTGCTTTCT GCTTAGTATT TTTTTGATTC AAGGCTCAGA AGGAATGGTG   2100

CGTGGCTTCC CTGTCCCAGT TGTGGCAACT AAACCAATCG GTGTGTTCTT GATGCGGGTC   2160

AACATTTCCA AAAGTGGCTA GTCCTCACTT CTAGATCTCA GCCATTCTAA CTCATATGTT   2220

CCCAATTACC AAGGGGTGGC CGGGCACAGT GGCTCACGCC TGTAATCCCA GCACTTTGAG   2280

AGGCTGAGGT GGTAGGATCA CCTGAGGTCA GGAGTTCAAG ACCAGCCTGT CCAACATGGT   2340

GAAACCCCCA TCTCTACTAA AAATACCAAA AATTAGCCGA GCGTAGTGAC GGGTGCCCGT   2400

AATCCCAGCT ACTCAGGAGG CTGAGACAGG AGAATCACCT GAACCCCAGA GGCAGAGGTT   2460

GCAGTGAGCT GAGATCACGC CATTGTACTC CAGCCTGGGC AACAAGAGCA AAACTCCGTC   2520

TCAAAAAAAA AAAAAATTA CAAATGGGGC AAACAGTCTA GTGTAATGGA TCAAATTAAG   2580

ATTCTCTGCC CAGCCGGGCA CAGTGGCGCA TGCCTGTAAT CCCAGAACTT TGGGAGGCCA   2640

AGACGGGATG ATTGCTTGAG CTCAGGAGTT TGAGACCAGG CTGGGCATCA TAGCAAGACC   2700

TCATCTCTAC TAAAATTCAA AAACAAAATT AGCCGGGCAT GATGGTGCAT GCCTGTAGTC   2760

TCAGCTAGTT GGGGAGCTAA GGTGGGAGAA TTGCTTGAGC TTGGGAAGTC GAGGCTGCAG   2820

TCAGCCCTGA TTGTGCCAGT GCACTCCGGC CTGGGTGACA GAGTGAGACC CGTGCTCAAA   2880

AAAAAAAAGA TTCTGTGTCA GAGCCCAGCC CAGGAGTTTG AGGCTGCAAT GAGCCATGAT   2940
```

```
                                      -continued

TTCCCACTGC ACTCCAGCCT GAGTGACAGA GCGAGACTCC ATCTCTTTAA AAACAAACAA    3000

AAAATTATCT GAATGATCCT GTCTCTAAAA AGAAGCCACA GAAATGTTTA AAAACTTCAT    3060

CGACTTAGCC TGAGTCATAA CGGTTAAGAA AGCACTTAAA CAGAAGCAGA GGCTAATTCA    3120

GTGTCACATG AGGAAGTAGC TGTCAGATGT CACATAATTA CTTTCGTAAT AGCTCAGATT    3180

AGAATGGCTA CCCCATTCTC TAGACAAAAT CAAATTGTCC TATTGTGACT CTTCTAAAAA    3240

TGAAGATGAA GAGCTATTTA ATGACACACC TTGGATTAAA ACGGGAATCA CATCTTAAAG    3300

CTAAAAATGA ACCTGCAAGC CTTCTAAATG AGTCACTGAG CATCACTAGT GACAAGTCTC    3360

GGGTGAGCGT AAATGGGTCA TGACAAGATG GGACAGCAAC AAAATCATGG CTTAGGATCG    3420

ACAAGAAGTT AAAAAACAGC TGCATCTGTT ACTTAAGTTT GTAAGACAGT GCCCTGAGAC    3480

CTCTAGAGAA AAGATGTTTG TTTACATAAG AGAAAGAAGG CCAGACATGG TGTCTCACAC    3540

GTTTAATCCC AGCACTTTGG GAGGCAGGGG CGGGTGGATC ACCTGAGGTC AGGAGTTCAA    3600

GACTAGCCTG GCCAACATGG TGAAACCCCG TCTCTACTAA AAATACAAAA ATTAGCCGGG    3660

CATGGTGGCA GGCGCCTATA ATCCCAGCTA CTGGGAGGC TGAGGCAGGA GAATC          3715
```